US009926586B2

(12) United States Patent
Perez Girona et al.

(10) Patent No.: US 9,926,586 B2
(45) Date of Patent: Mar. 27, 2018

(54) **RAPID METHOD FOR DETECTION OF *SALMONELLA* LIVE VACCINE STRAINS**

(71) Applicant: Integrated Microsystems For Quality of Life, S.L., Tarragona (ES)

(72) Inventors: Cristina Perez Girona, Lleida (ES); Pablo Lozano Sánchez, Tarragona (ES); Gemma Freixes Prous, Barcelona (ES); Sergio Martinez Montequín, Tarragona (ES); Anna Pallares Lleo, Tarragona (ES); Bruno Teixeira Dias, Tarragona (ES); Katia Uliaque Cugat, Tarragona (ES)

( * ) Notice: Subject to any disclaimer, the term of this patent is extended or adjusted under 35 U.S.C. 154(b) by 0 days.

(21) Appl. No.: 15/072,167

(22) Filed: Mar. 16, 2016

(65) Prior Publication Data

US 2016/0215323 A1 Jul. 28, 2016

Related U.S. Application Data

(63) Continuation-in-part of application No. 14/161,117, filed on Jan. 22, 2014.

(60) Provisional application No. 61/927,401, filed on Jan. 14, 2014.

(30) Foreign Application Priority Data

Jan. 22, 2013 (ES) .................................. 201330064

(51) Int. Cl.
*C12Q 1/10* (2006.01)
*G01N 33/569* (2006.01)
*C12Q 1/04* (2006.01)

(52) U.S. Cl.
CPC .............. *C12Q 1/10* (2013.01); *C12Q 1/045* (2013.01); *G01N 33/56916* (2013.01); *G01N 2333/255* (2013.01)

(58) Field of Classification Search
None
See application file for complete search history.

(56) References Cited

U.S. PATENT DOCUMENTS

| 5,208,150 | A | 5/1993 | Tate et al. |
| 5,843,699 | A | 12/1998 | Strenkoski et al. |
| 2003/0153028 | A1 | 8/2003 | Refseth et al. |
| 2004/0241644 | A1 | 12/2004 | Samadpour |
| 2011/0159515 | A1 | 6/2011 | Stimson |
| 2012/0107864 | A1 | 5/2012 | Sparbier et al. |

FOREIGN PATENT DOCUMENTS

| CN | 101423862 A | 5/2009 |
| EP | 0877092 A1 | 11/1998 |
| NO | 2006130927 A1 | 12/2006 |

OTHER PUBLICATIONS

Fricker 1987 (The isolation of *Salmonellas* and campylobacters; Journal of Applied Bacteriology; 63:99-116).*
Shultz et al. 2010 (Optimized culturing and nucleic acid based methods for the detection of *Salmonella enterica* in poultry environments; Poultry Science 21(11): 2761-2766).*
Jefferies 1959 (Novobiocin-tetrathionate broth: A medium of improved selectivity for the isolation of *Salmonellae* from faeces; J Clin Path 12:568-571; see p. 568, Table 1; and pp. 568-569 bridging section).*
Fluit et al. 1993 (Rapid Detection of *Salmonellae* in Poultry with the Magnetic Immuno-Polymerase Chain Reaction Assay; Applied and Environmental Microbiology 59(5):1342-1346).*
Blivet et al. 1998 (Development of a new cultrue medium for the rapid detection of *Salmonella* by indirect conductance measurements; Journal of Applied Microbiology 84: 399-403).*
Blivet et al. 1998 Development of a new culture medium for the rapid detection of *Salmonella* by indirect conductance measurements; Journal of Applied Microbiology 84: 399-403.
Colby, et al., Prion detection by an amyloid seeding assay; PNAS, vol. 105, No. 5, pp. 20914-20919.
Fluit et al. 1993 Rapid Detection of *Salmonellae* in Poultry with the Magnetic Immuno-Polymerase Chain Reaction Assay; Applied and Environmental Microbiology 59(5)1342-1346.
Fricker "The isolation of *Salmonellas* and campylobacters" Journal of Applied Bacteriology 1987 63 99-16.
Gorski "Selective Enrichment Media Bias the Types of *Salmone:a enterica* Isolated from Mixed Strain Cultures and Complex Enrichment Broths," Plos One, vol. 7, No. 4, p. 34722.
Himedia Technical Data for Lysine Iron Cystine Broth Base (M845). 2011. HiMedia Laboratories Pvt. Ltd. A-516, Swastik Disha Business Park, via Vadhani Ind. Est., LBS Marg, Mumbai-400086, India. Email: techhelp@himedialabs.com.
International Search Report and Written Opinion, PCT/EP2014/051274, dated Apr. 8, 2014.
International Search Report and Written Opinion, PCT/EP2016/055720, dated Dec. 9, 2016.
Jefferies "Novobiocin-tetrathionate broth: A medium of improved selectivity for the isolation of *Salmonellae* from faeces" 1959 J Clin Path 12:568-571; see p. 568, Table 1; and pp. 568-569 bridging section.
Kauffman "Tetrathionate Broth Base (with Novobiocin)(9221)" (Oct. 1, 2008), HIMedia Laboratories, Technical Data, Retrieved from Internet, URL: http//www.neogen.com/Acumedia/pdf/prodinfo/9221_PI.pdf, pp. 1-3.
Lillehaug "An Improved plaque assay for poor plaque-producing temperate lactococcal bacteriophages," Journal of Applied Microbiology, vol. 83, pp. 85-90.
Morinigo et al. "Laboratory study of several enrichment broths for the detection of *Salmonella* spp. Particularly in relation to water samples," 1993, Journal of Applied Bacteriology, vol. 74, pp. 330-335.
Odumeru et al. "*Salmonella* Detection Methods for Food and Food Ingredients," *Salmonella*—A dangerous Foodbourne Pathogen, (2012), InTech, pp. 373-393.

(Continued)

*Primary Examiner* — Mary Lyons
(74) *Attorney, Agent, or Firm* — Entralta P.C.; Meghan Van Leeuwen; Peter D. Weinstein

(57) ABSTRACT

The present specification discloses methods of detecting a pathogen of interest, components useful in carrying out these methods, including a pre-enrichment media, and enrichment media and a detection solution and kits thereof.

7 Claims, 6 Drawing Sheets

(56) References Cited

OTHER PUBLICATIONS

Reveal microbiological screening test for *Salmonella*, (Jan. 1, 2001), XP055110682, Retrieved from internet, URL:http://www.neogen.com/FoodSafety/pdf/ProdInfo/R2-Sal.pdf, pp. 1-2.
Shultz et al. "Optimized culturing and nucleic acid based methods for the detection of *Salmonella enterica* in poultry environments" 2010 Poultry Science 21 (11 ): 2761-2766.
Stewart et al. "Growing Unculturable Bacteria" Journal of Bacteriology (2012) pp. 4151-4160.
Van Der Zee et al. "Conventional methods for the detection and isolation of *Salmonella enteritidis*," International Journal of Food and Microbiology, vol. 21, No. 1-2, (Jan. 1, 1994), pp. 41-46.
Vanderlinde "Microbiology of food and animal feeding stuffs: Horizontal method for the detection of *Salmonella* spp as 501310-2009," Approved Methods Manual, (Aug. 10, 2010), p. 1.
XLD AGAR (ISO) (9207), PI, (Dec. 1, 2008), XP055110702, Retrieved from internet, URL: http://www.neogen.com/Acumedia/pdf/Prodinfo/9207_PI.pdf.

\* cited by examiner

RAPID METHOD FOR DETECTION OF *SALMONELLA* LIVE VACCINE STRAINS

This continuation-in-part application claims the benefit of priority pursuant to 35 U.S.C. § 120 to U.S. patent application Ser. No. 14/161,117, filed Jan. 22, 2014, a U.S. Non-Provisional patent application that claims priority to U.S. Provisional Patent Application 61/927,401, filed Jan. 14, 2014 and Spanish Patent Application ES 201330064, filed Jan. 22, 2013, the content of each is which incorporated by reference in its entirety.

Pathogens can contaminate food or food animals during production, processing and preparation. Similarly, pathogens can contaminate water sources or seafood harvested from such contaminated waters. Human exposure to pathogens can cause illness, most often gastroenteritis, but also potentially more serious diseases such as salmonellosis and hepatitis A. Exposure to pathogens can occur either by direct contact with, or ingestion of, contaminated foods or water or indirectly based on cross-contamination. Even though the United States has one of the safest food supplies in the world, there are still millions of cases of foodborne illness each year.

Early and rapid detection of pathogen contamination is vital to prevent widespread outbreaks of illness and ensure the health of the public at large. During the past 25 years, pathogen assays that increase sensitiviety and specificity as well as decrease the time involved to perform these assays have been developed by experts in applied microbiology and microbiological analysis. Although there is no universally accepted definition for these so-called rapid assays, these methods are simply performed faster than the traditional ones, or are easier to implement, or are more sensitive and specific. Despite the name, currently available rapid assays for pathogen detection still require several days to complete the assay and determine whether a food or water supply is contaminated with a pathogen.

The main obstacles associated with reducing the time needed to conduct pathogen detection assays is the balance between the sensitivity, specificity, and lower limit of detection of the assay on one hand and having enough pathogen present to detect its presence above contaminating microorganisms and background noise.

To combat infections in poultry, livestock or humans, live vaccine strains have been created in order to elicit an immune response that creates protective antibodies agaisnt pathogenic *Salmonella* strains (or *Salmonella* field strains) that cause infections. Unlike the *Salmonella* field strains, the live vaccine strains are non-pathogenic. Plating and genotyping-based assays have been developed to detect the presence of *Salmonella* live vaccine strains. However, these assays are not only time consuming and, in the case of genotyping-based assays, require sophisticated equipment. In addition, current testing cannot distinguish between *Salmonella* field strains and live vaccine strains, which creates a problem for detection assays used to identify infectious *Salmonella* field strains, namely false positives due to the presence of non-infectious live vaccine strains. Thus, there is a need to develop detection assays that can identify and distinguish between field strains and live vaccine strains.

The present specification discloses a rapid method for the detection of live vaccine strains of pathogens which provides high sensitivity and specificity, a lower limit of detection, yet can be performed more quickly then currently available methods.

SUMMARY

Aspects of the present specification disclose a method of detecting a pathogen in a sample. In aspects, a method disclosed herein comprises the steps of a) incubation of the sample in a pre-enrichment comprising a low growth nutrient component, a growth inhibiting agent, and a surfactant with bacteriostatic or bactericidal action, wherein the incubation occurs at a specific temperature for a specific length of time; b) incubating an aliquot of pre-enrichment media from step (a) in an enrichment media, the enrichment media comprising a high growth nutrient component and a growth promoting agent, wherein the incubation occurs at a specific temperature for a specific length of time; and c) detecting the presence of absence of a pathogen by analyzing an aliquot of enrichment media from step (b).

Other aspects of the present specification disclose a method of detecting a *Salmonella* live vaccine strain in a sample. The method disclosed herein comprises: a) incubation of the sample in a first liquid pre-enrichment comprising 2 g/L to 6 g/L of a peptone, 0.5 g/L to 4.5 g/L Bile Salts, 0.5 g/L to 4.5 g/L Meat Extract, 0.5 g/L to 4.5 g/L of a first growth inhibiting agent, 0.5 g/L to 4.5 g/L of a second growth inhibiting agent, 0.001 g/L to 0.008 g/L of a third growth inhibiting agent, and 0.001 g/L to 0.008 g/L of a fourth growth inhibiting agent, wherein the incubation at about 34° C. to about 40° C. for about 5 hours to about 10 hours; b) incubating an aliquot of first pre-enrichment media from step (a) in a liquid enrichment media, the enrichment media comprising 6 g/L to 10 g/L of a peptone, 3 g/L to 7 g/L Bile Salts, 2 g/L to 6 g/L Meat Extract, 2 g/L to 6 g/L of a first growth inhibiting agent, 2 g/L to 6 g/L of a second growth inhibiting agent, 0.001 g/L to 0.008 g/L of a third growth inhibiting agent, and 0.001 g/L to 0.008 g/L of a fourth growth inhibiting agent, wherein the incubation at about 34° C. to about 45° C. for about 14 hours to about 20 hours; c) purifying the liquid enrichment medium or an aliquot thereof to increase concentration of the *Salmonella* live vaccine strain and/or decrease contaminants; d) incubating an aliquot of enrichment media from step (c) in a second liquid pre-enrichment comprising 2 g/L to 6 g/L of a peptone, 0.5 g/L to 4.5 g/L Bile Salts, 0.5 g/L to 4.5 g/L Meat Extract, 0.5 g/L to 4.5 g/L of a first growth inhibiting agent, 0.5 g/L to 4.5 g/L of a second growth inhibiting agent, 0.001 g/L to 0.008 g/L of a third growth inhibiting agent, and 0.001 g/L to 0.008 g/L of a fourth growth inhibiting agent, wherein the incubation at about 34° C. to about 45° C. for about 1 hours to about 5 hours; and e) detecting the presence of absence of a *Salmonella* live vaccine strain by analyzing an aliquot of the second liquid pre-enrichment media from step (d).

Other aspects of the present specification disclose a pathogen analysis kit. In aspects, pathogen analysis kit comprising a pre-enrichment media and an enrichment media. In other aspects, the pathogen analysis kit may further comprise detection solution. In yet other aspects, the pathogen analysis kit may further comprise an immunopurification reagent system. In yet other aspects, the pathogen analysis kit may further comprise a label or an insert providing instructions on how to use the kit.

Other aspects of the present specification disclose a *Salmonella* live vaccine analysis kit. In aspects, analysis kit comprising a pre-enrichment media and an enrichment media as disclosed herein. In other aspects, the analysis kit may further comprise detection solution. In yet other aspects, the analysis kit may further comprise an immunopurification reagent system. In yet other aspects, the analysis kit may further comprise a label or an insert providing instructions on how to use the kit.

DESCRIPTION

Figure 1:
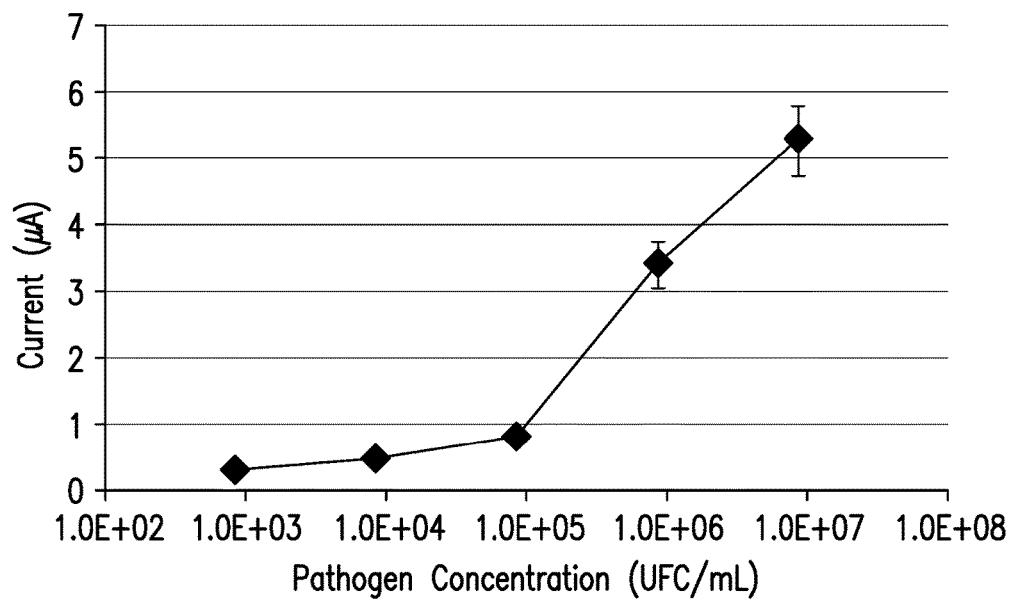
FIG. 1 shows a graph of the proportionality between different densities of bacterial population and the signal obtained chronoamperometric.

The present specification discloses a method of detecting a pathogen in a sample. The method comprises a pre-enrichment step and an enrichment step that use selective pre-growth and growth media. The combination of these steps, together with specific time and temperature conditions, progressively increases the population of the pathogen as well as an effective reduces the populations of unwanted organisms and/or other background noise which interferes with the detection of the pathogen. The selective increase of the pathogen population as well as the effectively removing unwanted organisms and/or other background noise allows for a more sensitive and precise detection of the pathogen then currently available methods. In addition, the method disclosed herein allows for a more rapid detection of a pathogen since it may be completed in about eight hours to about 30 hours; current pathogen detection methods require about 2 days to about 5 days to complete.

Aspect of the present specification disclose, in part, a pathogen. A pathogen refers to a microorganism that can cause disease in its host. Non-limiting examples of a pathogen include a prion, a virus, a bacterium, a fungus, a protazoan, a helimenth, and a parasite.

A prion is composed of a protein in a misfolded form. Prions reproduce by hijacking the functions of living cells and propagating a misfolded protein state by inducing existing, properly-folded proteins to convert into the disease-associated, prion form. As such, the prion acts as a template to guide the misfolding of more proteins into prion form. These newly formed prions can then go on to convert more proteins themselves, which triggers a chain reaction that produces large amounts of the prion form. Prions cause neurodegenerative disease by aggregating extracellularly within the central nervous system to form plaques known as amyloid, which disrupt the normal tissue structure. Prions are responsible for the transmissible spongiform encephalopathies in a variety of mammals, including bovine spongiform encephalopathy (BSE, also known as "mad cow disease") in cattle, scrapies in sheep and goats, and chronic wasting disease in deer. In humans, prions cause Creutzfeldt-Jakob disorders, Gerstmann-Sträussler-Scheinker syndrome, Fatal Familial Insomnia, and kuru.

A virus is a small infectious agent typically range between 20-300 nanometers in length that replicates only inside the living cells of other organisms. Virus particles (known as virions) consist of two or three parts: i) the genetic material made from either DNA or RNA, long molecules that carry genetic information; ii) a protein coat that protects these genes; and in some cases iii) an envelope of lipids that surrounds the protein coat when they are outside a cell. The shapes of viruses range from simple helical and icosahedral forms to more complex structures. The average virus is about one one-hundredth the size of the average bacterium. Viruses can infect all types of life forms, from animals and plants to bacteria and archaea. Non-limiting examples of pathogenic viruses belong to the families Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae.

A bacteria is a single-celled prokaryotic microorganism characterized by the lack of a membrane-bound nucleus and membrane-bound organelles and can have a cell wall (Gram positive) or lack one (Gram negative). Morphologically, bacteria can be divided into rod-shaped (*bacillus*), round (coccus), spiral (spirillum), and incomplete spiral (vibrios). Non-limiting examples of pathogenic bacteria belong to the genera *Bacillus, Bordetella, Borrelia, Brucella, Campylobacter, Chlamydia, Chlamydophila, Clostridium, Corynebacterium, Enterobacter, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* and *Yersinia.* Non-limiting examples of specific pathogenic bacterial species include a strain of *Bacillus anthracis*, a strain of a strain of *Bordetella pertussis*, a strain of a strain of *Borrelia burgdorferi*, a strain of a strain of *Brucella abortus*, a strain of a strain of *Brucella canis*, a strain of a strain of *Brucella melitensis*, a strain of a strain of *Brucella suis*, a strain of a strain of *Campylobacter jejuni*, a strain of *Chlamydia pneumonia*, a strain of *Chlamydia trachomatis*, a strain of *Chlamydophila psittaci*, a strain of *Clostridium botulinum*, a strain of *Clostridium difficile*, a strain of *Clostridium perfringens*, a strain of *Clostridium tetani*, a strain of *Corynebacterium diphtheria*, a strain of *Enterobacter sakazakii*, a strain of *Enterococcus faecalis*, a strain of *Enterococcus faecium*, a strain of *Escherichia coli*, a strain of *Francisella tularensis*, a strain of *Haemophilus influenza*, a strain of *Helicobacter pylori*, a strain of *Legionella pneumophila*, a strain of *Leptospira interrogans*, a strain of *Listeria monocytogenes*, a strain of *Mycobacterium leprae*, a strain of *Mycobacterium tuberculosis*, a strain of *Mycobacterium ulcerans*, a strain of *Mycoplasma pneumonia*, a strain of *Neisseria gonorrhoeae*, a strain of *Neisseria meningitides*, a strain of *Pseudomonas aeruginosa*, a strain of *Rickettsia rickettsia*, a strain of *Salmonella typhi* and *Salmonella typhimurium*, a strain of *Shigella sonnei*, a strain of *Staphylococcus aureus*, a strain of *Staphylococcus epidermidis*, a strain of *Staphylococcus saprophyticus*, a strain of *Streptococcus agalactiae*, a strain of *Streptococcus pneumonia*, a strain of *Streptococcus pyogenes*, a strain of *Treponema pallidum*, a strain of *Vibrio cholera*, a strain of *Yersinia enterocolitica*, and a strain of *Yersinia pestis*.

A bacterial strain can be a pathogenic strain or a non-pathogenic strain. A pathogenic bacterial strain is one that causes or facilitates a disease, infection or other adverse effect in a mammal. A pathogenic bacterial strain is considered to be an abnormal or infectious flora. A non-pathogenic bacterial strain is one that is considered harmless to a mammal because no appreciable disease, infection or other adverse effect is associated with the presence of the non-pathogenic bacterial strain in the mammal. A non-pathogenic bacterial strain is considered to be a benign or beneficial flora. A non-pathogenic bacterial strain includes a live vaccine bacterial strain. A live vaccine bacterial strain is typically an attenuated bacterial strain used to elicit an immune response that creates protective antibodies in an individual, such as poultry, livestock or humans, against pathogenic bacterial strains (or bacterial field strains) that cause infections. In an embodiment, live vaccine bacterial strain includes a *Salmonella* live vaccine strain. Examples of a *Salmonella* live vaccine bacterial strain include, without limitation, a VacT *Salmonella* live vaccine strain and VacE *Salmonella* live vaccine strain.

A fungus is a eukaryotic microorganism characterized by membrane-bound nucleus and organelles which lack chlorophyll have cell walls composed of chitin and reproduce by spores. Non-limiting examples of pathogenic fungi belong to the genera *Asperfillus, Canidia, Cryptococcus, Histoplasma, Pneumocystis,* and *Stachybotrys.* Non-limiting examples of specific pathogenic fungi species include a strain of *Aspergillus clavatus, Aspergillus fumigatus, Aspergillus flavus, Canidia albicans, Cryptococcus albidus, Cryptococcus gattii, Cryptococcus laurentii, Cryptococcus neoformans, Histoplasma capsulatum, Pneumocystis jirovecii, Pneumocystis carinii,* and *Stachybotrys chartarum.*

A protozoa is a eukaryotic single-cell microorganism characterized by membrane-bound nucleus and organelles which lack chlorophyll and a cell wall and are motile. Protozoa commonly range from 10 to 52 micrometers, but can grow as large as 1 mm. Non-limiting examples of pathogenic protozoa belong to the genera *Acanthamoeba, Balamuthia, Cryptosporidium, Dientamoeba, Endolimax, Entamoeba, Giardia, lodamoeba, Leishmania, Naegleria, Plasmodium, Sappinia, Toxoplasma, Trichomonas,* and *Trypanosoma.* Non-limiting examples of specific pathogenic protozoa species include a strain of *Acanthamoeba* spp., *Balamuthia mandrillaris, Cryptosporidium canis, Cryptosporidium felis, Cryptosporidium hominis, Cryptosporidium meleagridis, Cryptosporidium muris, Cryptosporidium parvum, Dientamoeba fragilis, Endolimax nana, Entamoeba dispar, Entamoeba hartmanni, Entamoeba histolytica, Entamoeba coli, Entamoeba moshkovskii, Giardia lamblia, lodamoeba butschlii, Leishmania aethiopica, Leishmania braziliensis, Leishmania chagasi, Leishmania donovani, Leishmania infantum, Leishmania major, Leishmania mexicana, Leishmania tropica, Naegleria fowleri, Plasmodium falciparum, Plasmodium knowlesi, Plasmodium malariae, Plasmodium ovale, Plasmodium vivax, Sappinia diploidea, Toxoplasma gondii, Trichomonas vaginalis, Trypanosoma brucei,* and *Trypanosoma cruzi.*

Aspect of the present specification disclose, in part, a sample. A variety of samples are useful in the methods disclosed herein. A sample refers to a biological matter that contains or potentially contains a pathogen. A sample encompasses but is not limited to a purified pathogen, a partially purified pathogen, a cell, a crude cell lysate, a partially purified cell lysate, a crude culture media, a partially purified culture media, a raw foodstuff, a partially-cooked foodstuff, a cooked foodstuff, a processed foodstuff; a dairy foodstuff, a beverage, an animal feed, a fecal sample, a vegetative sample, a soil sample, a water sample, a pond sediment, a human tissue sample, a raw livestock tissue sample, a processed livestock tissue sample, such as, e.g., leather.

Aspect of the present specification disclose, in part, a pre-enrichment step. A pre-enrichment step comprises incubating a sample disclosed herein in a pre-enrichment media for a defined time and at a defined temperature. A pre-enrichment media, also referred to as a pre-enrichment culture media is a buffered culture media that provides the nutrients necessary to sustain low-growth of the pathogen. In addition, a pre-enrichment media may also contain components which reduce or inhibit the growth of contaminating bacteria or other microorganisms. A pre-enrichment media comprises a low growth nutrient component, a surfactant, and optionally a growth inhibiting agent and/or a growth enhancing agent. In some embodiments, a method disclosed herein may use a first pre-enrichment media and a second pre-enrichment media. A first and second pre-enrichment media may comprises the same low growth nutrient component, surfactant, and optionally growth inhibiting agent and/or growth enhancing agent, i.e., the first and second pre-enrichment media will be of identical composition. In other embodiments, a first and second pre-enrichment media may comprises the same low growth nutrient component, surfactant, and optionally growth inhibiting agent and/or growth enhancing agent but in differing amount from one another. In other embodiments, a first pre-enrichment media may comprises different low growth nutrient component, surfactant, and optionally growth inhibiting agent and/or growth enhancing agent relative to a second pre-enrichment media.

A pre-enrichment media typically comprises a low growth nutrient component used as a source of proteins, amino acids and nitrogen. Either a single low growth nutrient component may comprise a pre-enrichment media disclosed herein, or a plurality of low growth nutrient components may comprise a pre-enrichment media disclosed herein.

A non-limiting example of a low growth nutrient component is a peptone, such as, e.g., a peptide from an animal source and a peptone from a plant source. A peptone from an animal source includes, without limitation, an acid casein peptone, a bacteriological peptone, a beef extract powder, a casein peptone, a casein cc peptone, a gelatin peptone, a meat peptone, a polypeptone proteose peptone, and a proteose peptone No 3. A peptone from a plant source includes, without limitation, a malt extract, a soya peptone, and a yeast extract.

Any concentration of low growth nutrient component may be used, with the proviso that the concentration is useful to practice the methods disclosed herein. In aspects of this embodiment, a low growth nutrient component may be used at a concentration of, e.g., about 1 g/L, about 2 g/L, about 3 g/L, about 4 g/L, about 5 g/L, about 6 g/L, about 7 g/L, about 8 g/L, about 9 g/L, about 10 g/L, about 11 g/L, about 12 g/L, about 13 g/L, about 14 g/L, or about 15 g/L. In other aspects of this embodiment, a low growth nutrient component may be used at a concentration of, e.g., at least 1 g/L, at least 2 g/L, at least 3 g/L, at least 4 g/L, at least 5 g/L, at least 6 g/L, at least 7 g/L, at least 8 g/L, at least 9 g/L, at least 10 g/L, at least 11 g/L, at least 12 g/L, at least 13 g/L, at least 14 g/L, or at least 15 g/L. In yet other aspects of this embodiment, a low growth nutrient component may be used at a concentration of, e.g., at most 1 g/L, at most 2 g/L, at most 3 g/L, at most 4 g/L, at most 5 g/L, at most 6 g/L, at most 7 g/L, at most 8 g/L, at most 9 g/L, at most 10 g/L, at most 11 g/L, at most 12 g/L, at most 13 g/L, at most 14 g/L, or at most 15 g/L.

In yet other aspects of this embodiment, a low growth nutrient component may be used at a concentration of between, e.g., about 1 g/L to 2 g/L, about 1 g/L to 3 g/L, about 1 g/L to 4 g/L, about 1 g/L to 5 g/L, about 1 g/L to 6 g/L, about 1 g/L to 7 g/L, about 1 g/L to 8 g/L, about 1 g/L to 9 g/L, about 1 g/L to 10 g/L, about 1 g/L to 11 g/L, about 1 g/L to 12 g/L, about 1 g/L to 13 g/L, about 1 g/L to 14 g/L, about 1 g/L to 15 g/L, about 2 g/L to 3 g/L, about 2 g/L to 4 g/L, about 2 g/L to 5 g/L, about 2 g/L to 6 g/L, about 2 g/L to 7 g/L, about 2 g/L to 8 g/L, about 2 g/L to 9 g/L, about 2 g/L to 10 g/L, about 2 g/L to 11 g/L, about 2 g/L to 12 g/L, about 2 g/L to 13 g/L, about 2 g/L to 14 g/L, about 2 g/L to 15 g/L, about 3 g/L to 4 g/L, about 3 g/L to 5 g/L, about 3 g/L to 6 g/L, about 3 g/L to 7 g/L, about 3 g/L to 8 g/L, about 3 g/L to 9 g/L, about 3 g/L to 10 g/L, about 3 g/L to 11 g/L, about 3 g/L to 12 g/L, about 3 g/L to 13 g/L, about 3 g/L to 14 g/L, about 3 g/L to 15 g/L, about 4 g/L to 5 g/L, about 4 g/L to 6 g/L, about 4 g/L to 7 g/L, about 4 g/L to 8 g/L, about 4 g/L to 9 g/L, about 4 g/L to 10 g/L, about 4 g/L to 11 g/L, about 4 g/L to 12 g/L, about 4 g/L to 13 g/L, about 4 g/L to 14 g/L, about 4 g/L to 15 g/L, about 5 g/L to 6 g/L, about 5 g/L to 7 g/L, about 5 g/L to 8 g/L, about 5 g/L to 9 g/L, about 5 g/L to 10 g/L, about 5 g/L to 11 g/L, about 5 g/L to 12 g/L, about 5 g/L to 13 g/L, about 5 g/L to 14 g/L, about 5 g/L to 15 g/L, about 6 g/L to 7 g/L, about 6 g/L to 8 g/L, about 6 g/L to 9 g/L, about 6 g/L to 10 g/L, about 6 g/L to 11 g/L, about 6 g/L to 12 g/L, about 6 g/L to 13 g/L, about 6 g/L to 14 g/L, about 6 g/L to 15 g/L, about 7 g/L to 8 g/L, about 7 g/L to 9 g/L, about 7 g/L to 10 g/L, about 7 g/L to 11 g/L, about 7 g/L to 12 g/L, about 7 g/L to 13 g/L, about 7 g/L to 14 g/L, about 7 g/L to 15 g/L, about 8 g/L to 9 g/L, about 8 g/L to 10 g/L, about 8 g/L to 11 g/L, about 8 g/L to 12 g/L, about 8 g/L to 13 g/L, about 8 g/L to 14 g/L, about 8 g/L to 15 g/L, about 9 g/L to 10 g/L, about 9 g/L to 11 g/L, about 9 g/L to 12 g/L, about 9 g/L to 13 g/L, about 9 g/L to 14 g/L, about 9 g/L to 15 g/L, about 10 g/L to 11 g/L, about 10 g/L to 12 g/L, about 10 g/L to 13 g/L, about 10 g/L to 14 g/L, about 10 g/L to 15 g/L, about 11 g/L to 12 g/L, about 11 g/L to 13 g/L, about 11 g/L to 14 g/L, about 11 g/L to 15 g/L, about 12 g/L to 13 g/L, about 12 g/L to 14 g/L, about 12 g/L to 15 g/L, about 13 g/L to 14 g/L, about 13 g/L to 15 g/L, or about 14 g/L to 15 g/L.

A pre-enrichment media may also comprises a surfactant. Surfactants are compounds that lower the surface tension of a liquid, allowing easier spreading, and lowering of the interfacial tension between two liquids, or between a liquid and a solid. Either a single surfactant may comprise a pre-enrichment media disclosed herein, or a plurality of surfactants may comprise a pre-enrichment media disclosed herein. A surfactant disclosed herein provides bacteriostatic and bactericide action that retards or prevents growth of unwanted organisms contained in a sample disclosed herein. As non-limiting examples, a surfactant may retard or prevent growth of unwanted bacterial cells by disrupting the mechanisms of action of adsorption on the surface, interfering with the osmotic balance, preventing the intake of nutrients, denaturing proteins, inhibiting enzyme activity, and/or damaging the cell membrane.

Useful surfactants, include, without limitation, ionic surfactants, zwitterionic (amphoteric) surfactants, non-ionic surfactants, or any combination therein. The surfactant used in a method disclosed herein can be varied as appropriate by one skilled in the art and generally depends, in part, on the particular pre-enrichment media being used, the pathogen being detected, and/or the particular unwanted bacteria being removed. Ionic surfactants include anionic surfactants based on permanent (sulfate, sulfonate, phosphate) or pH dependent (carboxylate) anions. Anionic surfactants include, without limitation, alkyl sulfates like ammonium lauryl sulfate and sodium lauryl sulfate (SDS); alkyl ether sulfates like sodium laureth sulfate and sodium myreth sulfate; docusates like dioctyl sodium sulfosuccinate; tetradecyl sodium dodecyl sulfate; 7-ethyl-2-methyl-4-undecyl sodium sulphate; octadecyl sulphate; sulfonate fluorosurfactants like perfluorooctanesulfonate (PFOS) and perfluorobutanesulfonate; alkyl benzene sulfonates; alkyl aryl ether phosphates; alkyl ether phosphates; alkyl carboxylates like fatty acid salts and sodium stearate; sodium lauroyl sarcosinate; and carboxylate fluorosurfactants like perfluorononanoate and perfluorooctanoate.

Ionic surfactants also include cationic surfactants based on permanent or pH dependent cations. Cationic surfactants include, without limitation, alkyltrimethylammonium salts like cetyl trimethylammonium bromide (CTAB) and cetyl trimethylammonium chloride (CTAC); cetylpyridinium chloride (CPC); polyethoxylated tallow amine (POEA); benzalkonium chloride (BAC); benzethonium chloride (BZT); 5-Bromo-5-nitro-1,3-dioxane; dimethyldioctadecylammonium chloride; and dioctadecyldimethylammonium bromide (DODAB), as well as pH-dependent primary, secondary or tertiary amines like surfactants where the primary amines become positively charged at pH greater than 10, or the secondary amines become charged at pH less than 4, like octenidine dihydrochloride.

Zwitterionic surfactants are based on primary, secondary or tertiary amines or quaternary ammonium cation with a sulfonate, a carboxylate, or a phosphate. Zwitterionic surfactants include, without limitation, 3-[(3-Cholamidopropyl)dimethylammonio]-1-propanesulfonate (CHAPS); sultaines like cocamidopropyl hydroxysultaine; betaines like cocamidopropyl betaine; or lecithins.

Non-ionic surfactants are less denaturing and as such are useful to solubilize membrane proteins and lipids while retaining protein-protein interactions. Non-limiting examples of surfactants include polyoxyethylene glycol sorbitan alkyl esters like polysorbate 20 sorbitan monooleate (TWEEN® 20), polysorbate 40 sorbitan monooleate (TWEEN® 40), polysorbate 60 sorbitan monooleate (TWEEN® 60), polysorbate 61 sorbitan monooleate (TWEEN® 61), polysorbate 65 sorbitan monooleate (TWEEN® 65), polysorbate 80 sorbitan monooleate (TWEEN® 80), and polysorbate 81 sorbitan monooleate (TWEEN® 81); poloxamers (polyethylene-polypropylene copolymers), like Poloxamer 124 (PLURONIC® L44), Poloxamer 181 (PLURONIC® L61), Poloxamer 182 (PLURONIC® L62), Poloxamer 184 (PLURONIC® L64), Poloxamer 188 (PLURONIC® F68), Poloxamer 237 (PLURONIC® F87), Poloxamer 338 (PLURONIC® L108), and Poloxamer 407 (PLURONIC® F127); alkyl phenol polyglycol ethers; polyethylene glycol alkyl aryl ethers; polyoxyethylene glycol alkyl ethers, like octaethylene glycol monododecyl ether, pentaethylene glycol monododecyl ether, BRIJ® 30, and BRIJ® 35; 2-dodecoxyethanol (LUBROL®-PX); polyoxyethylene glycol octylphenol ethers like polyoxyethylene (4-5) p-t-octyl phenol (TRITON® X-45) and polyoxyethylene octyl phenyl ether (TRITON® X-100); nonylphenol ethoxylates like Nonoxynol-4 (TERGITOL™ NP-4), Nonoxynol-6 (TERGITOL™ NP-6), Nonoxynol-7 (TERGITOL™ NP-7), Nonoxynol-8 (TERGITOL™ NP-8), Nonoxynol-9 (TERGITOL™ NP-9), Nonoxynol-10 (TERGITOL™ NP-10), Nonoxynol-11 (TERGI- TOL™ NP-11), Nonoxynol-12 (TERGITOL™ NP-12), Nonoxynol-13 (TERGITOL™ NP-13), Nonoxynol-15 (TERGITOL™ NP-15), Nonoxynol-30 (TERGITOL™ NP-30), Nonoxynol-40 (TERGITOL™ NP-40), Nonoxynol-50 (TERGITOL™ NP-50), Nonoxynol-55 (TERGITOL™ NP-55), and Nonoxynol-70 (TERGITOL™ NP-70); phenoxypolyethoxylethanols like nonyl phenoxypolyethoxylethanol and octyl phenoxypolyethoxylethanol; glucoside alkyl ethers like octyl glucopyranoside; maltoside alkyl ethers like dodecyl maltopyranoside; thioglucoside alkyl ethers like heptyl thioglucopyranoside; digitonins; glycerol alkyl esters like glyceryl laurate; alkyl aryl polyether sulfates; alcohol sulfonates; sorbitan alkyl esters; cocamide ethanolamines like cocamide monoethanolamine and cocamide diethanolamine; sucrose monolaurate; dodecyl dimethylamine oxide, and sodium cholate. Other non-limiting examples of surfactants useful in the methods disclosed herein can be found in, e.g., Winslow, et al., Methods and Compositions for Simultaneously Isolating Hemoglobin from Red Blood Cells and Inactivating Viruses, U.S. 2008/0138790; Pharmaceutical Dosage Forms and Drug Delivery Systems (Howard C. Ansel et al., eds., Lippincott Williams & Wilkins Publishers, 7th ed. 1999); Remington: The Science and Practice of Pharmacy (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003), each of which is hereby incorporated by reference in its entirety.

Any concentration of surfactant may be used, with the proviso that the concentration is useful to practice the methods disclosed herein. In aspects of this embodiment, a surfactant may be used at a concentration of, e.g., about 0.01% (v/v), about 0.05% (v/v), about 0.075% (v/v), about 0.1% (v/v), about 0.2% (v/v), about 0.3% (v/v), about 0.4% (v/v), about 0.5% (v/v), about 0.6% (v/v), about 0.7% (v/v), about 0.8% (v/v), about 0.9% (v/v), about 1.0% (v/v), about 2.0% (v/v), about 3.0% (v/v), about 4.0% (v/v), about 5.0% (v/v), about 6.0% (v/v), about 7.0% (v/v), about 8.0% (v/v), about 9.0% (v/v), or about 10.0% (v/v). In other aspects of this embodiment, a surfactant may be used at a concentration of, e.g., at least 0.01% (v/v), at least 0.05% (v/v), at least 0.075% (v/v), at least 0.1% (v/v), at least 0.25% (v/v), at least 0.5% (v/v), at least 0.75% (v/v), at least 1.0% (v/v), at least 2.5% (v/v), at least 5.0% (v/v), at least 7.5% (v/v), or at least 10.0% (v/v). In yet other aspects of this embodiment, a surfactant may be used at a concentration of, e.g., at most 0.01% (v/v), at most 0.05% (v/v), at most 0.075% (v/v), at most 0.1% (v/v), at most 0.25% (v/v), at most 0.5% (v/v), at most 0.75% (v/v), at most 1.0% (v/v), at most 2.5% (v/v), at most 5.0% (v/v), at most 7.5% (v/v), or at most 10.0% (v/v).

In still other aspects of this embodiment, a surfactant may be used at a concentration of between, e.g., about 0.01% (v/v) to about 0.05% (v/v), about 0.01% (v/v) to about 0.1% (v/v), about 0.01% (v/v) to about 0.5% (v/v), about 0.01% (v/v) to about 1.0% (v/v), about 0.01% (v/v) to about 2.0% (v/v), about 0.01% (v/v) to about 3.0% (v/v), about 0.01% (v/v) to about 4.0% (v/v), about 0.01% (v/v) to about 5.0% (v/v), about 0.05% (v/v) to about 0.1% (v/v), about 0.05% (v/v) to about 0.5% (v/v), about 0.05% (v/v) to about 1.0% (v/v), about 0.05% (v/v) to about 2.0% (v/v), about 0.05% (v/v) to about 3.0% (v/v), about 0.05% (v/v) to about 4.0% (v/v), about 0.05% (v/v) to about 5.0% (v/v), about 0.1% (v/v) to about 0.5% (v/v), about 0.1% (v/v) to about 1.0% (v/v), about 0.1% (v/v) to about 2.0% (v/v), about 0.2% (v/v) to about 0.5% (v/v), about 0.2% (v/v) to about 1.0% (v/v), about 0.2% (v/v) to about 2.0% (v/v), about 0.2% (v/v) to about 3.0% (v/v), about 0.2% (v/v) to about 4.0% (v/v), about 0.2% (v/v) to about 5.0% (v/v), about 0.5% (v/v) to about 1.0% (v/v), about 0.5% (v/v) to about 2.0% (v/v), about 0.5% (v/v) to about 3.0% (v/v), about 0.5% (v/v) to about 4.0% (v/v), about 0.5% (v/v) to about 5.0% (v/v), about 0.5% (v/v) to about 6.0% (v/v), about 0.5% (v/v) to about 7.0% (v/v), about 0.5% (v/v) to about 8.0% (v/v), about 0.5% (v/v) to about 9.0% (v/v), about 0.5% (v/v) to about 10.0% (v/v), about 1.0% (v/v) to about 2.0% (v/v), about 1.0% (v/v) to about 3.0% (v/v), about 1.0% (v/v) to about 4.0% (v/v), about 1.0% (v/v) to about 5.0% (v/v), about 1.0% (v/v) to about 6.0% (v/v), about 1.0% (v/v) to about 7.0% (v/v), about 1.0% (v/v) to about 8.0% (v/v), about 1.0% (v/v) to about 9.0% (v/v), or about 1.0% (v/v) to about 10.0% (v/v).

In aspects of this embodiment, the surfactant may be used at a concentration of, e.g., about 0.001 g/L, about 0.002 g/L, about 0.003 g/L, about 0.004 g/L, about 0.005 g/L, about 0.006 g/L, about 0.007 g/L, about 0.008 g/L, about 0.009 g/L, about 0.01 g/L, about 0.02 g/L, about 0.03 g/L, about 0.04 g/L, about 0.05 g/L, about 0.06 g/L, about 0.07 g/L, about 0.08 g/L, about 0.09 g/L, or about 0.1 g/L. In other aspects of this embodiment, the surfactant may be used at a concentration of, e.g., at least 0.001 g/L, at least 0.002 g/L, at least 0.003 g/L, at least 0.004 g/L, at least 0.005 g/L, at least 0.006 g/L, at least 0.007 g/L, at least 0.008 g/L, at least 0.009 g/L, at least 0.01 g/L, at least 0.02 g/L, at least 0.03 g/L, at least 0.04 g/L, at least 0.05 g/L, at least 0.06 g/L, at least 0.07 g/L, at least 0.08 g/L, at least 0.09 g/L, or at least 0.1 g/L. In yet other aspects of this embodiment, the surfactant may be used at a concentration of, e.g., at most 0.001 g/L, at most 0.002 g/L, at most 0.003 g/L, at most 0.004 g/L, at most 0.005 g/L, at most 0.006 g/L, at most 0.007 g/L, at most 0.008 g/L, at most 0.009 g/L, at most 0.01 g/L, at most 0.02 g/L, at most 0.03 g/L, at most 0.04 g/L, at most 0.05 g/L, at most 0.06 g/L, at most 0.07 g/L, at most 0.08 g/L, at most 0.09 g/L, or at most 0.1 g/L.

In still other aspects of this embodiment, the surfactant may be used at a concentration of, e.g., about 0.001 g/L to about 0.005 g/L, about 0.001 g/L to about 0.006 g/L, about 0.001 g/L to about 0.007 g/L, about 0.001 g/L to about 0.008 g/L, about 0.001 g/L to about 0.009 g/L, about 0.001 g/L to about 0.01 g/L, about 0.001 g/L to about 0.02 g/L, about 0.001 g/L to about 0.03 g/L, about 0.001 g/L to about 0.04 g/L, about 0.001 g/L to about 0.05 g/L, about 0.001 g/L to about 0.06 g/L, about 0.001 g/L to about 0.07 g/L, about 0.001 g/L to about 0.08 g/L, about 0.001 g/L to about 0.09 g/L, about 0.001 g/L to about 0.1 g/L, about 0.005 g/L to about 0.01 g/L, about 0.005 g/L to about 0.02 g/L, about 0.005 g/L to about 0.03 g/L, about 0.005 g/L to about 0.04 g/L, about 0.005 g/L to about 0.05 g/L, about 0.005 g/L to about 0.06 g/L, about 0.005 g/L to about 0.07 g/L, about 0.005 g/L to about 0.08 g/L, about 0.005 g/L to about 0.09 g/L, about 0.005 g/L to about 0.1 g/L, about 0.01 g/L to about 0.05 g/L, about 0.01 g/L to about 0.06 g/L, about 0.01 g/L to about 0.07 g/L, about 0.01 g/L to about 0.08 g/L, about 0.01 g/L to about 0.09 g/L, about 0.01 g/L to about 0.1 g/L, or about 0.05 g/L to about 0.1 g/L.

A pre-enrichment media may optionally comprises a growth inhibiting agent. A growth inhibiting agent typically comprises a component that reduces or inhibits the growth of contaminating bacteria or other contaminating microorganisms. In addition, a growth inhibiting agent may not affect the growth of a pathogen of interest or affects it to a lesser extent that the contaminating bacteria or other contaminating microorganisms. Either a single growth inhibiting agent may comprise a pre-enrichment media disclosed herein, or a plurality of growth inhibiting agents may comprise a pre-enrichment media disclosed herein. Non-limiting examples of a growth inhibiting agent include an anti-microbial compound, an iodine compound, a magnesium compound, and a triarylmethane dye.

An anti-microbial compound is one that is antagonistic to the growth of a microorganism. These compounds can be divided into two broad categories of microbicidal agents which kill a microorganism and microbiostatic agents which slow down or stall the growth of a microorganism. An anti-microbial compound is commonly classified based on its mechanism of action, chemical structure, or spectrum of activity. Most target bacterial functions or growth processes. Those that target the bacterial cell wall (penicillins and cephalosporins) or the cell membrane (polymyxins), or interfere with essential bacterial enzymes (rifamycins, lipiarmycins, quinolones, and sulfonamides) have bactericidal activities. Those that target protein synthesis (macrolides, lincosamides and tetracyclines) are usually bacteriostatic (with the exception of bactericidal aminoglycosides). Further categorization is based on their target specificity. "Narrow-spectrum" antibacterial antibiotics target specific types of bacteria, such as Gram-negative or Gram-positive bacteria, whereas broad-spectrum antibiotics affect a wide range of bacteria. An anti-microbial compound includes, without limitation, an aminocoumarin, an aminoglycoside, an ansamycin, a carbacephem, a carbapenen, a cephalosporin, a cyclic lipopeptide, a glycopeptide, a glycylcycline, a lincosamide, a lipiamycin, a lipopeptide, a macrolide, a monobactam, a nitrofuran, an oxazolidonome, a penicillin, a qunolones, a sulfonamide, and a tetracycline. Non-limiting examples of an aminocoumarin include Novobiocin, Albamycin, Couermycin and Clorobiocin.

An iodine compound combines with amino acids like tyrosine or histidine by a simple chemical reaction that denatures proteins having these amino acids exposed to the extra-cellular environment. Non-limiting examples of an iodine compound include iodine and potassium iodine.

A magnesium compound known to have anti-bacterial activity. In aspects of this embodiment, magnesium is magnesium chloride and magnesium sulfate.

A triarylmethane dye is a group of synthetic organic compounds containing triphenylmethane backbones that produce an intense, pH-dependent color. Triarylmethane dyes can be grouped into families according to the nature of the substituents on the aryl groups. Methyl violet dyes have dimethylamino groups at the p-positions of two aryl groups and include, without limitation, methyl violet 2B, methyl violet 6B, and methyl violet 10B. Fuchsine dyes have amine ($NH_2$ or NHMe) functional groups at the p-positions of each aryl group and include, without limitation, pararosaniline, fuchsine, new fuchsine, fuchsin basic violet, and fuchine acid. Phenol dyes have hydroxyl groups at the p positions of each aryl group and include, without limitation, phenol red, chlorophenol red, and cresol red. Malachite green dyes are related to the methyl violet dyes, except that they contain one phenyl ($C_6H_5$) group and include, without limitation, malachite green and brilliant green. A triarylmethane dye includes, without limitation, aluminon, aniline Blue WS, aurin, aurintricarboxylic acid, brilliant blue FCF, brilliant green, bromocresol green, bromocresol purple, bromophenol blue, bromopyrogallol red, bromothymol blue, bromsulphthalein, chlorophenol red, coomassie brilliant blue, cresol red, crystal violet, crystal violet lactone, ethyl green, fast green FCF, fluoran, fuchsine, fuchsine acid, gentian, green S, light green SF yellowish, malachite green, methyl blue, methyl violet, new fuchsine, pararosaniline, patent blue V, phenol red, phenolphthalein, rose bengal, thymolphthalein, victoria blue BO, water blue, xylene cyanol, and xylenol orange.

Any concentration of growth inhibiting agent may be used, with the proviso that the concentration is useful to practice the methods disclosed herein. In aspects of this embodiment, a growth inhibiting agent may be used at a concentration of, e.g., about 0.01% (v/v), about 0.05% (v/v), about 0.075% (v/v), about 0.1% (v/v), about 0.2% (v/v), about 0.3% (v/v), about 0.4% (v/v), about 0.5% (v/v), about 0.6% (v/v), about 0.7% (v/v), about 0.8% (v/v), about 0.9% (v/v), about 1.0% (v/v), about 2.0% (v/v), about 3.0% (v/v), about 4.0% (v/v), about 5.0% (v/v), about 6.0% (v/v), about 7.0% (v/v), about 8.0% (v/v), about 9.0% (v/v), or about 10.0% (v/v). In other aspects of this embodiment, a growth inhibiting agent may be used at a concentration of, e.g., at least 0.01% (v/v), at least 0.05% (v/v), at least 0.075% (v/v), at least 0.1% (v/v), at least 0.25% (v/v), at least 0.5% (v/v), at least 0.75% (v/v), at least 1.0% (v/v), at least 2.5% (v/v), at least 5.0% (v/v), at least 7.5% (v/v), or at least 10.0% (v/v). In yet other aspects of this embodiment, a growth inhibiting agent may be used at a concentration of, e.g., at most 0.01% (v/v), at most 0.05% (v/v), at most 0.075% (v/v), at most 0.1% (v/v), at most 0.25% (v/v), at most 0.5% (v/v), at most 0.75% (v/v), at most 1.0% (v/v), at most 2.5% (v/v), at most 5.0% (v/v), at most 7.5% (v/v), or at most 10.0% (v/v).

In still other aspects of this embodiment, a growth inhibiting agent may be used at a concentration of between, e.g., about 0.01% (v/v) to about 0.05% (v/v), about 0.01% (v/v) to about 0.1% (v/v), about 0.01% (v/v) to about 0.5% (v/v), about 0.01% (v/v) to about 1.0% (v/v), about 0.01% (v/v) to about 2.0% (v/v), about 0.01% (v/v) to about 3.0% (v/v), about 0.01% (v/v) to about 4.0% (v/v), about 0.01% (v/v) to about 5.0% (v/v), about 0.05% (v/v) to about 0.1% (v/v), about 0.05% (v/v) to about 0.5% (v/v), about 0.05% (v/v) to about 1.0% (v/v), about 0.05% (v/v) to about 2.0% (v/v), about 0.05% (v/v) to about 3.0% (v/v), about 0.05% (v/v) to about 4.0% (v/v), about 0.05% (v/v) to about 5.0% (v/v), about 0.1% (v/v) to about 0.5% (v/v), about 0.1% (v/v) to about 1.0% (v/v), about 0.1% (v/v) to about 2.0% (v/v), about 0.2% (v/v) to about 0.5% (v/v), about 0.2% (v/v) to about 1.0% (v/v), about 0.2% (v/v) to about 2.0% (v/v), about 0.2% (v/v) to about 3.0% (v/v), about 0.2% (v/v) to about 4.0% (v/v), about 0.2% (v/v) to about 5.0% (v/v), about 0.5% (v/v) to about 1.0% (v/v), about 0.5% (v/v) to about 2.0% (v/v), about 0.5% (v/v) to about 3.0% (v/v), about 0.5% (v/v) to about 4.0% (v/v), about 0.5% (v/v) to about 5.0% (v/v), about 0.5% (v/v) to about 6.0% (v/v), about 0.5% (v/v) to about 7.0% (v/v), about 0.5% (v/v) to about 8.0% (v/v), about 0.5% (v/v) to about 9.0% (v/v), about 0.5% (v/v) to about 10.0% (v/v), about 1.0% (v/v) to about 2.0% (v/v), about 1.0% (v/v) to about 3.0% (v/v), about 1.0% (v/v) to about 4.0% (v/v), about 1.0% (v/v) to about 5.0% (v/v), about 1.0% (v/v) to about 6.0% (v/v), about 1.0% (v/v) to about 7.0% (v/v), about 1.0% (v/v) to about 8.0% (v/v), about 1.0% (v/v) to about 9.0% (v/v), or about 1.0% (v/v) to about 10.0% (v/v).

A pre-enrichment media may optionally comprises a growth enhancing agent. A growth enhancing agent promotes rapid growth of a pathogen by reducing the lag phase in culture media, thereby reactivating dormant pathogen.

Non-limiting examples of a growth enhancing agent include a siderophore. A siderophore is a high-affinity iron chelating compound that acts to sequester and solubilize the iron. These compounds are important to a pathogen for its acquisition of iron in order to maintain cellular respiration and DNA synthesis. This is because under most culture environment, the amount of free iron (approximately $1\times10^{-9}$ M) is below the concentration required by most bacterial pathogens for growth. Non-limiting examples of a siderophore include Aerobactin, Alcaligin, Azotobactin, Bacillibactin, Desferrioxamine B, Desferrioxamine E, Enterobactin, Ferrichrome, Ferrioxiamina-B, Ferrioxiamina-E, Fusarinine C, Mycobactin, Ornibactin, Petrobactin, Pyoverdine, Pyochelin, Salmochelin, Staphyloferring A, Vibriobactin, and Yersiniabactin.

Any concentration of growth enhancing agent may be used, with the proviso that the concentration is useful to practice the methods disclosed herein. In aspects of this embodiment, a growth enhancing agent may be used at a concentration of, e.g., about 0.01 µM, about 0.05 µM, about 0.075 µM, about 0.1 µM, about 0.2 µM, about 0.3 µM, about 0.4 µM, about 0.5 µM, about 0.6 µM, about 0.7 µM, about 0.8 µM, about 0.9 µM, about 1.0 µM, about 2.0 µM, about 3.0 µM, about 4.0 µM, about 5.0 µM, about 6.0 µM, about 7.0 µM, about 8.0 µM, about 9.0 µM, or about 10.0% (v/v). In other aspects of this embodiment, a growth enhancing agent may be used at a concentration of, e.g., at least 0.01 µM, at least 0.05 µM, at least 0.075 µM, at least 0.1 µM, at least 0.25 µM, at least 0.5 µM, at least 0.75 µM, at least 1.0 µM, at least 2.5 µM, at least 5.0 µM, at least 7.5 µM, or at least 10.0% (v/v). In yet other aspects of this embodiment, a growth enhancing agent may be used at a concentration of, e.g., at most 0.01 µM, at most 0.05 µM, at most 0.075 µM, at most 0.1 µM, at most 0.25 µM, at most 0.5 µM, at most 0.75 µM, at most 1.0 µM, at most 2.5 µM, at most 5.0 µM, at most 7.5 µM, or at most 10.0 µM In still other aspects of this embodiment, a growth enhancing agent may be used at a concentration of between, e.g., about 0.01% (v/v) to about 0.05 µM, about 0.01% (v/v) to about 0.1 µM, about 0.01% (v/v) to about 0.5 µM, about 0.01% (v/v) to about 1.0 µM, about 0.01% (v/v) to about 2.0 µM, about 0.01% (v/v) to about 3.0 µM, about 0.01% (v/v) to about 4.0 µM, about 0.01% (v/v) to about 5.0 µM, about 0.05% (v/v) to about 0.1 µM, about 0.05% (v/v) to about 0.5 µM, about 0.05% (v/v) to about 1.0 µM, about 0.05% (v/v) to about 2.0 µM, about 0.05% (v/v) to about 3.0 µM, about 0.05% (v/v) to about 4.0 µM, about 0.05% (v/v) to about 5.0 µM, about 0.1% (v/v) to about 0.5 µM, about 0.1% (v/v) to about 1.0 µM, about 0.1% (v/v) to about 2.0 µM, about 0.2% (v/v) to about 0.5 µM, about 0.2% (v/v) to about 1.0 µM, about 0.2% (v/v) to about 2.0 µM, about 0.2% (v/v) to about 3.0 µM, about 0.2% (v/v) to about 4.0 µM, about 0.2% (v/v) to about 5.0 µM, about 0.5% (v/v) to about 1.0 µM, about 0.5% (v/v) to about 2.0 µM, about 0.5% (v/v) to about 3.0 µM, about 0.5% (v/v) to about 4.0 µM, about 0.5% (v/v) to about 5.0 µM, about 0.5% (v/v) to about 6.0 µM, about 0.5% (v/v) to about 7.0 µM, about 0.5% (v/v) to about 8.0 µM, about 0.5% (v/v) to about 9.0 µM, about 0.5% (v/v) to about 10.0 µM, about 1.0% (v/v) to about 2.0 µM, about 1.0% (v/v) to about 3.0 µM, about 1.0% (v/v) to about 4.0 µM, about 1.0% (v/v) to about 5.0 µM, about 1.0% (v/v) to about 6.0 µM, about 1.0% (v/v) to about 7.0 µM, about 1.0% (v/v) to about 8.0 µM, about 1.0% (v/v) to about 9.0 µM, or about 1.0% (v/v) to about 10.0 µM).

In an embodiment, a pre-enrichment media comprises 2 g/L to 6 g/L of a peptone, 0.5 g/L to 4.5 g/L Bile Salts, 0.5 g/L to 4.5 g/L Meat Extract, 0.5 g/L to 4.5 g/L of a first growth inhibiting agent, 0.5 g/L to 4.5 g/L of a second growth inhibiting agent, 0.001 g/L to 0.008 g/L of a third growth inhibiting agent, and 0.001 g/L to 0.008 g/L of a fourth growth inhibiting agent. In aspects of this embodiment, a pre-enrichment media comprises 2 g/L to 6 g/L of a Caseine peptone, 0.5 g/L to 4.5 g/L of Bile Salts, 0.5 g/L to 4.5 g/L of Meat Extract, 0.5 g/L to 4.5 g/L of a first iodine compound, 0.5 g/L to 4.5 g/L of a second iodine compound, 0.001 g/L to 0.008 g/L of an aminocoumarin antibiotic, and 0.001 g/L to 0.008 g/L of a triarylmethane dye. In still other aspects of this embodiment, a pre-enrichment media comprises 2 g/L to 6 g/L of a Caseine peptone, 0.5 g/L to 4.5 g/L of Bile Salts, 0.5 g/L to 4.5 g/L of Meat Extract, 0.5 g/L to 4.5 g/L of a Iodine, 0.5 g/L to 4.5 g/L of a Potassium Iodide, 0.001 g/L to 0.008 g/L of Novobiocin, and 0.001 g/L to 0.008 g/L of Brilliant Green.

In an embodiment, a pre-enrichment media comprises 3 g/L to 5 g/L of a peptone, 1.5 g/L to 3.5 g/L Bile Salts, 1 g/L to 3 g/L Meat Extract, 1 g/L to 3 g/L of a first growth inhibiting agent, 1 g/L to 3 g/L of a second growth inhibiting agent, 0.002 g/L to 0.006 g/L of a third growth inhibiting agent, and 0.002 g/L to 0.006 g/L of a fourth growth inhibiting agent. In aspects of this embodiment, a pre-enrichment media comprises 3 g/L to 5 g/L of a Caseine peptone, 1.5 g/L to 3.5 g/L of Bile Salts, 1 g/L to 3 g/L of Meat Extract, 1 g/L to 3 g/L of a first iodine compound, 1 g/L to 3 g/L of a second iodine compound, 0.002 g/L to 0.006 g/L of an aminocoumarin antibiotic, and 0.002 g/L to 0.006 g/L of a triarylmethane dye. In still other aspects of this embodiment, a pre-enrichment media comprises 3 g/L to 5 g/L of a Caseine peptone, 1.5 g/L to 3.5 g/L of Bile Salts, 1 g/L to 3 g/L g/L of Meat Extract, 1 g/L to 3 g/L of a Iodine, 1 g/L to 3 g/L of a Potassium Iodide, 0.002 g/L to 0.006 g/L of Novobiocin, and 0.002 g/L to 0.006 g/L of Brilliant Green.

In an embodiment, a pre-enrichment media comprises 4 g/L to 4.6 g/L of a peptone, 2.1 g/L to 2.7 g/L Bile Salts, 1.8 g/L to 2.4 g/L Meat Extract, 1.7 g/L to 2.3 g/L of a first growth inhibiting agent, 1.7 g/L to 2.3 g/L of a second growth inhibiting agent, 0.003 g/L to 0.005 g/L of a third growth inhibiting agent, and 0.003 g/L to 0.005 g/L of a fourth growth inhibiting agent. In aspects of this embodiment, a pre-enrichment media comprises 4 g/L to 4.6 g/L of a Caseine peptone, 2.1 g/L to 2.7 g/L of Bile Salts, 1.8 g/L to 2.4 g/L of Meat Extract, 1.7 g/L to 2.3 g/L of a first iodine compound, 1.7 g/L to 2.3 g/L of a second iodine compound, 0.003 g/L to 0.005 g/L of an aminocoumarin antibiotic, and 0.003 g/L to 0.005 g/L of a triarylmethane dye. In still other aspects of this embodiment, a pre-enrichment media comprises 4 g/L to 4.6 g/L of a Caseine peptone, 2.1 g/L to 2.7 g/L of Bile Salts, 1.8 g/L to 2.4 g/L of Meat Extract, 1.7 g/L to 2.3 g/L of a Iodine, 1.7 g/L to 2.3 g/L of a Potassium Iodide, 0.003 g/L to 0.005 g/L of Novobiocin, and 0.003 g/L to 0.005 g/L of Brilliant Green.

In an embodiment, a pre-enrichment media comprises 4.3 g/L of a peptone, 2.4 g/L Bile Salts, 2.1 g/L Meat Extract, 2 g/L of a first growth inhibiting agent, 2 g/L of a second growth inhibiting agent, 0.004 g/L of a third growth inhibiting agent, and 0.004 g/L of a fourth growth inhibiting agent. In aspects of this embodiment, a pre-enrichment media comprises 4.3 g/L of a Caseine peptone, 2.4 g/L of Bile Salts, 2.1 g/L of Meat Extract, 2 g/L of a first iodine compound, 2 g/L of a second iodine compound, 0.004 g/L of an aminocoumarin antibiotic, and 0.004 g/L of a triarylmethane dye. In still other aspects of this embodiment, a pre-enrichment media comprises 4.3 g/L of a Caseine peptone, 2.4 g/L of Bile Salts, 2.1 g/L of Meat Extract, 2 g/L of a Iodine, 2 g/L of a Potassium Iodide, 0.004 g/L of Novobiocin, and 0.004 g/L of Brilliant Green.

In another embodiment, a pre-enrichment media further comprises salts. In aspects of this embodiment, a pre-enrichment media further comprises NaCl, CaCO$_3$ and Na$_2$S$_2$O$_3$. In other aspects of this embodiment, a pre-enrichment media further comprises 0.5 g/L to 2.6 g/L NaCl, 18.0 g/L to 20.6 g/L CaCO$_3$ and 13.9 g/L to 16.5 g/L Na$_2$S$_2$O$_3$. In yet other aspects of this embodiment, a pre-enrichment media further comprises 1.0 g/L to 1.6 g/L NaCl, 19.0 g/L to 19.6 g/L CaCO$_3$ and 14.9 g/L to 15.5 g/L Na$_2$S$_2$O$_3$. In still other aspects of this embodiment, a pre-enrichment media further comprises 1.3 g/L NaCl, 19.3 g/L CaCO$_3$ and 15.2 g/L Na$_2$S$_2$O$_3$.

In an embodiment, a pre-enrichment media comprises 2 g/L to 12 g/L of a peptone, 0.05 to 3% (v/v) of a growth inhibiting agent and 0.05 to 5% (v/v) of a surfactant. In aspects of this embodiment, a pre-enrichment media comprises 2 g/L to 12 g/L of a soy peptone, 0.05 to 3% (v/v) of an anti-microbial compound and 0.05 to 5% (v/v) of a surfactant. In other aspects of this embodiment, a pre-enrichment media comprises 2 g/L to 12 g/L of a soy peptone, 0.05 to 3% (v/v) of an anti-microbial compound and 0.05 to 5% (v/v) of a non-ionic surfactant. In yet other aspects of this embodiment, a pre-enrichment media comprises 2 g/L to 12 g/L of a soy peptone, 0.05 to 3% (v/v) of an anti-microbial compound and 0.05 to 5% (v/v) of an ionic surfactant.

In aspects of this embodiment, a pre-enrichment media comprises 2 g/L to 12 g/L of a soy peptone, 0.05 to 3% (v/v) of a triarylmethane dye and 0.05 to 5% (v/v) of a non-ionic surfactant. In other aspects of this embodiment, a pre-enrichment media comprises 2 g/L to 12 g/L of a soy peptone, 0.05 to 3% (v/v) of triarylmethane dye and 0.05 to 5% (v/v) of an ionic surfactant. In yet other aspects of this embodiment, a pre-enrichment media comprises 2 g/L to 12 g/L of a soy peptone, 0.05 to 3% (v/v) of triarylmethane dye and 0.05 to 5% (v/v) of an nonylphenol ethoxylate.

In aspects of this embodiment, a pre-enrichment media comprises 4 g/L to 8 g/L of a soy peptone, 0.05 to 3% (v/v) of a Malachite green dye and 0.05 to 5% (v/v) of an nonylphenol ethoxylate. In other aspects of this embodiment, a pre-enrichment media comprises 4 g/L to 8 g/L of a soy peptone, 0.05 to 3% (v/v) of brilliant green and 0.05 to 5% (v/v) of an nonylphenol ethoxylate. In aspects of this embodiment, a pre-enrichment media comprises 4 g/L to 8 g/L of a soy peptone, 0.05 to 3% (v/v) of a Malachite green dye and 0.05 to 5% (v/v) of an octadecyl sulfate. In other aspects of this embodiment, a pre-enrichment media comprises 4 g/L to 8 g/L of a soy peptone, 0.05 to 3% (v/v) of brilliant green and 0.05 to 5% (v/v) of an octadecyl sulfate.

In aspects of this embodiment, a pre-enrichment media comprises 4 g/L to 8 g/L of a soy peptone, 0.05 to 3% (v/v) of a Malachite green dye and 0.05 to 5% (v/v) of a Nonoxynol-4 (Tergitol-4). In other aspects of this embodiment, a pre-enrichment media comprises 4 g/L to 8 g/L of a soy peptone, 0.05 to 3% (v/v) of Brilliant Green and 0.05 to 5% (v/v) of a Nonoxynol-4 (Tergitol-4). In aspects of this embodiment, a pre-enrichment media comprises 4 g/L to 8 g/L of a soy peptone, 0.05 to 3% (v/v) of a Malachite green dye and 0.05 to 5% (v/v) of a tetradecyl sodium dodecyl sulfate. In other aspects of this embodiment, a pre-enrichment media comprises 4 g/L to 8 g/L of a soy peptone, 0.05 to 3% (v/v) of Brilliant Green and 0.05 to 5% (v/v) of a tetradecyl sodium dodecyl sulfate. In aspects of this embodiment, a pre-enrichment media comprises 4 g/L to 8 g/L of a soy peptone, 0.05 to 3% (v/v) of a Malachite green dye and 0.05 to 5% (v/v) of a 7-ethyl-2-methyl-4-undecyll sodium sulphate. In other aspects of this embodiment, a pre-enrichment media comprises 4 g/L to 8 g/L of a soy peptone, 0.05 to 3% (v/v) of Brilliant Green and 0.05 to 5% (v/v) of a 7-ethyl-2-methyl-4-undecyll sodium sulphate.

In an embodiment, a pre-enrichment media comprises 5 g/L to 15 g/L of a peptone, 2 g/L to 6 g/L Bile Salts, 0.001 g/L to 0.0012 g/L of a growth inhibiting agent and 0.05 mL/L to 6 mL/L of a surfactant. In aspects of this embodiment, a pre-enrichment media comprises 5 g/L to 15 g/L of a Caseine Peptone, 2 g/L to 6 g/L Bile Salts, 0.001 g/L to 0.0012 g/L of an anti-microbial compound and 0.05 mL/L to 6 mL/L of a surfactant. In other aspects of this embodiment, a pre-enrichment media comprises 5 g/L to 15 g/L of a Caseine Peptone, 2 g/L to 6 g/L Bile Salts, 0.001 g/L to 0.0012 g/L of an anti-microbial compound and 0.05 mL/L to 6 mL/L of a non-ionic surfactant. In yet other aspects of this embodiment, a pre-enrichment media comprises 5 g/L to 15 g/L of a Caseine Peptone, 2 g/L to 6 g/L Bile Salts, 0.001 g/L to 0.0012 g/L of an anti-microbial compound and 0.05 mL/L to 6 mL/L of an ionic surfactant.

In aspects of this embodiment, a pre-enrichment media comprises 5 g/L to 15 g/L of a Caseine Peptone, 2 g/L to 6 g/L Bile Salts, 0.001 g/L to 0.0012 g/L of a triarylmethane dye and 0.05 mL/L to 6 mL/L of a surfactant. In other aspects of this embodiment, a pre-enrichment media comprises 5 g/L to 15 g/L of a Caseine Peptone, 2 g/L to 6 g/L Bile Salts, 0.001 g/L to 0.0012 g/L of a triarylmethane dye and 0.05 mL/L to 6 mL/L of a non-ionic surfactant. In yet other aspects of this embodiment, a pre-enrichment media comprises 5 g/L to 15 g/L of a Caseine Peptone, 2 g/L to 6 g/L Bile Salts, 0.001 g/L to 0.0012 g/L of a triarylmethane dye and 0.05 mL/L to 6 mL/L of an ionic surfactant. In aspects of this embodiment, a pre-enrichment media comprises 5 g/L to 15 g/L of a Caseine Peptone, 2 g/L to 6 g/L Bile Salts, 0.001 g/L to 0.0012 g/L of a triarylmethane dye and 0.05 mL/L to 6 mL/L of a nonylphenol ethoxylate.

In aspects of this embodiment, a pre-enrichment media comprises 8 g/L to 12 g/L of a Caseine Peptone, 3 g/L to 5 g/L Bile Salts, 0.004 g/L to 0.0008 g/L of a Malachite green dye and 1.0 mL/L to 3 mL/L of a nonylphenol ethoxylate. In aspects of this embodiment, a pre-enrichment media comprises 8 g/L to 12 g/L of a Caseine Peptone, 3 g/L to 5 g/L Bile Salts, 0.004 g/L to 0.0008 g/L of Brilliant Green and 1.0 mL/L to 3 mL/L of a nonylphenol ethoxylate.

In aspects of this embodiment, a pre-enrichment media comprises 8 g/L to 12 g/L of a Caseine Peptone, 3 g/L to 5 g/L Bile Salts, 0.004 g/L to 0.0008 g/L of a Malachite green dye and 1.0 mL/L to 3 mL/L of Nonoxynol-4 (Tergitol-4). In other aspects of this embodiment, a pre-enrichment media comprises 8 g/L to 12 g/L of a Caseine Peptone, 3 g/L to 5 g/L Bile Salts, 0.004 g/L to 0.0008 g/L of Brilliant Green and 1.0 mL/L to 3 mL/L of Nonoxynol-4 (Tergitol-4).

In another aspect of this embodiment, a pre-enrichment media comprises 10 g/L Caseine Peptone, 4 g/L Bile Salts, 3.5 g/L Disodium Phosphate, 1.5 g/L Potassium Phosphate, 0.006 g/L Brilliant Green, and 2 mL/L Nonoxynol-4 (Tergitol-4). In another aspect of this embodiment, a pre-enrichment media comprises 10 g/L Caseine Peptone, 4 g/L Bile Salts, 3.5 g/L Disodium Phosphate, 1.5 g/L Potassium Phosphate, 0.002 g/L Brilliant Green, and 2 mL/L Nonoxynol-4 (Tergitol-4).

In an embodiment, a pre-enrichment media comprises 5 g/L to 15 g/L of a peptone, 2 g/L to 6 g/L of Bile Salts, 2 g/L to 6 g/L of Meat Extract, 2 g/L to 6 g/L of a first growth inhibiting agent, and 0.001 g/L to 0.0012 g/L of a second growth inhibiting agent. In aspects of this embodiment, a pre-enrichment media comprises 5 g/L to 15 g/L of a Casien peptone, 2 g/L to 6 g/L of Bile Salts, 2 g/L to 6 g/L of Meat Extract, 2 g/L to 6 g/L of an iodine compound, and 0.001 g/L to 0.0012 g/L of an anti-microbial compound. In other aspects of this embodiment, a pre-enrichment media comprises 5 g/L to 15 g/L of a Casien peptone, 2 g/L to 6 g/L of Bile Salts, 2 g/L to 6 g/L of Meat Extract, 2 g/L to 6 g/L of an iodine compound, and 0.001 g/L to 0.0012 g/L of a triarylmethane dye.

In an embodiment, a pre-enrichment media comprises 5 g/L to 15 g/L of a peptone, 2 g/L to 6 g/L of Bile Salts, 2 g/L to 6 g/L of Meat Extract, 2 g/L to 6 g/L of a first growth inhibiting agent, 2 g/L to 6 g/L of a second growth inhibiting agent, and 0.001 g/L to 0.0012 g/L of a third growth inhibiting agent. In aspects of this embodiment, a pre-enrichment media comprises 5 g/L to 15 g/L of a Caseine peptone, 2 g/L to 6 g/L of Bile Salts, 2 g/L to 6 g/L of Meat Extract, 2 g/L to 6 g/L of a first iodine compound, 2 g/L to 6 g/L of a second iodine compound, and 0.001 g/L to 0.0012 g/L of an anti-microbial compound. In other aspects of this embodiment, a pre-enrichment media comprises 5 g/L to 15 g/L of a Caseine peptone, 2 g/L to 6 g/L of Bile Salts, 2 g/L to 6 g/L of Meat Extract, 2 g/L to 6 g/L of a first iodine compound, 2 g/L to 6 g/L of a second iodine compound, and 0.001 g/L to 0.0012 g/L of a triarylmethane dye.

In an embodiment, a pre-enrichment media comprises 5 g/L to 15 g/L of a peptone, 2 g/L to 6 g/L of Bile Salts, 2 g/L to 6 g/L of Meat Extract, 2 g/L to 6 g/L of a first growth inhibiting agent, 2 g/L to 6 g/L of a second growth inhibiting agent, 0.001 g/L to 0.0012 g/L of a third growth inhibiting agent, and 0.001 g/L to 0.0012 g/L of a fourth growth inhibiting agent. In aspects of this embodiment, a pre-enrichment media comprises 5 g/L to 15 g/L of a Caseine peptone, 2 g/L to 6 g/L of Bile Salts, 2 g/L to 6 g/L of Meat Extract, 2 g/L to 6 g/L of a first iodine compound, 2 g/L to 6 g/L of a second iodine compound, 0.001 g/L to 0.0012 g/L of an anti-microbial compound, and 0.001 g/L to 0.0012 g/L of a triarylmethane dye.

In aspects of this embodiment, a pre-enrichment media comprises 7 g/L to 11 g/L of a Caseine peptone, 3.5 g/L to 5.5 g/L Bile Salts, 3 g/L to 5 g/L Meat Extract, 3 g/L to 5 g/L of a first iodine compound, 3 g/L to 5 g/L of a second iodine compound, 0.006 g/L to 0.0010 g/L of an anti-microbial compound, 0.006 g/L to 0.0010 g/L of a triarylmethane dye. In other aspects of this embodiment, a pre-enrichment media comprises 7 g/L to 11 g/L of a Caseine peptone, 3.5 g/L to 5.5 g/L Bile Salts, 3 g/L to 5 g/L Meat Extract, 3 g/L to 5 g/L of Iodine, 3 g/L to 5 g/L of Potassium Iodide, 0.006 g/L to 0.0010 g/L of an aminocoumarin antibiotic, 0.006 g/L to 0.0010 g/L of a Malachite green dye. In yet other aspects of this embodiment, a pre-enrichment media comprises 7 g/L to 11 g/L of a Caseine peptone, 3.5 g/L to 5.5 g/L Bile Salts, 3 g/L to 5 g/L Meat Extract, 3 g/L to 5 g/L of Iodine, 3 g/L to 5 g/L of Potassium Iodide, 0.006 g/L to 0.0010 g/L of Novobiocin, 0.006 g/L to 0.0010 g/L of Brilliant Green.

In another aspect of this embodiment, a pre-enrichment media comprises 4.7 g/L Bile Salts, 4.3 g/L Meat Extract, 8.6 g/L Caseine Peptone, 2.6 g/L NaCl, 38.7 g/L, $CaCO_3$, 30.5 g/L, $Na_2S2O_3$, 4 g/L Iodine, 4 g/L Potassium Iodide, 0.008 g/L Novobiocin, and 0.008 g/L Brilliant Green.

In aspects of this embodiment, a pre-enrichment media comprises 7 g/L to 11 g/L of a Caseine peptone, 3.5 g/L to 5.5 g/L Bile Salts, 3 g/L to 5 g/L Meat Extract, 3 g/L to 5 g/L of a first iodine compound, 3 g/L to 5 g/L of a second iodine compound, 0.002 g/L to 0.006 g/L of an anti-microbial compound, 0.002 g/L to 0.006 g/L of a triarylmethane dye. In other aspects of this embodiment, a pre-enrichment media comprises 7 g/L to 11 g/L of a Caseine peptone, 3.5 g/L to 5.5 g/L Bile Salts, 3 g/L to 5 g/L Meat Extract, 3 g/L to 5 g/L of Iodine, 3 g/L to 5 g/L of Potassium Iodide, 0.002 g/L to 0.006 g/L of an aminocoumarin antibiotic, 0.002 g/L to 0.006 g/L of a Malachite green dye. In yet other aspects of this embodiment, a pre-enrichment media comprises 7 g/L to 11 g/L of a Caseine peptone, 3.5 g/L to 5.5 g/L Bile Salts, 3 g/L to 5 g/L Meat Extract, 3 g/L to 5 g/L of Iodine, 3 g/L to 5 g/L of Potassium Iodide, 0.002 g/L to 0.006 g/L of Novobiocin, 0.002 g/L to 0.006 g/L of Brilliant Green.

In another aspect of this embodiment, a pre-enrichment media comprises 4.7 g/L Bile Salts, 4.3 g/L Meat Extract, 8.6 g/L Caseine Peptone, 2.6 g/L NaCl, 38.7 g/L, $CaCO_3$, 30.5 g/L, $Na_2S2O_3$, 4 g/L Iodine, 4 g/L Potassium Iodide, 0.008 g/L Novobiocin, and 0.008 g/L Brilliant Green. In another aspect of this embodiment, a pre-enrichment media comprises 4.7 g/L Bile Salts, 4.3 g/L Meat Extract, 8.6 g/L Caseine Peptone, 2.6 g/L NaCl, 38.7 g/L, $CaCO_3$, 30.5 g/L, $Na_2S2O_3$, 4 g/L Iodine, 4 g/L Potassium Iodide, 0.004 g/L Novobiocin, and 0.004 g/L Brilliant Green. In another aspect of this embodiment, a pre-enrichment media comprises 2.4 g/L Bile Salts, 2.1 g/L Meat Extract, 4.3 g/L Caseine Peptone, 1.3 g/L NaCl, 19.3 g/L, $CaCO_3$, 15.2 g/L, $Na_2S2O_3$, 2 g/L Iodine, 2 g/L Potassium Iodide, 0.004 g/L Novobiocin, and 0.004 g/L Brilliant Green. In another aspect of this embodiment, a pre-enrichment media comprises 2.4 g/L Bile Salts, 4.3 g/L Soy Peptone, 1.3 g/L NaCl, 19.3 g/L, $CaCO_3$, 15.2 g/L, $Na_2S2O_3$, 2 g/L Iodine, 2 g/L Potassium Iodide, 0.004 g/L Novobiocin, and 0.004 g/L Brilliant Green.

In an embodiment, a pre-enrichment media comprises 5 g/L to 15 g/L of a peptone, 2 g/L to 6 g/L of Bile Salts, 2 g/L to 6 g/L of a first growth inhibiting agent, 2 g/L to 6 g/L of a second growth inhibiting agent, and 0.001 g/L to 0.0012 g/L of a third growth inhibiting agent. In aspects of this embodiment, a pre-enrichment media comprises 5 g/L to 15 g/L of a Caseine peptone, 2 g/L to 6 g/L of Bile Salts, 2 g/L to 6 g/L of a first iodine compound, 2 g/L to 6 g/L of a second iodine compound, and 0.001 g/L to 0.0012 g/L of an anti-microbial compound. In other aspects of this embodiment, a pre-enrichment media comprises 5 g/L to 15 g/L of a Caseine peptone, 2 g/L to 6 g/L of Bile Salts, 2 g/L to 6 g/L of a first iodine compound, 2 g/L to 6 g/L of a second iodine compound, and 0.001 g/L to 0.0012 g/L of a triarylmethane dye.

In aspects of this embodiment, a pre-enrichment media comprises 8 g/L to 12 g/L of a Caseine peptone, 3 g/L to 5 g/L Bile Salts, 3 g/L to 5 g/L of a first iodine compound, 3 g/L to 5 g/L of a second iodine compound, and 0.002 g/L to 0.006 g/L of an anti-microbial compound. In other aspects of this embodiment, a pre-enrichment media comprises 8 g/L to 12 of a Caseine peptone, 3 g/L to 5 g/L Bile Salts, 3 g/L to 5 g/L of Iodine, 3 g/L to 5 g/L of Potassium Iodide, and 0.002 g/L to 0.006 g/L of an aminocoumarin antibiotic. In yet other aspects of this embodiment, a pre-enrichment media comprises 8 g/L to 12 of a Caseine peptone, 3 g/L to 5 g/L Bile Salts, 3 g/L to 5 g/L of Iodine, 3 g/L to 5 g/L of Potassium Iodide, and 0.002 g/L to 0.006 g/L of Novobiocin.

In another aspect of this embodiment, a pre-enrichment media comprises 10 g/L Caseine Peptone, 4 g/L Bile Salts, 3.5 g/L Disodium Phosphate, 1.5 g/L Potassium Phosphate, 7.6 g/L NaCl, 30.5 g/L, $Na_2S2O_3$, 4 g/L Iodide, 4 g/L Potassium Iodide, and 0.004 g/L Novobiocin. In another aspect of this embodiment, a pre-enrichment media comprises 10 g/L Caseine Peptone, 2.4 g/L Bile Salts, 3.5 g/L Disodium Phosphate, 1.5 g/L Potassium Phosphate, 6.3 g/L NaCl, 15.2 g/L, $Na_2S2O_3$, 4 g/L Iodide, 4 g/L Potassium Iodide, 0.004 g/L Novobiocin, In another aspect of this embodiment, a pre-enrichment media comprises 10 g/L Caseine Peptone, 2.4 g/L Bile Salts, 3.5 g/L Disodium Phosphate, 1.5 g/L Potassium Phosphate, 6.3 g/L NaCl, 19.3 g/L, CaCO$_3$, 15.2 g/L, Na$_2$S$_2$O$_3$, 4 g/L Iodide, 4 g/L Potassium Iodide, and 0.004 g/L Novobiocin.

In an embodiment, a pre-enrichment media comprises 3 g/L to 7 g/L of a Tryptone and 0.5 g/L to 3 g/L of a growth inhibiting agent. In aspects of this embodiment, a pre-enrichment media comprises 3 g/L to 7 g/L of a Tryptone and 0.5 g/L to 3 g/L of an anti-microbial compound. In other aspects of this embodiment, a pre-enrichment media comprises 3 g/L to 7 g/L of a Tryptone and 0.5 g/L to 3 g/L of a selenium compound. In yet other aspects of this embodiment, a pre-enrichment media comprises 3 g/L to 7 g/L of a Tryptone and 0.5 g/L to 3 g/L of Sodium Hydrogen Selenite. In still other aspects of this embodiment, a pre-enrichment media comprises 4 g/L to 6 g/L of a Tryptone and 1 g/L to 2 g/L of Sodium Hydrogen Selenite. In another aspect of this embodiment, a pre-enrichment media comprises 5 g/L Tryptone, 4 g/L Lactose, 10 g/L Disodium Phosphate, 0.01 g/L L-Cystine, and 1.51 g/L Sodium Hydrogen Selenite.

In an embodiment, a pre-enrichment media comprises 3 g/L to 7 g/L of a Tryptone, 1 g/L to 3 g/L of Bile Salts, 2 g/L to 6 g/L of a first growth inhibiting agent, 2 g/L to 6 g/L of a second growth inhibiting agent, and 0.001 g/L to 0.0012 g/L of a third growth inhibiting agent. In aspects of this embodiment, a pre-enrichment media comprises 3 g/L to 7 g/L of a Tryptone, 1 g/L to 3 g/L of Bile Salts, 2 g/L to 6 g/L of a first iodine compound, 2 g/L to 6 g/L of a second iodine compound, and 0.001 g/L to 0.0012 g/L of an anti-microbial compound. In other aspects of this embodiment, a pre-enrichment media comprises 3 g/L to 7 g/L of a Tryptone, 1 g/L to 3 g/L of Bile Salts, 2 g/L to 6 g/L of a first iodine compound, 2 g/L to 6 g/L of a second iodine compound, and 0.001 g/L to 0.0012 g/L of a triarylmethane dye.

In aspects of this embodiment, a pre-enrichment media comprises 4 g/L to 6 g/L of a Tryptone, 1.5 g/L to 3.5 g/L Bile Salts, 3 g/L to 5 g/L of a first iodine compound, 3 g/L to 5 g/L of a second iodine compound, and 0.002 g/L to 0.006 g/L of an anti-microbial compound. In other aspects of this embodiment, a pre-enrichment media comprises 4 g/L to 6 g/L of a Tryptone, 1.5 g/L to 3.5 g/L Bile Salts, 3 g/L to 5 g/L of Iodine, 3 g/L to 5 g/L of Potassium Iodide, and 0.002 g/L to 0.006 g/L of an aminocoumarin antibiotic. In yet other aspects of this embodiment, a pre-enrichment media comprises 4 g/L to 6 g/L of a Tryptone, 1.5 g/L to 3.5 g/L Bile Salts, 3 g/L to 5 g/L of Iodine, 3 g/L to 5 g/L of Potassium Iodide, and 0.002 g/L to 0.006 g/L of Novobiocin.

In another aspect of this embodiment, a pre-enrichment media comprises 5 g/L Tryptone, 4 g/L Lactose, 2.4 g/L Bile Salts, 10 g/L Disodium Phosphate, 0.01 g/L L-Cystine, 19.3 g/L, CaCO$_3$, 30.5 g/L, Na$_2$S$_2$O$_3$, 4 g/L Iodide, 4 g/L Potassium Iodide, and 0.004 g/L Novobiocin. In another aspect of this embodiment, a pre-enrichment media comprises 5 g/L Tryptone, 4 g/L Lactose, 2.4 g/L Bile Salts, 10 g/L Disodium Phosphate, 0.01 g/L L-Cystine, 30.5 g/L, Na$_2$S$_2$O$_3$, 4 g/L Iodide, 4 g/L Potassium Iodide, and 0.004 g/L Novobiocin.

Aspect of the present specification disclose, in part, incubation of a sample in a pre-enrichment media. Incubation of a sample is performed under temperature and time parameters that facilitate the growth of the pathogen in the sample, retard the growth of an unwanted organism in the sample, and/or establish conditions that otherwise increase the population of the pathogen in the sample and/or retard the growth of an unwanted organism in the sample. Incubation of pre-enrichment media may be performed under constant rotation, reversal or agitation.

Any temperature may be used during incubation of a sample in a pre-enrichment media, with the proviso that the temperature is useful to practice the methods disclosed herein. In aspects of this embodiment, a temperature used to incubate of a sample in a pre-enrichment media may be, e.g., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., or about 42° C. In other aspects of this embodiment, a temperature used to incubate of a sample in a pre-enrichment media may be, e.g., at least 25° C., at least 26° C., at least 27° C., at least 28° C., at least 29° C., at least 30° C., at least 31° C., at least 32° C., at least 33° C., at least 34° C., at least 35° C., at least 36° C., at least 37° C., at least 38° C., at least 39° C., at least 40° C., at least 41° C., or at least 42° C. In yet other aspects of this embodiment, a temperature used to incubate of a sample in a pre-enrichment media may be, e.g., at most 25° C., at most 26° C., at most 27° C., at most 28° C., at most 29° C., at most 30° C., at most 31° C., at most 32° C., at most 33° C., at most 34° C., at most 35° C., at most 36° C., at most 37° C., at most 38° C., at most 39° C., at most 40° C., at most 41° C., or at most 42° C. In still other aspects of this embodiment, a temperature used to incubate of a sample in a pre-enrichment media may be, e.g., about 25° C. to about 29° C., about 26° C. to about 30° C., about 27° C. to about 31° C., about 28° C. to about 32° C., about 29° C. to about 33° C., about 30° C. to about 34° C., about 31° C. to about 35° C., about 32° C. to about 36° C., about 33° C. to about 37° C., about 34° C. to about 38° C., about 35° C. to about 39° C., about 36° C. to about 40° C., about 37° C. to about 41° C., about 38° C. to about 42° C., about 39° C. to about 43° C., or about 40° C. to about 44° C. In still other aspects of this embodiment, a temperature used to incubate of a sample in a pre-enrichment media may be, e.g., about 34° C. to about 39° C., about 34° C. to about 40° C., about 35° C. to about 45° C., about 36° C. to about 44° C., about 36° C. to about 43° C., about 37° C. to about 42° C., about 34° C. to about 45° C. or about 39° C. to about 45° C.

Any time may be used during incubation of a sample in a pre-enrichment media, with the proviso that the time is useful to practice the methods disclosed herein. In aspects of this embodiment, a time used to incubate of a sample in a pre-enrichment media may be, e.g., about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In other aspects of this embodiment, a time used to incubate of a sample in a pre-enrichment media may be, e.g., at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, or at least 24 hours. In yet other aspects of this embodiment, a time used to incubate of a sample in a pre-enrichment media may be, e.g., at most 4 hours, at most 5 hours, at most 6 hours, at most 7 hours, at most 8 hours, at most 9 hours, at most 10 hours, at most 11 hours, at most 12 hours, at most 13 hours, at most 14 hours, at most 15 hours, at most 16 hours, at most 17 hours, at most 18 hours, at most 19 hours, at most 20 hours, at most 21 hours, at most 22 hours, at most 23 hours, or at most 24 hours. In yet other aspects of this embodiment, a time used to incubate of a sample in a pre-enrichment media may be, e.g., about 4 hours to about 6 hours, about 5 hours to about 7 hours, about 6 hours to about 8 hours, about 7 hours to about 9 hours, about 8 hours to about 10 hours, about 9 hours to about 11 hours, about 10 hours to about 12 hours, about 11 hours to about 13 hours, about 12 hours to about 14 hours, about 13 hours to about 15 hours, about 14 hours to about 16 hours, about 15 hours to about 17 hours, about 16 hours to about 18 hours, about 17 hours to about 19 hours, about 18 hours to about 20 hours, about 19 hours to about 21 hours, about 20 hours to about 22 hours, about 21 hours to about 23 hours, about 22 hours to about 24 hours, about 23 hours to about 25 hours, or about 24 hours to about 26 hours. In other aspects of this embodiment, a time used to incubate of a sample in a pre-enrichment media may be, e.g., about 1 hour to about 2 hours, about 1 hour to about 3 hours, about 1 hour to about 4 hours, about 1 hour to about 5 hours, about 1 hour to about 6 hours, about 4 hours to about 11 hours, about 5 hours to about 10 hours, about 6 hours to about 9 hours, about 7 hours to about 8 hours, about 5 hours to about 10 hours, about 6 hours to about 9 hours, about 5 hours to about 11 hours, about 6 hours to about 10 hours, about 7 hours to about 9 hours, about 4 hours to about 10 hours, about 5 hours to about 9 hours or about 6 hours to about 8 hours.

In aspects of this embodiment, a sample in a pre-enrichment media may be incubated at a temperature of, e.g., about 34° C. to about 39° C., about 34° C. to about 40° C., about 35° C. to about 45° C., about 36° C. to about 44° C., about 36° C. to about 43° C., about 37° C. to about 42° C., about 35° C. to about 39° C., about 34° C. to about 45° C. or about 39° C. to about 45° C. for a time of, e.g., about 1 hour to about 2 hours, about 1 hour to about 3 hours, about 1 hour to about 4 hours, about 1 hour to about 5 hours, about 1 hour to about 6 hours. Incubation of pre-enrichment media may be performed under constant rotation, reversal or agitation.

In aspects of this embodiment, a sample in a pre-enrichment media may be incubated at a temperature of, e.g., about 34° C. to about 39° C., about 34° C. to about 40° C., about 35° C. to about 45° C., about 36° C. to about 44° C., about 36° C. to about 43° C., about 37° C. to about 42° C., about 35° C. to about 39° C., about 34° C. to about 45° C. or about 39° C. to about 45° C. for a time of, e.g., about 4 hours to about 11 hours, about 5 hours to about 10 hours, about 6 hours to about 9 hours, about 7 hours to about 8 hours, about 5 hours to about 10 hours, about 6 hours to about 9 hours, about 5 hours to about 11 hours, about 6 hours to about 10 hours, about 7 hours to about 9 hours, about 4 hours to about 10 hours, about 5 hours to about 9 hours or about 6 hours to about 8 hours. Incubation of pre-enrichment media may be performed under constant rotation, reversal or agitation.

In aspects of this embodiment, a sample in a pre-enrichment media may be incubated at a temperature of, e.g., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., or about 42° C. for a time of, e.g., about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. Incubation of pre-enrichment media may be performed under constant rotation, reversal or agitation.

In other aspects of this embodiment, a sample in a pre-enrichment media may be incubated at a temperature of, e.g., at least 25° C., at least 26° C., at least 27° C., at least 28° C., at least 29° C., at least 30° C., at least 31° C., at least 32° C., at least 33° C., at least 34° C., at least 35° C., at least 36° C., at least 37° C., at least 38° C., at least 39° C., at least 40° C., at least 41° C., or at least 42° C. for a time of, e.g., at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, or at least 24 hours. Incubation of pre-enrichment media may be performed under constant rotation, reversal or agitation.

In yet other aspects of this embodiment, a sample in a pre-enrichment media may be incubated at a temperature of, e.g., at most 25° C., at most 26° C., at most 27° C., at most 28° C., at most 29° C., at most 30° C., at most 31° C., at most 32° C., at most 33° C., at most 34° C., at most 35° C., at most 36° C., at most 37° C., at most 38° C., at most 39° C., at most 40° C., at most 41° C., or at most 42° C. for a time of, e.g., at most 4 hours, at most 5 hours, at most 6 hours, at most 7 hours, at most 8 hours, at most 9 hours, at most 10 hours, at most 11 hours, at most 12 hours, at most 13 hours, at most 14 hours, at most 15 hours, at most 16 hours, at most 17 hours, at most 18 hours, at most 19 hours, at most 20 hours, at most 21 hours, at most 22 hours, at most 23 hours, or at most 24 hours. Incubation of pre-enrichment media may be performed under constant rotation, reversal or agitation.

In still other aspects of this embodiment, a sample in a pre-enrichment media may be incubated at a temperature of, e.g., about 25° C. to about 29° C., about 26° C. to about 30° C., about 27° C. to about 31° C., about 28° C. to about 32° C., about 29° C. to about 33° C., about 30° C. to about 34° C., about 31° C. to about 35° C., about 32° C. to about 36° C., about 33° C. to about 37° C., about 34° C. to about 38° C., about 35° C. to about 39° C., about 36° C. to about 40° C., about 37° C. to about 41° C., about 38° C. to about 42° C., about 39° C. to about 43° C., or about 40° C. to about 44° C. for a time of, e.g., about 4 hours to about 6 hours, about 5 hours to about 7 hours, about 6 hours to about 8 hours, about 7 hours to about 9 hours, about 8 hours to about 10 hours, about 9 hours to about 11 hours, about 10 hours to about 12 hours, about 11 hours to about 13 hours, about 12 hours to about 14 hours, about 13 hours to about 15 hours, about 14 hours to about 16 hours, about 15 hours to about 17 hours, about 16 hours to about 18 hours, about 17 hours to about 19 hours, about 18 hours to about 20 hours, about 19 hours to about 21 hours, about 20 hours to about 22 hours, about 21 hours to about 23 hours, about 22 hours to about 24 hours, about 23 hours to about 25 hours, or about 24 hours to about 26 hours. Incubation of pre-enrichment media may be performed under constant rotation, reversal or agitation.

A method for the detection of a pathogen in a sample comprises the step of incubation of the sample in an enrichment media. After a pre-enrichment media step disclosed herein is completed, an aliquot of the pre-enrichment media is transferred to an enrichment media for subsequent growth of the pathogen. An enrichment step comprises incubating an aliquot of the pre-enrichment media in an enrichment media for a defined time and at a defined temperature.

Any volume of an aliquoit of pre-enrichment media may be used during incubation of a pre-enrichment media in a enrichment media, with the proviso that the volume is useful to practice the methods disclosed herein. In aspects of this embodiment, an aliquot volume of pre-enrichment media transferred to an enrichment media may be, e.g., about 1/50, about 1/75, about 1/100, about 1/125, about 1/150, about 1/175, about 1/200, about 1/225, about 1/250, about 1/275, about 1/300, about 1/325, about 1/350, about 1/375, about 1/400, about 1/425, about 1/450, about 1/475, about 1/500, about 1/525, about 1/550, about 1/575, about 1/600, about 1/625, about 1/650, about 1/675, about 1/700, about 1/725, about 1/750, about 1/775, about 1/800, about 1/825, about 1/850, about 1/875, about 1/900, about 1/925, about 1/950, about 1/975, or about 1/1,000 the volume of an enrichment media used in an enrichment step. In other aspects of this embodiment, an aliquot volume of pre-enrichment media transferred to an enrichment media may be, e.g., at least 1/50, at least 1/75, at least 1/100, at least 1/125, at least 1/150, at least 1/175, at least 1/200, at least 1/225, at least 1/250, at least 1/275, at least 1/300, at least 1/325, at least 1/350, at least 1/375, at least 1/400, at least 1/425, at least 1/450, at least 1/475, at least 1/500, at least 1/525, at least 1/550, at least 1/575, at least 1/600, at least 1/625, at least 1/650, at least 1/675, at least 1/700, at least 1/725, at least 1/750, at least 1/775, at least 1/800, at least 1/825, at least 1/850, at least 1/875, at least 1/900, at least 1/925, at least 1/950, at least 1/975, or at least 1/1,000 the volume of an enrichment media used in an enrichment step. In yet other aspects of this embodiment, an aliquot volume of pre-enrichment media transferred to an enrichment media may be, e.g., at most 1/50, at most 1/75, at most 1/100, at most 1/125, at most 1/150, at most 1/175, at most 1/200, at most 1/225, at most 1/250, at most 1/275, at most 1/300, at most 1/325, at most 1/350, at most 1/375, at most 1/400, at most 1/425, at most 1/450, at most 1/475, at most 1/500, at most 1/525, at most 1/550, at most 1/575, at most 1/600, at most 1/625, at most 1/650, at most 1/675, at most 1/700, at most 1/725, at most 1/750, at most 1/775, at most 1/800, at most 1/825, at most 1/850, at most 1/875, at most 1/900, at most 1/925, at most 1/950, at most 1/975, or at most 1/1,000 the volume of an enrichment media used in an enrichment step.

In yet other aspects of this embodiment, an aliquot volume of pre-enrichment media transferred to an enrichment media may be, e.g., about 1/5 to about 1/100, about 1/5 to about 1/150, about 1/5 to about 1/200, about 1/5 to about 1/250, about 1/5 to about 1/300, about 1/5 to about 1/350, about 1/5 to about 1/400, about 1/5 to about 1/450, about 1/5 to about 1/500, about 1/5 to about 1/550, about 1/5 to about 1/600, about 1/5 to about 1/650, about 1/5 to about 1/700, about 1/5 to about 1/750, about 1/5 to about 1/800, about 1/5 to about 1/850, about 1/5 to about 1/900, about 1/5 to about 1/950, about 1/5 to about 1/1,000, about 1/10 to about 1/100, about 1/10 to about 1/150, about 1/10 to about 1/200, about 1/10 to about 1/250, about 1/10 to about 1/300, about 1/10 to about 1/350, about 1/10 to about 1/400, about 1/10 to about 1/450, about 1/10 to about 1/500, about 1/10 to about 1/550, about 1/10 to about 1/600, about 1/10 to about 1/650, about 1/10 to about 1/700, about 1/10 to about 1/750, about 1/10 to about 1/800, about 1/10 to about 1/850, about 1/10 to about 1/900, about 1/10 to about 1/950, about 1/10 to about 1/1,000, about 1/50 to about 1/100, about 1/50 to about 1/150, about 1/50 to about 1/200, about 1/50 to about 1/250, about 1/50 to about 1/300, about 1/50 to about 1/350, about 1/50 to about 1/400, about 1/50 to about 1/450, about 1/50 to about 1/500, about 1/50 to about 1/550, about 1/50 to about 1/600, about 1/50 to about 1/650, about 1/50 to about 1/700, about 1/50 to about 1/750, about 1/50 to about 1/800, about 1/50 to about 1/850, about 1/50 to about 1/900, about 1/50 to about 1/950, about 1/50 to about 1/1,000, about 1/100 to about 1/150, about 1/100 to about 1/200, about 1/100 to about 1/250, about 1/100 to about 1/300, about 1/100 to about 1/350, about 1/100 to about 1/400, about 1/100 to about 1/450, about 1/100 to about 1/500, about 1/100 to about 1/550, about 1/100 to about 1/600, about 1/100 to about 1/650, about 1/100 to about 1/700, about 1/100 to about 1/750, about 1/100 to about 1/800, about 1/100 to about 1/850, about 1/100 to about 1/900, about 1/100 to about 1/950, about 1/100 to about 1/1,000, about 1/200 to about 1/300, about 1/200 to about 1/350, about 1/200 to about 1/400, about 1/200 to about 1/450, about 1/200 to about 1/500, about 1/200 to about 1/550, about 1/200 to about 1/600, about 1/200 to about 1/650, about 1/200 to about 1/700, about 1/200 to about 1/750, about 1/200 to about 1/800, about 1/200 to about 1/850, about 1/200 to about 1/900, about 1/200 to about 1/950, about 1/200 to about 1/1,000, about 1/300 to about 1/350, about 1/300 to about 1/400, about 1/300 to about 1/450, about 1/300 to about 1/500, about 1/300 to about 1/550, about 1/300 to about 1/600, about 1/300 to about 1/650, about 1/300 to about 1/700, about 1/300 to about 1/750, about 1/300 to about 1/800, about 1/300 to about 1/850, about 1/300 to about 1/900, about 1/300 to about 1/950, about 1/300 to about 1/1,000, about 1/400 to about 1/450, about 1/400 to about 1/500, about 1/400 to about 1/550, about 1/400 to about 1/600, about 1/400 to about 1/650, about 1/400 to about 1/700, about 1/400 to about 1/750, about 1/400 to about 1/800, about 1/400 to about 1/850, about 1/400 to about 1/900, about 1/400 to about 1/950, about 1/400 to about 1/1,000, about 1/500 to about 1/550, about 1/500 to about 1/600, about 1/500 to about 1/650, about 1/500 to about 1/700, about 1/500 to about 1/750, about 1/500 to about 1/800, about 1/500 to about 1/850, about 1/500 to about 1/900, about 1/500 to about 1/950, or about 1/500 to about 1/1,000.

In aspects of this embodiment, a ratio of pre-enrichment media to enrichment media may used in an enrichment step may be, e.g., about 1:5, about 1:10, about 1:25, about 1:50, about 1:75, about 1:100, about 1:125, about 1:150, about 1:175, about 1:200, about 1:225, about 1:250, about 1:275, about 1:300, about 1:325, about 1:350, about 1:375, about 1:400, about 1:425, about 1:450, about 1:475, about 1:500, about 1:525, about 1:550, about 1:575, about 1:600, about 1:625, about 1:650, about 1:675, about 1:700, about 1:725, about 1:750, about 1:775, about 1:800, about 1:825, about 1:850, about 1:875, about 1:900, about 1:925, about 1:950, about 1:975, or about 1:1,000. In other aspects of this embodiment, a ratio of pre-enrichment media to enrichment media may used in an enrichment step may be, e.g., at least 1:5, at least 1:10, at least 1:25, at least 1:50, at least 1:75, at least 1:100, at least 1:125, at least 1:150, at least 1:175, at least 1:200, at least 1:225, at least 1:250, at least 1:275, at least 1:300, at least 1:325, at least 1:350, at least 1:375, at least 1:400, at least 1:425, at least 1:450, at least 1:475, at least 1:500, at least 1:525, at least 1:550, at least 1:575, at least 1:600, at least 1:625, at least 1:650, at least 1:675, at least 1:700, at least 1:725, at least 1:750, at least 1:775, at least 1:800, at least 1:825, at least 1:850, at least 1:875, at least 1:900, at least 1:925, at least 1:950, at least 1:975, or at least 1:1,000. In yet other aspects of this embodiment, a ratio of pre-enrichment media to enrichment media may used in an enrichment step may be, e.g., at most 1:5, at most 1:10, at most 1:25, at most 1:50, at most 1:75, at most 1:100, at most 1:125, at most 1:150, at most 1:175, at most 1:200, at most 1:225, at most 1:250, at most 1:275, at most 1:300, at most 1:325, at most 1:350, at most 1:375, at most 1:400, at most 1:425, at most 1:450, at most 1:475, at most 1:500, at most 1:525, at most 1:550, at most 1:575, at most 1:600, at most 1:625, at most 1:650, at most 1:675, at most 1:700, at most 1:725, at most 1:750, at most 1:775, at most 1:800, at most 1:825, at most 1:850, at most 1:875, at most 1:900, at most 1:925, at most 1:950, at most 1:975, or at most 1:1,000.

In still other aspects of this embodiment, a ratio of pre-enrichment media to enrichment media may used in an enrichment step may be, e.g., about 1:5 to about 1:100, about 1:5 to about 1:150, about 1:5 to about 1:200, about 1:5 to about 1:250, about 1:5 to about 1:300, about 1:5 to about 1:350, about 1:5 to about 1:400, about 1:5 to about 1:450, about 1:5 to about 1:500, about 1:5 to about 1:550, about 1:5 to about 1:600, about 1:5 to about 1:650, about 1:5 to about 1:700, about 1:5 to about 1:750, about 1:5 to about 1:800, about 1:5 to about 1:850, about 1:5 to about 1:900, about 1:5 to about 1:950, about 1:5 to about 1:1,000, about 1:10 to about 1:100, about 1:10 to about 1:150, about 1:10 to about 1:200, about 1:10 to about 1:250, about 1:10 to about 1:300, about 1:10 to about 1:350, about 1:10 to about 1:400, about 1:10 to about 1:450, about 1:10 to about 1:500, about 1:10 to about 1:550, about 1:10 to about 1:600, about 1:10 to about 1:650, about 1:10 to about 1:700, about 1:10 to about 1:750, about 1:10 to about 1:800, about 1:10 to about 1:850, about 1:10 to about 1:900, about 1:10 to about 1:950, about 1:10 to about 1:1,000, about 1:50 to about 1:100, about 1:50 to about 1:150, about 1:50 to about 1:200, about 1:50 to about 1:250, about 1:50 to about 1:300, about 1:50 to about 1:350, about 1:50 to about 1:400, about 1:50 to about 1:450, about 1:50 to about 1:500, about 1:50 to about 1:550, about 1:50 to about 1:600, about 1:50 to about 1:650, about 1:50 to about 1:700, about 1:50 to about 1:750, about 1:50 to about 1:800, about 1:50 to about 1:850, about 1:50 to about 1:900, about 1:50 to about 1:950, about 1:50 to about 1:1,000, about 1:100 to about 1:200, about 1:100 to about 1:250, about 1:100 to about 1:300, about 1:100 to about 1:350, about 1:100 to about 1:400, about 1:100 to about 1:450, about 1:100 to about 1:500, about 1:100 to about 1:550, about 1:100 to about 1:600, about 1:100 to about 1:650, about 1:100 to about 1:700, about 1:100 to about 1:750, about 1:100 to about 1:800, about 1:100 to about 1:850, about 1:100 to about 1:900, about 1:100 to about 1:950, about 1:100 to about 1:1,000, about 1:200 to about 1:250, about 1:200 to about 1:300, about 1:200 to about 1:350, about 1:200 to about 1:400, about 1:200 to about 1:450, about 1:200 to about 1:500, about 1:200 to about 1:550, about 1:200 to about 1:600, about 1:200 to about 1:650, about 1:200 to about 1:700, about 1:200 to about 1:750, about 1:200 to about 1:800, about 1:200 to about 1:850, about 1:200 to about 1:900, about 1:200 to about 1:950, about 1:200 to about 1:1,000, about 1:300 to about 1:350, about 1:300 to about 1:400, about 1:300 to about 1:450, about 1:300 to about 1:500, about 1:300 to about 1:550, about 1:300 to about 1:600, about 1:300 to about 1:650, about 1:300 to about 1:700, about 1:300 to about 1:750, about 1:300 to about 1:800, about 1:300 to about 1:850, about 1:300 to about 1:900, about 1:300 to about 1:950, about 1:300 to about 1:1,000, about 1:400 to about 1:450, about 1:400 to about 1:500, about 1:400 to about 1:550, about 1:400 to about 1:600, about 1:400 to about 1:650, about 1:400 to about 1:700, about 1:400 to about 1:750, about 1:400 to about 1:800, about 1:400 to about 1:850, about 1:400 to about 1:900, about 1:400 to about 1:950, about 1:400 to about 1:1,000, about 1:500 to about 1:550, about 1:500 to about 1:600, about 1:500 to about 1:650, about 1:500 to about 1:700, about 1:500 to about 1:750, about 1:500 to about 1:800, about 1:500 to about 1:850, about 1:500 to about 1:900, about 1:500 to about 1:950, about 1:500 to about 1:1,000, about 1:600 to about 1:650, about 1:600 to about 1:700, about 1:600 to about 1:750, about 1:600 to about 1:800, about 1:600 to about 1:850, about 1:600 to about 1:900, about 1:600 to about 1:950, about 1:600 to about 1:1,000, about 1:700 to about 1:750, about 1:700 to about 1:800, about 1:700 to about 1:850, about 1:700 to about 1:900, about 1:700 to about 1:950, about 1:700 to about 1:1,000, about 1:800 to about 1:850, about 1:800 to about 1:900, about 1:800 to about 1:950, about 1:800 to about 1:1,000, about 1:900 to about 1:950, about 1:900 to about 1:1,000, or about 1:950 to about 1:1,000.

Aspect of the present specification disclose, in part, an enrichment media. An enrichment media, also referred to as an enrichment culture media is a buffered culture media that provides the nutrients necessary to sustain high-growth of the pathogen. This is typically done by tailoring the media particularly conducive to the growth of the pathogen such as, e.g., considering survivable osmotic pressure ranges, survivable pH ranges, resistance to selective compounds, minimal nutritional requirements. Non-limiting examples of an enrichment media include a Rappaport Vassiliadis Soya Medium (RVS), a McConkey Broth, a Fraser Broth, a Soy-Triptone Broth (TSB), a Reinforce *Clostridium* Broth, a *Campylobacter* Thioglycolate Medium, a Nitrate Broth, a Triple Sugar Iron Broth (TSI), a Sodium Hippurate Broth, a Selenite Cystine Broth, a GN Broth, a Todd Hewitt Broth, a Malt Extract Broth, an Azide Dextrose Broth, and a Hektoen Broth.

In an aspect of this embodiment, when the pathogen is a *Salmonella* sp., the enrichment media may be a Rappaport Vassiliadis Soya Medium, a Selenite Cystine Broth, or a GN Broth. In another aspect of this embodiment, when the pathogen is an *Escherichia coli*, the enrichment media may be a McConkey Broth. In yet another aspect of this embodiment, when the pathogen is a *Listeria monocytogenes*, the enrichment media may be a Fraser Broth. In still another aspect of this embodiment, when the pathogen is a *Staphylococcus aureus*, the enrichment media may be a Soy-Triptone Broth (TSB). In another aspect of this embodiment, when the pathogen is a *Clostridium* sp., the enrichment media may be a Reinforce *Clostridium* Broth. In yet another aspect of this embodiment, when the pathogen is a *Campylobacter* sp., the enrichment media may be a *Campylobacter* Thioglycolate Medium.

In another aspect of this embodiment, when the pathogen is a *Pseudomonas* sp., the enrichment media may be a Nitrate Broth or a Triple Sugar Iron Broth (TSI). In yet another aspect of this embodiment, when the pathogen is an *Acinetobacter* sp., the enrichment media may be a Nitrate Broth or a Triple Sugar Iron Broth (TSI). In still another aspect of this embodiment, when the pathogen is a *Legionella* sp., the enrichment media may be a Sodium Hippurate Broth. In another aspect of this embodiment, when the pathogen is a *Shigella* sp., the enrichment media may be a Selenite Cystine Broth or a GN Broth. In yet another aspect of this embodiment, when the pathogen is a *Streptococcus* sp., the enrichment media may be a Todd Hewitt Broth. In another aspect of this embodiment, when the pathogen is an *Enterococcus* sp., the enrichment media may be an Azide Dextrose Broth.

In another aspect of this embodiment, when the pathogen is a fungus, the enrichment media may be a Malt Extract Broth. In yet another aspect of this embodiment, when the pathogen is a yeast, the enrichment media may be a Malt Extract Broth. In still another aspect of this embodiment, when the pathogen is a mold, the enrichment media may be a Malt Extract Broth. In another aspect of this embodiment, when the pathogen is a *Proteus*, the enrichment media may be a Hektoen Broth.

An enrichment media typically comprises a high growth nutrient component used as a source of proteins, amino acids and nitrogen. Either a single high growth nutrient component may comprise an enrichment media disclosed herein, or a plurality of high growth nutrient components may comprise an enrichment media disclosed herein. A non-limiting example of a high growth nutrient component is a peptone as disclosed herein.

Any concentration of high growth nutrient component may be used, with the proviso that the concentration is useful to practice the methods disclosed herein. In aspects of this embodiment, a high growth nutrient component may be used at a concentration of, e.g., about 1 g/L, about 2 g/L, about 3 g/L, about 4 g/L, about 5 g/L, about 6 g/L, about 7 g/L, about 8 g/L, about 9 g/L, about 10 g/L, about 11 g/L, about 12 g/L, about 13 g/L, about 14 g/L, or about 15 g/L. In other aspects of this embodiment, a high growth nutrient component may be used at a concentration of, e.g., at least 1 g/L, at least 2 g/L, at least 3 g/L, at least 4 g/L, at least 5 g/L, at least 6 g/L, at least 7 g/L, at least 8 g/L, at least 9 g/L, at least 10 g/L, at least 11 g/L, at least 12 g/L, at least 13 g/L, at least 14 g/L, or at least 15 g/L. In yet other aspects of this embodiment, a high growth nutrient component may be used at a concentration of, e.g., at most 1 g/L, at most 2 g/L, at most 3 g/L, at most 4 g/L, at most 5 g/L, at most 6 g/L, at most 7 g/L, at most 8 g/L, at most 9 g/L, at most 10 g/L, at most 11 g/L, at most 12 g/L, at most 13 g/L, at most 14 g/L, or at most 15 g/L.

In yet other aspects of this embodiment, a high growth nutrient component may be used at a concentration of between, e.g., about 1 g/L to 2 g/L, about 1 g/L to 3 g/L, about 1 g/L to 4 g/L, about 1 g/L to 5 g/L, about 1 g/L to 6 g/L, about 1 g/L to 7 g/L, about 1 g/L to 8 g/L, about 1 g/L to 9 g/L, about 1 g/L to 10 g/L, about 1 g/L to 11 g/L, about 1 g/L to 12 g/L, about 1 g/L to 13 g/L, about 1 g/L to 14 g/L, about 1 g/L to 15 g/L, about 2 g/L to 3 g/L, about 2 g/L to 4 g/L, about 2 g/L to 5 g/L, about 2 g/L to 6 g/L, about 2 g/L to 7 g/L, about 2 g/L to 8 g/L, about 2 g/L to 9 g/L, about 2 g/L to 10 g/L, about 2 g/L to 11 g/L, about 2 g/L to 12 g/L, about 2 g/L to 13 g/L, about 2 g/L to 14 g/L, about 2 g/L to 15 g/L, about 3 g/L to 4 g/L, about 3 g/L to 5 g/L, about 3 g/L to 6 g/L, about 3 g/L to 7 g/L, about 3 g/L to 8 g/L, about 3 g/L to 9 g/L, about 3 g/L to 10 g/L, about 3 g/L to 11 g/L, about 3 g/L to 12 g/L, about 3 g/L to 13 g/L, about 3 g/L to 14 g/L, about 3 g/L to 15 g/L, about 4 g/L to 5 g/L, about 4 g/L to 6 g/L, about 4 g/L to 7 g/L, about 4 g/L to 8 g/L, about 4 g/L to 9 g/L, about 4 g/L to 10 g/L, about 4 g/L to 11 g/L, about 4 g/L to 12 g/L, about 4 g/L to 13 g/L, about 4 g/L to 14 g/L, about 4 g/L to 15 g/L, about 5 g/L to 6 g/L, about 5 g/L to 7 g/L, about 5 g/L to 8 g/L, about 5 g/L to 9 g/L, about 5 g/L to 10 g/L, about 5 g/L to 11 g/L, about 5 g/L to 12 g/L, about 5 g/L to 13 g/L, about 5 g/L to 14 g/L, about 5 g/L to 15 g/L, about 6 g/L to 7 g/L, about 6 g/L to 8 g/L, about 6 g/L to 9 g/L, about 6 g/L to 10 g/L, about 6 g/L to 11 g/L, about 6 g/L to 12 g/L, about 6 g/L to 13 g/L, about 6 g/L to 14 g/L, about 6 g/L to 15 g/L, about 7 g/L to 8 g/L, about 7 g/L to 9 g/L, about 7 g/L to 10 g/L, about 7 g/L to 11 g/L, about 7 g/L to 12 g/L, about 7 g/L to 13 g/L, about 7 g/L to 14 g/L, about 7 g/L to 15 g/L, about 8 g/L to 9 g/L, about 8 g/L to 10 g/L, about 8 g/L to 11 g/L, about 8 g/L to 12 g/L, about 8 g/L to 13 g/L, about 8 g/L to 14 g/L, about 8 g/L to 15 g/L, about 9 g/L to 10 g/L, about 9 g/L to 11 g/L, about 9 g/L to 12 g/L, about 9 g/L to 13 g/L, about 9 g/L to 14 g/L, about 9 g/L to 15 g/L, about 10 g/L to 11 g/L, about 10 g/L to 12 g/L, about 10 g/L to 13 g/L, about 10 g/L to 14 g/L, about 10 g/L to 15 g/L, about 11 g/L to 12 g/L, about 11 g/L to 13 g/L, about 11 g/L to 14 g/L, about 11 g/L to 15 g/L, about 12 g/L to 13 g/L, about 12 g/L to 14 g/L, about 12 g/L to 15 g/L, about 13 g/L to 14 g/L, about 13 g/L to 15 g/L, or about 14 g/L to 15 g/L.

An enrichment media typically comprises a growth promoting agent. Non-limiting examples of a growth promoting agent is an iron containing compound that can be used by a pathogen of interest as an iron source. In an aspect of this embodiment, a growth promoting agent is ammonium ferric citrate.

Any concentration of ammonium ferric citrate may be used, with the proviso that the concentration is useful to practice the methods disclosed herein. In aspects of this embodiment, ammonium ferric citrate may be used at a concentration of, e.g., about 0.01 mg/mL, about 0.02 mg/mL, about 0.03 mg/mL, about 0.04 mg/mL, about 0.05 mg/mL, about 0.06 mg/mL, about 0.07 mg/mL, about 0.08 mg/mL, about 0.09 mg/mL, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1.0 mg/mL, about 2.0 mg/mL, about 3.0 mg/mL, about 4.0 mg/mL, about 5.0 mg/mL, about 6.0 mg/mL, about 7.0 mg/mL, about 8.0 mg/mL, about 9.0 mg/mL, about 10 mg/mL, about 11 mg/mL, about 12 mg/mL, about 13 mg/mL, about 14 mg/mL, or about 15 mg/mL. In other aspects of this embodiment, ammonium ferric citrate may be used at a concentration of, e.g., at least 0.01 mg/mL, at least 0.02 mg/mL, at least 0.03 mg/mL, at least 0.04 mg/mL, at least 0.05 mg/mL, at least 0.06 mg/mL, at least 0.07 mg/mL, at least 0.08 mg/mL, at least 0.09 mg/mL, at least 0.1 mg/mL, at least 0.2 mg/mL, at least 0.3 mg/mL, at least 0.4 mg/mL, at least 0.5 mg/mL, at least 0.6 mg/mL, at least 0.7 mg/mL, at least 0.8 mg/mL, at least 0.9 mg/mL, at least 1.0 mg/mL, at least 2.0 mg/mL, at least 3.0 mg/mL, at least 4.0 mg/mL, at least 5.0 mg/mL, at least 6.0 mg/mL, at least 7.0 mg/mL, at least 8.0 mg/mL, at least 9.0 mg/mL, at least 10 mg/mL, at least 11 mg/mL, at least 12 mg/mL, at least 13 mg/mL, at least 14 mg/mL, or at least 15 mg/mL. In yet other aspects of this embodiment, ammonium ferric citrate may be used at a concentration of, e.g., at most 0.01 mg/mL, at most 0.02 mg/mL, at most 0.03 mg/mL, at most 0.04 mg/mL, at most 0.05 mg/mL, at most 0.06 mg/mL, at most 0.07 mg/mL, at most 0.08 mg/mL, at most 0.09 mg/mL, at most 0.1 mg/mL, at most 0.2 mg/mL, at most 0.3 mg/mL, at most 0.4 mg/mL, at most 0.5 mg/mL, at most 0.6 mg/mL, at most 0.7 mg/mL, at most 0.8 mg/mL, at most 0.9 mg/mL, at most 1.0 mg/mL, at most 2.0 mg/mL, at most 3.0 mg/mL, at most 4.0 mg/mL, at most 5.0 mg/mL, at most 6.0 mg/mL, at most 7.0 mg/mL, at most 8.0 mg/mL, at most 9.0 mg/mL, at most 10 mg/mL, at most 11 mg/mL, at most 12 mg/mL, at most 13 mg/mL, at most 14 mg/mL, or at most 15 mg/mL.

In still other aspects of this embodiment, ammonium ferric citrate may be used at a concentration of, e.g., about 0.01 mg/mL to about 0.05 mg/mL about 0.01 mg/mL to about 0.1 mg/mL, about 0.01 mg/mL to about 0.5 mg/mL, about 0.05 mg/mL to about 0.1 mg/mL, about 0.05 mg/mL to about 0.5 mg/mL, about 0.05 mg/mL to about 1.0 mg/mL, about 0.05 mg/mL to about 5.0 mg/mL, about 0.1 mg/mL to about 0.5 mg/mL, about 0.1 mg/mL to about 1.0 mg/mL, about 0.1 mg/mL to about 5.0 mg/mL, about 0.1 mg/mL to about 10 mg/mL, about 0.1 mg/mL to about 15 mg/mL, about 0.5 mg/mL to about 1.0 mg/mL, about 0.5 mg/mL to about 5.0 mg/mL, about 0.5 mg/mL to about 10 mg/mL, about 0.5 mg/mL to about 15 mg/mL, about 1.0 mg/mL to about 5.0 mg/mL, about 1.0 mg/mL to about 10 mg/mL, about 1.0 mg/mL to about 15 mg/mL, about 5.0 mg/mL to about 10 mg/mL, about 5.0 mg/mL to about 15 mg/mL, or about 10 mg/mL to about 15 mg/mL.

An enrichment media typically comprises a growth enhancing agent as disclosed herein in the concentration ranges disclosed herein.

In an embodiment, an enrichment media comprises 6 g/L to 10 g/L of a peptone, 3 g/L to 7 g/L Bile Salts, 2 g/L to 6 g/L Meat Extract, 2 g/L to 6 g/L of a first growth inhibiting agent, 2 g/L to 6 g/L of a second growth inhibiting agent, 0.001 g/L to 0.008 g/L of a third growth inhibiting agent, and 0.001 g/L to 0.008 g/L of a fourth growth inhibiting agent. In aspects of this embodiment, an enrichment media comprises 6 g/L to 10 g/L of a Caseine peptone, 3 g/L to 7 g/L of Bile Salts, 2 g/L to 6 g/L of Meat Extract, 2 g/L to 6 g/L of a first iodine compound, 2 g/L to 6 g/L of a second iodine compound, 0.001 g/L to 0.008 g/L of an aminocoumarin antibiotic, and 0.001 g/L to 0.008 g/L of a triarylmethane dye. In still other aspects of this embodiment, an enrichment media comprises 6 g/L to 10 g/L of a Caseine peptone, 3 g/L to 7 g/L of Bile Salts, 2 g/L to 6 g/L of Meat Extract, 2 g/L to 6 g/L of a Iodine, 2 g/L to 6 g/L of a Potassium Iodide, 0.001 g/L to 0.008 g/L of Novobiocin, and 0.001 g/L to 0.008 g/L of Brilliant Green.

In an embodiment, an enrichment media comprises 7.5 g/L to 8.5 g/L of a peptone, 4 g/L to 6 g/L Bile Salts, 3 g/L to 5 g/L Meat Extract, 3 g/L to 5 g/L of a first growth inhibiting agent, 3 g/L to 5 g/L of a second growth inhibiting agent, 0.002 g/L to 0.006 g/L of a third growth inhibiting agent, and 0.002 g/L to 0.006 g/L of a fourth growth inhibiting agent. In aspects of this embodiment, an enrichment media comprises 7.5 g/L to 8.5 g/L of a Caseine peptone, 4 g/L to 6 g/L of Bile Salts, 3 g/L to 5 g/L of Meat Extract, 3 g/L to 5 g/L of a first iodine compound, 3 g/L to 5 g/L of a second iodine compound, 0.002 g/L to 0.006 g/L of an aminocoumarin antibiotic, and 0.002 g/L to 0.006 g/L of a triarylmethane dye. In still other aspects of this embodiment, an enrichment media comprises 7.5 g/L to 8.5 g/L of a Caseine peptone, 4 g/L to 6 g/L of Bile Salts, 3 g/L to 5 g/L g/L of Meat Extract, 3 g/L to 5 g/L of a Iodine, 1 g/L to 3 g/L of a Potassium Iodide, 0.002 g/L to 0.006 g/L of Novobiocin, and 0.002 g/L to 0.006 g/L of Brilliant Green.

In an embodiment, an enrichment media comprises 8.3 g/L to 8.9 g/L of a peptone, 4.4 g/L to 5.0 g/L Bile Salts, 4.0 g/L to 4.6 g/L Meat Extract, 3.7 g/L to 4.3 g/L of a first growth inhibiting agent, 3.7 g/L to 4.3 g/L of a second growth inhibiting agent, 0.003 g/L to 0.005 g/L of a third growth inhibiting agent, and 0.003 g/L to 0.005 g/L of a fourth growth inhibiting agent. In aspects of this embodiment, an enrichment media comprises 8.3 g/L to 8.9 g/L of a Caseine peptone, 4.4 g/L to 5.0 g/L of Bile Salts, 4.0 g/L to 4.6 g/L of Meat Extract, 3.7 g/L to 4.3 g/L of a first iodine compound, 3.7 g/L to 4.3 g/L of a second iodine compound, 0.003 g/L to 0.005 g/L of an aminocoumarin antibiotic, and 0.003 g/L to 0.005 g/L of a triarylmethane dye. In still other aspects of this embodiment, an enrichment media comprises 8.3 g/L to 8.9 g/L of a Caseine peptone, 4.4 g/L to 5.0 g/L of Bile Salts, 4.0 g/L to 4.6 g/L of Meat Extract, 3.7 g/L to 4.3 g/L of a Iodine, 3.7 g/L to 4.3 g/L of a Potassium Iodide, 0.003 g/L to 0.005 g/L of Novobiocin, and 0.003 g/L to 0.005 g/L of Brilliant Green.

In an embodiment, a pre-enrichment media comprises 8.6 g/L of a peptone, 4.7 g/L Bile Salts, 4.3 g/L Meat Extract, 4 g/L of a first growth inhibiting agent, 4 g/L of a second growth inhibiting agent, 0.004 g/L of a third growth inhibiting agent, and 0.004 g/L of a fourth growth inhibiting agent. In aspects of this embodiment, a pre-enrichment media comprises 8.6 g/L of a Caseine peptone, 4.7 g/L of Bile Salts, 4.3 g/L of Meat Extract, 4 g/L of a first iodine compound, 4 g/L of a second iodine compound, 0.004 g/L of an aminocoumarin antibiotic, and 0.004 g/L of a triarylmethane dye. In still other aspects of this embodiment, an enrichment media comprises 8.6 g/L of a Caseine peptone, 4.7 g/L of Bile Salts, 4.3 g/L of Meat Extract, 4 g/L of a Iodine, 4 g/L of a Potassium Iodide, 0.004 g/L of Novobiocin, and 0.004 g/L of Brilliant Green.

In another embodiment, a pre-enrichment media further comprises salts. In aspects of this embodiment, an enrichment media further comprises NaCl, $CaCO_3$ and $Na_2S_2O_3$. In other aspects of this embodiment, an enrichment media further comprises 1.3 g/L to 3.9 g/L NaCl, 37.4 g/L to 40.0 g/L $CaCO_3$ and 29.2 g/L to 31.8 g/L $Na_2S_2O_3$. In yet other aspects of this embodiment, an enrichment media further comprises 2.3 g/L to 2.9 g/L NaCl, 38.4 g/L to 39.0 g/L $CaCO_3$ and 30.2 g/L to 30.8 g/L $Na_2S_2O_3$. In still other aspects of this embodiment, an enrichment media further comprises 2.6 g/L NaCl, 38.7 g/L $CaCO_3$ and 30.5 g/L $Na_2S_2O_3$.

In another embodiment, an enrichment media comprises 4.5 g/L Soy Peptone, 7.2 g/L Sodium Chloride, 1.26 g/L Potassium Phosphate (monobasic), 0.18 g/L Potassium Phosphate (dibasic), 13.58 g/L Magnesium Chloride (anhydrous), 0.036 g/L Malachite Green, and 0.62 g/L Ammonium Ferric Citrate. In aspects of this embodiment, an enrichment media comprises 4.5 g/L Soy Peptone, 7.2 g/L Sodium Chloride, 1.26 g/L Potassium Phosphate (monobasic), 0.18 g/L Potassium Phosphate (dibasic), 29.0 g/L Magnesium Chloride (hexahydrate), 0.036 g/L Malachite Green, and 0.62 g/L Ammonium Ferric Citrate.

Aspect of the present specification disclose, in part, incubation of an aliquiot of pre-enrichment media in an enrichment media. Incubation of an aliquiot of pre-enrichment media is performed under temperature and time parameters that facilitate the growth of the pathogen in the sample, retard the growth of an unwanted organism in the sample, and/or establish conditions that otherwise increase the population of the pathogen in the sample and/or retard the growth of an unwanted organism in the sample. Incubation of enrichment media may be performed under constant rotation, reversal or agitation.

Any temperature may be used during incubation of an aliquiot of pre-enrichment media in an enrichment media, with the proviso that the temperature is useful to practice the methods disclosed herein. In aspects of this embodiment, a temperature used to incubate an aliquiot of pre-enrichment media in an enrichment media may be, e.g., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., or about 50° C. In other aspects of this embodiment, a temperature used to incubate an aliquiot of pre-enrichment media in an enrichment media may be, e.g., at least 15° C., at least 16° C., at least 17° C., at least 18° C., at least 19° C., at least 20° C., at least 21° C., at least 22° C., at least 23° C., at least 24° C., at least 25° C., at least 26° C., at least 27° C., at least 28° C., at least 29° C., at least 30° C., at least 31° C., at least 32° C., at least 33° C., at least 34° C., at least 35° C., at least 36° C., at least 37° C., at least 38° C., at least 39° C., at least 40° C., at least 41° C., at least 42° C., at least 43° C., at least 44° C., at least 45° C., at least 46° C., at least 47° C., at least 48° C., at least 49° C., or at least 50° C. In yet other aspects of this embodiment, a temperature used to incubate an aliquiot of pre-enrichment media in an enrichment media may be, e.g., at most 15° C., at most 16° C., at most 17° C., at most 18° C., at most 19° C., at most 20° C., at most 21° C., at most 22° C., at most 23° C., at most 24° C., at most 25° C., at most 26° C., at most 27° C., at most 28° C., at most 29° C., at most 30° C., at most 31° C., at most 32° C., at most 33° C., at most 34° C., at most 35° C., at most 36° C., at most 37° C., at most 38° C., at most 39° C., at most 40° C., at most 41° C., at most 42° C., at most 43° C., at most 44° C., at most 45° C., at most 46° C., at most 47° C., at most 48° C., at most 49° C., or at most 50° C. In still other aspects of this embodiment, a temperature used to incubate an aliquot of pre-enrichment media in an enrichment media may be, e.g., about 15° C. to about 19° C., about 16° C. to about 20° C., about 17° C. to about 21° C., about 18° C. to about 22° C., about 19° C. to about 23° C., about 20° C. to about 24° C., about 21° C. to about 25° C., about 22° C. to about 26° C., about 23° C. to about 27° C., about 24° C. to about 28° C., about 25° C. to about 29° C., about 26° C. to about 30° C., about 27° C. to about 31° C., about 28° C. to about 32° C., about 29° C. to about 33° C., about 30° C. to about 34° C., about 31° C. to about 35° C., about 32° C. to about 36° C., about 33° C. to about 37° C., about 34° C. to about 38° C., about 35° C. to about 39° C., about 36° C. to about 40° C., about 37° C. to about 41° C., about 38° C. to about 42° C., about 39° C. to about 43° C., about 40° C. to about 44° C., about 41° C. to about 45° C., about 42° C. to about 46° C., about 43° C. to about 47° C., about 44° C. to about 48° C., about 45° C. to about 49° C., about 46° C. to about 50° C., about 47° C. to about 51° C., about 48° C. to about 52° C., about 49° C. to about 53° C., or about 50° C. to about 54° C. In still other aspects of this embodiment, a temperature used to incubate of a sample in a pre-enrichment media may be, e.g., about 34° C. to about 39° C., about 34° C. to about 40° C., about 35° C. to about 45° C., about 36° C. to about 44° C., about 36° C. to about 43° C., about 37° C. to about 42° C., about 34° C. to about 45° C. or about 39° C. to about 45° C.

Any time may be used during incubation of an aliquot of pre-enrichment media in an enrichment media, with the proviso that the time is useful to practice the methods disclosed herein. In aspects of this embodiment, a time used to incubate an aliquot of pre-enrichment media in an enrichment media may be, e.g., about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In other aspects of this embodiment, a time used to incubate an aliquot of pre-enrichment media in an enrichment media may be, e.g., at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, or at least 24 hours. In yet other aspects of this embodiment, a time used to incubate an aliquot of pre-enrichment media in an enrichment media may be, e.g., at most 2 hours, at most 3 hours, at most 4 hours, at most 5 hours, at most 6 hours, at most 7 hours, at most 8 hours, at most 9 hours, at most 10 hours, at most 11 hours, at most 12 hours, at most 13 hours, at most 14 hours, at most 15 hours, at most 16 hours, at most 17 hours, at most 18 hours, at most 19 hours, at most 20 hours, at most 21 hours, at most 22 hours, at most 23 hours, or at most 24 hours. In yet other aspects of this embodiment, a time used to incubate an aliquot of pre-enrichment media in an enrichment media may be, e.g., about 2 hours to about 4 hours, about 3 hours to about 5 hours, about 4 hours to about 6 hours, about 5 hours to about 7 hours, about 6 hours to about 8 hours, about 7 hours to about 9 hours, about 8 hours to about 10 hours, about 9 hours to about 11 hours, about 10 hours to about 12 hours, about 11 hours to about 13 hours, about 12 hours to about 14 hours, about 13 hours to about 15 hours, about 14 hours to about 16 hours, about 15 hours to about 17 hours, about 16 hours to about 18 hours, about 17 hours to about 19 hours, about 18 hours to about 20 hours, about 19 hours to about 21 hours, about 20 hours to about 22 hours, about 21 hours to about 23 hours, about 22 hours to about 24 hours, about 23 hours to about 25 hours, or about 24 hours to about 26 hours. In yet other aspects of this embodiment, a time used to incubate an aliquot of pre-enrichment media in an enrichment media may be, e.g., about 12 hours to about 20 hours, about 13 hours to about 19 hours, about 14 hours to about 18 hours, about 15 hours to about 17 hours, about 12 hours to about 22 hours, about 13 hours to about 21 hours, about 14 hours to about 20 hours, about 15 hours to about 19 hours, about 16 hours to about 18 hours, about 13 hours to about 23 hours, about 14 hours to about 22 hours, about 15 hours to about 21 hours, about 16 hours to about 20 hours or about 17 hours to about 19 hours.

In aspects of this embodiment, an aliquot of pre-enrichment media in an enrichment media may be incubated at a temperature of, e.g., about 34° C. to about 39° C., about 34° C. to about 40° C., about 35° C. to about 45° C., about 36° C. to about 44° C., about 36° C. to about 43° C., about 37° C. to about 42° C., about 35° C. to about 39° C., about 34° C. to about 45° C. or about 39° C. to about 45° C. for a time of, e.g., about 12 hours to about 20 hours, about 13 hours to about 19 hours, about 14 hours to about 18 hours, about 15 hours to about 17 hours, about 12 hours to about 22 hours, about 13 hours to about 21 hours, about 14 hours to about 20 hours, about 15 hours to about 19 hours, about 16 hours to about 18 hours, about 13 hours to about 23 hours, about 14 hours to about 22 hours, about 15 hours to about 21 hours, about 16 hours to about 20 hours or about 17 hours to about 19 hours. Incubation of pre-enrichment media may be performed under constant rotation, reversal or agitation.

In aspects of this embodiment, an aliquot of pre-enrichment media in an enrichment media may be incubated at a temperature of, e.g., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., or about 50° C. for a time of, e.g., about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. Incubation of the enrichment media may be under constant rotation, reversal or agitation.

In other aspects of this embodiment, an aliquot of pre-enrichment media in an enrichment media may be incubated at a temperature of, e.g., at least 15° C., at least 16° C., at least 17° C., at least 18° C., at least 19° C., at least 20° C., at least 21° C., at least 22° C., at least 23° C., at least 24° C., at least 25° C., at least 26° C., at least 27° C., at least 28° C., at least 29° C., at least 30° C., at least 31° C., at least 32° C., at least 33° C., at least 34° C., at least 35° C., at least 36° C., at least 37° C., at least 38° C., at least 39° C., at least 40° C., at least 41° C., at least 42° C., at least 43° C., at least 44° C., at least 45° C., at least 46° C., at least 47° C., at least 48° C., at least 49° C., or at least 50° C. for a time of, e.g., at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, or at least 24 hours. Incubation of the enrichment media may be under constant rotation, reversal or agitation.

In yet other aspects of this embodiment, an aliquiot of pre-enrichment media in an enrichment media may be incubated at a temperature of, e.g., at most 15° C., at most 16° C., at most 17° C., at most 18° C., at most 19° C., at most 20° C., at most 21° C., at most 22° C., at most 23° C., at most 24° C., at most 25° C., at most 26° C., at most 27° C., at most 28° C., at most 29° C., at most 30° C., at most 31° C., at most 32° C., at most 33° C., at most 34° C., at most 35° C., at most 36° C., at most 37° C., at most 38° C., at most 39° C., at most 40° C., at most 41° C., at most 42° C., at most 43° C., at most 44° C., at most 45° C., at most 46° C., at most 47° C., at most 48° C., at most 49° C., or at most 50° C. for a time of, e.g., at most 2 hours, at most 3 hours, at most 4 hours, at most 5 hours, at most 6 hours, at most 7 hours, at most 8 hours, at most 9 hours, at most 10 hours, at most 11 hours, at most 12 hours, at most 13 hours, at most 14 hours, at most 15 hours, at most 16 hours, at most 17 hours, at most 18 hours, at most 19 hours, at most 20 hours, at most 21 hours, at most 22 hours, at most 23 hours, or at most 24 hours. Incubation of the enrichment media may be under constant rotation, reversal or agitation.

In still other aspects of this embodiment, an aliquiot of pre-enrichment media in an enrichment media may be incubated at a temperature of, e.g., about 15° C. to about 19° C., about 16° C. to about 20° C., about 17° C. to about 21° C., about 18° C. to about 22° C., about 19° C. to about 23° C., about 20° C. to about 24° C., about 21° C. to about 25° C., about 22° C. to about 26° C., about 23° C. to about 27° C., about 24° C. to about 28° C., about 25° C. to about 29° C., about 26° C. to about 30° C., about 27° C. to about 31° C., about 28° C. to about 32° C., about 29° C. to about 33° C., about 30° C. to about 34° C., about 31° C. to about 35° C., about 32° C. to about 36° C., about 33° C. to about 37° C., about 34° C. to about 38° C., about 35° C. to about 39° C., about 36° C. to about 40° C., about 37° C. to about 41° C., about 38° C. to about 42° C., about 39° C. to about 43° C., about 40° C. to about 44° C., about 41° C. to about 45° C., about 42° C. to about 46° C., about 43° C. to about 47° C., about 44° C. to about 48° C., about 45° C. to about 49° C., about 46° C. to about 50° C., about 47° C. to about 51° C., about 48° C. to about 52° C., about 49° C. to about 53° C., or about 50° C. to about 54° C. for a time of, e.g., about 2 hours to about 4 hours, about 3 hours to about 5 hours, about 4 hours to about 6 hours, about 5 hours to about 7 hours, about 6 hours to about 8 hours, about 7 hours to about 9 hours, about 8 hours to about 10 hours, about 9 hours to about 11 hours, about 10 hours to about 12 hours, about 11 hours to about 13 hours, about 12 hours to about 14 hours, about 13 hours to about 15 hours, about 14 hours to about 16 hours, about 15 hours to about 17 hours, about 16 hours to about 18 hours, about 17 hours to about 19 hours, about 18 hours to about 20 hours, about 19 hours to about 21 hours, about 20 hours to about 22 hours, about 21 hours to about 23 hours, about 22 hours to about 24 hours, about 23 hours to about 25 hours, or about 24 hours to about 26 hours. Incubation of the enrichment media may be under constant rotation, reversal or agitation.

Aspect of the present specification disclose, in part, a purification step. A pathogen may be subsequently purified after one or more incubation steps. For example, a pathogen may be purified after incubation in an enrichment media and/or after incubation in a second pre-enrichment media. Purification of a pathogen includes capture of the pathogen to a more concentrated form and/or removal contaminating microorganism, impurities, and debris. As such a purification step disclosed herein increases detection of a pathogen by increasing the concentration of pathogen and/or decreasing contaminants, thereby increasing the level of detectable signal measured in a subsequent detection step. Common purification procedures used to capture a pathogen and/or remove contaminating microorganism, impurities, and debris include affinity chromatography, ion-exchange chromatography, size exclusion chromatography, hydrophobic-interaction chromatography, ceramic hydroxyapatite chromatography, reverse-phase HPLC, gel filtration, precipitation, immuno-precipitation, diafiltration, chromato-focusing.

In one embodiment, a pathogen is purified after an inclubation step using an immuno-precipitation using antibodies or aptamers for a pathogen of interest. Immunoprecipitation is the technique of precipitating an antigen out of solution using an antibody or aptamer that specifically binds to that antigen. Immunoprecipitation requires that the antibody be coupled to a solid substrate at some point in the procedure. This is typically done using standard coupling procedures known in the art. Examples of solid substrates include agarose particles and magnetic particles. In aspects of this embodiment, the immuno-precipitation method employs antibodies or aptamers for a pathogen linked to magnetic particles.

Any concentration of magnetic particles linked with an antibody or apatmer may be used during its incubation during a purification step, with the proviso that the concentration is useful to practice the methods disclosed herein. In aspects of this embodiment, a concentration of magnetic particles linked with an antibody or apatmer used during a purification step may be, e.g., about $1 \times 10^4$ immunmagnetic particles/mL of media comprising the pathogen of interest, about $1 \times 10^5$ immunmagnetic particles/mL of media comprising the pathogen of interest, about $1 \times 10^6$ immunmagnetic particles/mL of media comprising the pathogen of interest, about $1 \times 10^7$ immunmagnetic particles/mL of media comprising the pathogen of interest, or about $1 \times 10^8$ immunmagnetic particles/mL of media comprising the pathogen of interest. In other aspects of this embodiment, a concentration of magnetic particles linked with an antibody or apatmer used during a purification step may be, e.g., at least $1 \times 10^4$ immunmagnetic particles/mL of media comprising the pathogen of interest, at least $1 \times 10^5$ immunmagnetic particles/mL of media comprising the pathogen of interest, at least $1 \times 10^6$ immunmagnetic particles/mL of media comprising the pathogen of interest, at least $1 \times 10^7$ immunmagnetic particles/mL of media comprising the pathogen of interest, or at least $1 \times 10^8$ immunmagnetic particles/mL of media comprising the pathogen of interest. In yet other aspects of this embodiment, a concentration of magnetic particles linked with an antibody or apatmer used during a purification step may be, e.g., at most $1 \times 10^4$ immunmagnetic particles/mL of media comprising the pathogen of interest, at most $1 \times 10^5$ immunmagnetic particles/mL of media comprising the pathogen of interest, at most $1 \times 10^6$ immunmagnetic particles/mL of media comprising the pathogen of interest, at most 1×10⁷ immunmagnetic particles/mL of media comprising the pathogen of interest, or at most 1×10⁸ immunmagnetic particles/mL of media comprising the pathogen of interest.

In still other aspects of this embodiment, a concentration of magnetic particles linked with an antibody or apatmer used during a purification step may be, e.g., about 1×10⁴ to about 1×10⁵ immunmagnetic particles/mL of media comprising the pathogen of interest, about 1×10⁴ to about 1×10⁶ immunmagnetic particles/mL of media comprising the pathogen of interest, about 1×10⁴ to about 1×10⁷ immunmagnetic particles/mL of media comprising the pathogen of interest, about 1×10⁴ to about 1×10⁸ immunmagnetic particles/mL of media comprising the pathogen of interest, about 1×10⁵ to about 1×10⁶ immunmagnetic particles/mL of media comprising the pathogen of interest, about 1×10⁵ to about 1×10⁷ immunmagnetic particles/mL of media comprising the pathogen of interest, about 1×10⁵ to about 1×10⁸ immunmagnetic particles/mL of media comprising the pathogen of interest, about 1×10⁶ to about 1×10⁷ immunmagnetic particles/mL of media comprising the pathogen of interest, about 1×10⁶ to about 1×10⁸ immunmagnetic particles/mL of media comprising the pathogen of interest, or about 1×10⁷ to about 1×10⁸ immunmagnetic particles/mL of media comprising the pathogen of interest.

Aspect of the present specification disclose, in part, incubation of immunmagnetic particles with media comprising the pathogen of interest. Incubation of immunmagnetic particles with media comprising the pathogen of interest is performed under temperature and time parameters that facilitate binding of the pathogen to the magnetic particles linked with an antibody or apatmer for the pathogen of interest. Incubation of immunmagnetic particles with media comprising the pathogen of interest may be performed under agitation/rotation.

Any temperature may be used during incubation of immunmagnetic particles with media comprising the pathogen of interest, with the proviso that the temperature is useful to practice the methods disclosed herein. In aspects of this embodiment, a temperature used to incubate immunmagnetic particles with media comprising the pathogen of interest may be, e.g., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., or about 50° C. In other aspects of this embodiment, a temperature used to incubate immunmagnetic particles with media comprising the pathogen of interest may be, e.g., at least 15° C., at least 16° C., at least 17° C., at least 18° C., at least 19° C., at least 20° C., at least 21° C., at least 22° C., at least 23° C., at least 24° C., at least 25° C., at least 26° C., at least 27° C., at least 28° C., at least 29° C., at least 30° C., at least 31° C., at least 32° C., at least 33° C., at least 34° C., at least 35° C., at least 36° C., at least 37° C., at least 38° C., at least 39° C., at least 40° C., at least 41° C., at least 42° C., at least 43° C., at least 44° C., at least 45° C., at least 46° C., at least 47° C., at least 48° C., at least 49° C., or at least 50° C. In yet other aspects of this embodiment, a temperature used to incubate immunmagnetic particles with media comprising the pathogen of interest may be, e.g., at most 15° C., at most 16° C., at most 17° C., at most 18° C., at most 19° C., at most 20° C., at most 21° C., at most 22° C., at most 23° C., at most 24° C., at most 25° C., at most 26° C., at most 27° C., at most 28° C., at most 29° C., at most 30° C., at most 31° C., at most 32° C., at most 33° C., at most 34° C., at most 35° C., at most 36° C., at most 37° C., at most 38° C., at most 39° C., at most 40° C., at most 41° C., at most 42° C., at most 43° C., at most 44° C., at most 45° C., at most 46° C., at most 47° C., at most 48° C., at most 49° C., or at most 50° C. In still other aspects of this embodiment, a temperature used to incubate immunmagnetic particles with media comprising the pathogen of interest may be, e.g., about 15° C. to about 19° C., about 16° C. to about 20° C., about 17° C. to about 21° C., about 18° C. to about 22° C., about 19° C. to about 23° C., about 20° C. to about 24° C., about 21° C. to about 25° C., about 22° C. to about 26° C., about 23° C. to about 27° C., about 24° C. to about 28° C., about 25° C. to about 29° C., about 26° C. to about 30° C., about 27° C. to about 31° C., about 28° C. to about 32° C., about 29° C. to about 33° C., about 30° C. to about 34° C., about 31° C. to about 35° C., about 32° C. to about 36° C., about 33° C. to about 37° C., about 34° C. to about 38° C., about 35° C. to about 39° C., about 36° C. to about 40° C., about 37° C. to about 41° C., about 38° C. to about 42° C., about 39° C. to about 43° C., about 40° C. to about 44° C., about 41° C. to about 45° C., about 42° C. to about 46° C., about 43° C. to about 47° C., about 44° C. to about 48° C., about 45° C. to about 49° C., about 46° C. to about 50° C., about 47° C. to about 51° C., about 48° C. to about 52° C., about 49° C. to about 53° C., or about 50° C. to about 54° C. In other aspects of this embodiment, a temperature used to incubate immunmagnetic particles with media comprising the pathogen of interest may be, e.g., about 34° C. to about 39° C., about 34° C. to about 40° C., about 35° C. to about 45° C., about 36° C. to about 44° C., about 36° C. to about 43° C., about 37° C. to about 42° C., about 34° C. to about 45° C. or about 39° C. to about 45° C.

Any time may be used during incubation of immunmagnetic particles with media comprising the pathogen of interest, with the proviso that the time is useful to practice the methods disclosed herein. In aspects of this embodiment, a time used to incubate immunmagnetic particles with media comprising the pathogen of interest may be, e.g., about 5 minutes, about 10 minutes, about 15 minutes, about 20 minutes, about 30 minutes, about 40 minutes, about 50 minutes, about 60 minutes, about 70 minutes, about 80 minutes, about 90 minutes, about 100 minutes, about 110 minutes, about 120 minutes, about 130 minutes, about 140 minutes, or about 150 minutes. In other aspects of this embodiment, a time used to incubate immunmagnetic particles with media comprising the pathogen of interest may be, e.g., at least 5 minutes, at least 10 minutes, at least 15 minutes, at least 20 minutes, at least 30 minutes, at least 40 minutes, at least 50 minutes, at least 60 minutes, at least 70 minutes, at least 80 minutes, at least 90 minutes, at least 100 minutes, at least 110 minutes, at least 120 minutes, at least 130 minutes, at least 140 minutes, or at least 150 minutes. In yet other aspects of this embodiment, a time used to incubate immunmagnetic particles with media comprising the pathogen of interest may be, e.g., at most 5 minutes, at most 10 minutes, at most 15 minutes, at most 20 minutes, at most 30 minutes, at most 40 minutes, at most 50 minutes, at most 60 minutes, at most 70 minutes, at most 80 minutes, at most 90 minutes, at most 100 minutes, at most 110 minutes, at most 120 minutes, at most 130 minutes, at most 140 minutes, or at most 150 minutes.

In yet other aspects of this embodiment, a time used to incubate immunmagnetic particles with media comprising the pathogen of interest may be, e.g., about 5 minutes to about 20 minutes, about 5 minutes to about 30 minutes, about 5 minutes to about 40 minutes, about 5 minutes to about 50 minutes, about 5 minutes to about 60 minutes, about 5 minutes to about 70 minutes, about 5 minutes to about 80 minutes, about 5 minutes to about 90 minutes, about 5 minutes to about 100 minutes, about 5 minutes to about 110 minutes, about 5 minutes to about 120 minutes, about 5 minutes to about 130 minutes, about 5 minutes to about 140 minutes, about 5 minutes to about 150 minutes, about 10 minutes to about 20 minutes, about 10 minutes to about 30 minutes, about 10 minutes to about 40 minutes, about 10 minutes to about 50 minutes, about 10 minutes to about 60 minutes, about 10 minutes to about 70 minutes, about 10 minutes to about 80 minutes, about 10 minutes to about 90 minutes, about 10 minutes to about 100 minutes, about 10 minutes to about 110 minutes, about 10 minutes to about 120 minutes, about 10 minutes to about 130 minutes, about 10 minutes to about 140 minutes, about 10 minutes to about 150 minutes, about 20 minutes to about 30 minutes, about 20 minutes to about 40 minutes, about 20 minutes to about 50 minutes, about 20 minutes to about 60 minutes, about 20 minutes to about 70 minutes, about 20 minutes to about 80 minutes, about 20 minutes to about 90 minutes, about 20 minutes to about 100 minutes, about 20 minutes to about 110 minutes, about 20 minutes to about 120 minutes, about 20 minutes to about 130 minutes, about 20 minutes to about 140 minutes, about 20 minutes to about 150 minutes, about 30 minutes to about 40 minutes, about 30 minutes to about 50 minutes, about 30 minutes to about 60 minutes, about 30 minutes to about 70 minutes, about 30 minutes to about 80 minutes, about 30 minutes to about 90 minutes, about 30 minutes to about 100 minutes, about 30 minutes to about 110 minutes, about 30 minutes to about 120 minutes, about 30 minutes to about 130 minutes, about 30 minutes to about 140 minutes, about 30 minutes to about 150 minutes, about 60 minutes to about 70 minutes, about 60 minutes to about 80 minutes, about 60 minutes to about 90 minutes, about 60 minutes to about 100 minutes, about 60 minutes to about 110 minutes, about 60 minutes to about 120 minutes, about 60 minutes to about 130 minutes, about 60 minutes to about 140 minutes, about 60 minutes to about 150 minutes, about 90 minutes to about 100 minutes, about 90 minutes to about 110 minutes, about 90 minutes to about 120 minutes, about 90 minutes to about 130 minutes, about 90 minutes to about 140 minutes, about 90 minutes to about 150 minutes, about 120 minutes to about 130 minutes, about 120 minutes to about 140 minutes, or about 120 minutes to about 150 minutes.

In aspects of this embodiment, immunmagnetic particles may be incubated with media comprising the pathogen of interest at a temperature of, e.g., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., or about 50° C. for a time of, e.g., about 5 minutes, about 10 minutes, about 15 minutes, about 20 minutes, about 30 minutes, about 40 minutes, about 50 minutes, about 60 minutes, about 70 minutes, about 80 minutes, about 90 minutes, about 100 minutes, about 110 minutes, about 120 minutes, about 130 minutes, about 140 minutes, or about 150 minutes.

In other aspects of this embodiment, immunmagnetic particles may be incubated with media comprising the pathogen of interest at a temperature of, e.g., at least 15° C., at least 16° C., at least 17° C., at least 18° C., at least 19° C., at least 20° C., at least 21° C., at least 22° C., at least 23° C., at least 24° C., at least 25° C., at least 26° C., at least 27° C., at least 28° C., at least 29° C., at least 30° C., at least 31° C., at least 32° C., at least 33° C., at least 34° C., at least 35° C., at least 36° C., at least 37° C., at least 38° C., at least 39° C., at least 40° C., at least 41° C., at least 42° C., at least 43° C., at least 44° C., at least 45° C., at least 46° C., at least 47° C., at least 48° C., at least 49° C., or at least 50° C. for a time of, e.g., at least 5 minutes, at least 10 minutes, at least 15 minutes, at least 20 minutes, at least 30 minutes, at least 40 minutes, at least 50 minutes, at least 60 minutes, at least 70 minutes, at least 80 minutes, at least 90 minutes, at least 100 minutes, at least 110 minutes, at least 120 minutes, at least 130 minutes, at least 140 minutes, or at least 150 minutes.

In yet other aspects of this embodiment, immunmagnetic particles may be incubated with media comprising the pathogen of interest at a temperature of, e.g., at most 15° C., at most 16° C., at most 17° C., at most 18° C., at most 19° C., at most 20° C., at most 21° C., at most 22° C., at most 23° C., at most 24° C., at most 25° C., at most 26° C., at most 27° C., at most 28° C., at most 29° C., at most 30° C., at most 31° C., at most 32° C., at most 33° C., at most 34° C., at most 35° C., at most 36° C., at most 37° C., at most 38° C., at most 39° C., at most 40° C., at most 41° C., at most 42° C., at most 43° C., at most 44° C., at most 45° C., at most 46° C., at most 47° C., at most 48° C., at most 49° C., or at most 50° C. for a time of, e.g., at most 5 minutes, at most 10 minutes, at most 15 minutes, at most 20 minutes, at most 30 minutes, at most 40 minutes, at most 50 minutes, at most 60 minutes, at most 70 minutes, at most 80 minutes, at most 90 minutes, at most 100 minutes, at most 110 minutes, at most 120 minutes, at most 130 minutes, at most 140 minutes, or at most 150 minutes.

In still other aspects of this embodiment, immunmagnetic particles may be incubated with media comprising the pathogen of interest at a temperature of, e.g., about 15° C. to about 19° C., about 16° C. to about 20° C., about 17° C. to about 21° C., about 18° C. to about 22° C., about 19° C. to about 23° C., about 20° C. to about 24° C., about 21° C. to about 25° C., about 22° C. to about 26° C., about 23° C. to about 27° C., about 24° C. to about 28° C., about 25° C. to about 29° C., about 26° C. to about 30° C., about 27° C. to about 31° C., about 28° C. to about 32° C., about 29° C. to about 33° C., about 30° C. to about 34° C., about 31° C. to about 35° C., about 32° C. to about 36° C., about 33° C. to about 37° C., about 34° C. to about 38° C., about 35° C. to about 39° C., about 36° C. to about 40° C., about 37° C. to about 41° C., about 38° C. to about 42° C., about 39° C. to about 43° C., about 40° C. to about 44° C., about 41° C. to about 45° C., about 42° C. to about 46° C., about 43° C. to about 47° C., about 44° C. to about 48° C., about 45° C. to about 49° C., about 46° C. to about 50° C., about 47° C. to about 51° C., about 48° C. to about 52° C., about 49° C. to about 53° C., about 50° C. to about 54° C., about 34° C. to about 39° C., about 34° C. to about 40° C., about 35° C. to about 45° C., about 36° C. to about 44° C., about 36° C. to about 43° C., about 37° C. to about 42° C., about 34° C. to about 45° C. or about 39° C. to about 45° C. for a time of, e.g., about 5 minutes to about 20 minutes, about 5 minutes to about 30 minutes, about 5 minutes to about 40 minutes, about 5 minutes to about 50 minutes, about 5 minutes to about 60 minutes, about 5 minutes to about 70 minutes, about 5 minutes to about 80 minutes, about 5 minutes to about 90 minutes, about 5 minutes to about 100 minutes, about 5 minutes to about 110 minutes, about 5 minutes to about 120 minutes, about 5 minutes to about 130 minutes, about 5 minutes to about 140 minutes, about 5 minutes to about 150 minutes, about 10 minutes to about 20 minutes, about 10 minutes to about 30 minutes, about 10 minutes to about 40 minutes, about 10 minutes to about 50 minutes, about 10 minutes to about 60 minutes, about 10 minutes to about 70 minutes, about 10 minutes to about 80 minutes, about 10 minutes to about 90 minutes, about 10 minutes to about 100 minutes, about 10 minutes to about 110 minutes, about 10 minutes to about 120 minutes, about 10 minutes to about 130 minutes, about 10 minutes to about 140 minutes, about 10 minutes to about 150 minutes, about 20 minutes to about 30 minutes, about 20 minutes to about 40 minutes, about 20 minutes to about 50 minutes, about 20 minutes to about 60 minutes, about 20 minutes to about 70 minutes, about 20 minutes to about 80 minutes, about 20 minutes to about 90 minutes, about 20 minutes to about 100 minutes, about 20 minutes to about 110 minutes, about 20 minutes to about 120 minutes, about 20 minutes to about 130 minutes, about 20 minutes to about 140 minutes, about 20 minutes to about 150 minutes, about 30 minutes to about 40 minutes, about 30 minutes to about 50 minutes, about 30 minutes to about 60 minutes, about 30 minutes to about 70 minutes, about 30 minutes to about 80 minutes, about 30 minutes to about 90 minutes, about 30 minutes to about 100 minutes, about 30 minutes to about 110 minutes, about 30 minutes to about 120 minutes, about 30 minutes to about 130 minutes, about 30 minutes to about 140 minutes, about 30 minutes to about 150 minutes, about 60 minutes to about 70 minutes, about 60 minutes to about 80 minutes, about 60 minutes to about 90 minutes, about 60 minutes to about 100 minutes, about 60 minutes to about 110 minutes, about 60 minutes to about 120 minutes, about 60 minutes to about 130 minutes, about 60 minutes to about 140 minutes, about 60 minutes to about 150 minutes, about 90 minutes to about 100 minutes, about 90 minutes to about 110 minutes, about 90 minutes to about 120 minutes, about 90 minutes to about 130 minutes, about 90 minutes to about 140 minutes, about 90 minutes to about 150 minutes, about 120 minutes to about 130 minutes, about 120 minutes to about 140 minutes, or about 120 minutes to about 150 minutes.

After completion of incubation, the pathogen-bound immunoparticles may be isolated from the media. In aspects of this embodiment, immunoparticles may be isolated from the media using a magnetic separator which concentrates the immunoparticles in a specific location allowing for the media to be removed. Alternatively, immunoparticles may be isolated from the media by centrifuged to concentrate the immunoparticles, thereby allowing for the media to be removed. After removal of the media, the isolated Pathogen-bound immunoparticles may be washed one or more times using a buffered solution. Subsequent isolation of the immunoparticles may be accomplished using a magnetic separator or centrifugation and removal of the buffered solution.

However, a purification step disclosed herein is optional. Thus, in one embodiment, a method of detecting a pathogen disclosed herein does not comprise a purification of a pathogen from a pre-enrichment media, an enrichment media, or both a pre-enrichment media and an enrichment media. In another embodiment, a method of detecting a pathogen disclosed herein does not comprise a purification of a Pathogen from an enrichment media, a second pre-enrichment media, or both an enrichment media and a second pre-enrichment media. In another embodiment, a method of detecting a pathogen disclosed herein does not comprise a purification of a pathogen from a first pre-enrichment media.

Aspect of the present specification disclose, in part, a detection step. After being enriched, presence or absence of a pathogen of interest may be determined by qualitatively or quantitatively measuring the amount of pathogen contained within the media. In one embodiment, detection presence or absence of a pathogen of interest occurs without the need of a purification step disclosed herein. In one embodiment, detection presence or absence of a pathogen of interest occurs after completion of a purification step disclosed herein. However, media comprising a pathogen of interest may be processed to remove debris and other contaminants without any pathogen purification. In one embodiment, media comprising a pathogen of interest is centrifuged to remove debris. In another embodiment no such centrifugation step is required. In addition, use of a secondary antibody to boast a detection signal is optional. Thus, in one embodiment, a method of detecting a pathogen does not comprise use of a secondary antibody to boast a detection signal.

In aspects of this embodiment, a method disclosed herein may qualitatively or quantitatively detect pathogen having a concentration in a sample disclosed herein of, e.g., about $1\times10^{-5}$ cfu/mL, about $1\times10^{-4}$ cfu/mL, about $1\times10^{-3}$ cfu/mL, about $1\times10^{-2}$ cfu/mL, about $1\times10^{-1}$ cfu/mL, about $1\times10^{0}$ cfu/mL, about $1\times10^{1}$ cfu/mL, about $1\times10^{2}$ cfu/mL, about $1\times10^{3}$ cfu/mL, about $1\times10^{4}$ cfu/mL, about $1\times10^{5}$ cfu/mL, about $1\times10^{6}$ cfu/mL, about $1\times10^{7}$ cfu/mL, about $1\times10^{8}$ cfu/mL, about $1\times10^{9}$ cfu/mL, or about $1\times10^{10}$ cfu/mL. In other aspects of this embodiment, a method disclosed herein may qualitatively or quantitatively detect pathogen having a concentration in a sample disclosed herein of, e.g., at least $1\times10^{-5}$ cfu/mL, at least $1\times10^{-4}$ cfu/mL, at least $1\times10^{-3}$ cfu/mL, at least $1\times10^{-2}$ cfu/mL, at least $1\times10^{-1}$ cfu/mL, at least $1\times10^{0}$ cfu/mL, at least $1\times10^{1}$ cfu/mL, at least $1\times10^{2}$ cfu/mL, at least $1\times10^{3}$ cfu/mL, at least $1\times10^{4}$ cfu/mL, at least $1\times10^{5}$ cfu/mL, at least $1\times10^{6}$ cfu/mL, at least $1\times10^{7}$ cfu/mL, at least $1\times10^{8}$ cfu/mL, at least $1\times10^{9}$ cfu/mL, or at least $1\times10^{10}$ cfu/mL. In yet other aspects of this embodiment, a method disclosed herein may qualitatively or quantitatively detect pathogen having a concentration in a sample disclosed herein of, e.g., at most $1\times10^{-5}$ cfu/mL, at most $1\times10^{-4}$ cfu/mL, at most $1\times10^{-3}$ cfu/mL, at most $1\times10^{-2}$ cfu/mL, at most $1\times10^{-1}$ cfu/mL, at most $1\times10^{0}$ cfu/mL, at most $1\times10^{1}$ cfu/mL, at most $1\times10^{2}$ cfu/mL, at most $1\times10^{3}$ cfu/mL, at most $1\times10^{4}$ cfu/mL, at most $1\times10^{5}$ cfu/mL, at most $1\times10^{6}$ cfu/mL, at most $1\times10^{7}$ cfu/mL, at most $1\times10^{8}$ cfu/mL, at most $1\times10^{9}$ cfu/mL, or at most $1\times10^{10}$ cfu/mL.

In still other aspects of this embodiment, a method disclosed herein may qualitatively or quantitatively detect pathogen having a concentration in a sample disclosed herein of, e.g., about $1\times10^{-5}$ cfu/mL to about about $1\times10^{-4}$ cfu/mL, about $1\times10^{-5}$ cfu/mL to about $1\times10^{-3}$ cfu/mL, about $1\times10^{-5}$ cfu/mL to about about $1\times10^{-2}$ cfu/mL, about $1\times10^{-5}$ cfu/mL to about $1\times10^{-1}$ cfu/mL, about $1\times10^{-5}$ cfu/mL to about about $1\times10^{0}$ cfu/mL, about $1\times10^{-5}$ cfu/mL to about $1\times10^{-1}$ cfu/mL, about $1\times10^{-5}$ cfu/mL to about $1\times10^{2}$ cfu/mL, about $1\times10^{-5}$ cfu/mL to about $1\times10^{3}$ cfu/mL, about $1\times10^{-5}$ cfu/mL to about $1\times10^{4}$ cfu/mL, about $1\times10^{-5}$ cfu/mL to about $1\times10^{5}$ cfu/mL, about $1\times10^{-5}$ cfu/mL to about $1\times10^{6}$ cfu/mL, about $1\times10^{-5}$ cfu/mL to about $1\times10^{7}$ cfu/mL, about $1\times10^{-5}$ cfu/mL to about $1\times10^{8}$ cfu/mL, about $1\times10^{-5}$ cfu/mL to about $1\times10^{9}$ cfu/mL, about $1\times10^{-5}$ cfu/mL to about $1\times10^{10}$ cfu/mL, about $1\times10^{-4}$ cfu/mL to about $1\times10^{-3}$ cfu/mL, about $1\times10^{-4}$ cfu/mL to about $1\times10^{-2}$ cfu/mL, about $1\times10^{-4}$ cfu/mL to about $1\times10^{-1}$ cfu/mL, about $1\times10^{-4}$ cfu/mL to about $1\times10^{0}$ cfu/mL, about $1\times10^{-4}$ cfu/mL to about $1\times10^{1}$ cfu/mL, about $1\times10^{-4}$ cfu/mL to about $1\times10^{2}$ cfu/mL, about $1\times10^{-4}$ cfu/mL to about $1\times10^{3}$ cfu/mL, about $1\times10^{-4}$ cfu/mL to about $1\times10^4$ cfu/mL, about $1\times10^{-4}$ cfu/mL to about $1\times10^5$ cfu/mL, about $1\times10^{-4}$ cfu/mL to about $1\times10^6$ cfu/mL, about $1\times10^{-4}$ cfu/mL to about $1\times10^7$ cfu/mL, about $1\times10^{-4}$ cfu/mL to about $1\times10^8$ cfu/mL, about $1\times10^{-4}$ cfu/mL to about $1\times10^9$ cfu/mL, about $1\times10^{-4}$ cfu/mL to about $1\times10^{10}$ cfu/mL, about $1\times10^{-3}$ cfu/mL to about $1\times10^{-2}$ cfu/mL, about $1\times10^{-3}$ cfu/mL to about $1\times10^{-1}$ cfu/mL, about $1\times10^{-3}$ cfu/mL to about $1\times10^{0}$ cfu/mL, about $1\times10^{-3}$ cfu/mL to about $1\times10^1$ cfu/mL, about $1\times10^{-3}$ cfu/mL to about $1\times10^2$ cfu/mL, about $1\times10^{-3}$ cfu/mL to about $1\times10^3$ cfu/mL, about $1\times10^{-3}$ cfu/mL to about $1\times10^4$ cfu/mL, about $1\times10^{-3}$ cfu/mL to about $1\times10^5$ cfu/mL, about $1\times10^{-3}$ cfu/mL to about $1\times10^6$ cfu/mL, about $1\times10^{-3}$ cfu/mL to about $1\times10^7$ cfu/mL, about $1\times10^{-3}$ cfu/mL to about $1\times10^8$ cfu/mL, about $1\times10^{-3}$ cfu/mL to about $1\times10^9$ cfu/mL, about $1\times10^{-3}$ cfu/mL to about $1\times10^{10}$ cfu/mL, about $1\times10^{-2}$ cfu/mL to about $1\times10^{-1}$ cfu/mL, about $1\times10^{-2}$ cfu/mL to about $1\times10^{0}$ cfu/mL, about $1\times10^{-2}$ cfu/mL to about $1\times10^1$ cfu/mL, about $1\times10^{-2}$ cfu/mL to about $1\times10^2$ cfu/mL, about $1\times10^{-2}$ cfu/mL to about $1\times10^3$ cfu/mL, about $1\times10^{-2}$ cfu/mL to about $1\times10^4$ cfu/mL, about $1\times10^{-2}$ cfu/mL to about $1\times10^5$ cfu/mL, about $1\times10^{-2}$ cfu/mL to about $1\times10^6$ cfu/mL, about $1\times10^{-2}$ cfu/mL to about $1\times10^7$ cfu/mL, about $1\times10^{-2}$ cfu/mL to about $1\times10^8$ cfu/mL, about $1\times10^{-2}$ cfu/mL to about $1\times10^9$ cfu/mL, about $1\times10^{-2}$ cfu/mL to about $1\times10^{10}$ cfu/mL, about $1\times10^{-1}$ cfu/mL to about $1\times10^{0}$ cfu/mL, about $1\times10^{-1}$ cfu/mL to about $1\times10^1$ cfu/mL, about $1\times10^{-1}$ cfu/mL to about $1\times10^2$ cfu/mL, about $1\times10^{-1}$ cfu/mL to about $1\times10^3$ cfu/mL, about $1\times10^{-1}$ cfu/mL to about $1\times10^4$ cfu/mL, about $1\times10^{-1}$ cfu/mL to about $1\times10^5$ cfu/mL, about $1\times10^{-1}$ cfu/mL to about $1\times10^6$ cfu/mL, about $1\times10^{-1}$ cfu/mL to about $1\times10^7$ cfu/mL, about $1\times10^{-1}$ cfu/mL to about $1\times10^8$ cfu/mL, about $1\times10^{-1}$ cfu/mL to about $1\times10^9$ cfu/mL, about $1\times10^{-1}$ cfu/mL to about $1\times10^{10}$ cfu/mL, about $1\times10^{0}$ cfu/mL to about $1\times10^1$ cfu/mL, about $1\times10^{0}$ cfu/mL to about $1\times10^2$ cfu/mL, about $1\times10^{0}$ cfu/mL to about $1\times10^3$ cfu/mL, about $1\times10^{0}$ cfu/mL to about $1\times10^4$ cfu/mL, about $1\times10^{0}$ cfu/mL to about $1\times10^5$ cfu/mL, about $1\times10^{0}$ cfu/mL to about $1\times10^6$ cfu/mL, about $1\times10^{0}$ cfu/mL to about $1\times10^7$ cfu/mL, about $1\times10^{0}$ cfu/mL to about $1\times10^8$ cfu/mL, about $1\times10^{0}$ cfu/mL to about $1\times10^9$ cfu/mL, about $1\times10^{0}$ cfu/mL to about $1\times10^{10}$ cfu/mL, about $1\times10^1$ cfu/mL to about $1\times10^2$ cfu/mL, about $1\times10^1$ cfu/mL to about $1\times10^3$ cfu/mL, about $1\times10^1$ cfu/mL to about $1\times10^4$ cfu/mL, about $1\times10^1$ cfu/mL to about about $1\times10^5$ cfu/mL, about $1\times10^1$ cfu/mL to about about $1\times10^6$ cfu/mL, about $1\times10^1$ cfu/mL to about $1\times10^7$ cfu/mL, about $1\times10^1$ cfu/mL to about $1\times10^8$ cfu/mL, about $1\times10^1$ cfu/mL to about $1\times10^9$ cfu/mL, about $1\times10^1$ cfu/mL to about $1\times10^{10}$ cfu/mL, about $1\times10^2$ cfu/mL to about $1\times10^3$ cfu/mL, about $1\times10^2$ cfu/mL to about $1\times10^4$ cfu/mL, about $1\times10^2$ cfu/mL to about $1\times10^5$ cfu/mL, about $1\times10^2$ cfu/mL to about $1\times10^6$ cfu/mL, about $1\times10^2$ cfu/mL to about $1\times10^7$ cfu/mL, about $1\times10^2$ cfu/mL to about $1\times10^8$ cfu/mL, about $1\times10^2$ cfu/mL to about $1\times10^9$ cfu/mL, about $1\times10^2$ cfu/mL to about $1\times10^{10}$ cfu/mL, about $1\times10^3$ cfu/mL to about $1\times10^4$ cfu/mL, about $1\times10^3$ cfu/mL to about $1\times10^5$ cfu/mL, about $1\times10^3$ cfu/mL to about $1\times10^6$ cfu/mL, about $1\times10^3$ cfu/mL to about $1\times10^7$ cfu/mL, about $1\times10^3$ cfu/mL to about $1\times10^8$ cfu/mL, about $1\times10^3$ cfu/mL to about $1\times10^9$ cfu/mL, about $1\times10^3$ cfu/mL to about $1\times10^{10}$ cfu/mL, about $1\times10^4$ cfu/mL to about $1\times10^5$ cfu/mL, about $1\times10^4$ cfu/mL to about about $1\times10^6$ cfu/mL, about $1\times10^4$ cfu/mL to about $1\times10^7$ cfu/mL, about $1\times10^4$ cfu/mL to about $1\times10^8$ cfu/mL, about $1\times10^4$ cfu/mL to about $1\times10^9$ cfu/mL, or about $1\times10^4$ cfu/mL to about $1\times10^{10}$ cfu/mL.

In aspects of this embodiment, a method disclosed herein may qualitatively or quantitatively detect pathogen having a concentration after an pre-enrichment step of, e.g., about $1\times10^{-5}$ cfu/mL, about $1\times10^{-4}$ cfu/mL, about $1\times10^{-3}$ cfu/mL, about $1\times10^{-2}$ cfu/mL, about $1\times10^{-1}$ cfu/mL, about $1\times10^{0}$ cfu/mL, about $1\times10^1$ cfu/mL, about $1\times10^2$ cfu/mL, about $1\times10^3$ cfu/mL, about $1\times10^4$ cfu/mL, about $1\times10^5$ cfu/mL, about $1\times10^6$ cfu/mL, about $1\times10^7$ cfu/mL, about $1\times10^8$ cfu/mL, about $1\times10^9$ cfu/mL, or about $1\times10^{10}$ cfu/mL. In other aspects of this embodiment, a method disclosed herein may qualitatively or quantitatively detect pathogen having a concentration after an pre-enrichment step of, e.g., at least $1\times10^{-5}$ cfu/mL, at least $1\times10^{-4}$ cfu/mL, at least $1\times10^{-3}$ cfu/mL, at least $1\times10^{-2}$ cfu/mL, at least $1\times10^{-1}$ cfu/mL, at least $1\times10^{0}$ cfu/mL, at least $1\times10^1$ cfu/mL, at least $1\times10^2$ cfu/mL, at least $1\times10^3$ cfu/mL, at least $1\times10^4$ cfu/mL, at least $1\times10^5$ cfu/mL, at least $1\times10^6$ cfu/mL, at least $1\times10^7$ cfu/mL, at least $1\times10^8$ cfu/mL, at least $1\times10^9$ cfu/mL, or at least $1\times10^{10}$ cfu/mL. In yet other aspects of this embodiment, a method disclosed herein may qualitatively or quantitatively detect pathogen having a concentration after an pre-enrichment step of, e.g., at most $1\times10^{-5}$ cfu/mL, at most $1\times10^{-4}$ cfu/mL, at most $1\times10^{-3}$ cfu/mL, at most $1\times10^{-2}$ cfu/mL, at most $1\times10^{-1}$ cfu/mL, at most $1\times10^{0}$ cfu/mL, at most $1\times10^1$ cfu/mL, at most $1\times10^2$ cfu/mL, at most $1\times10^3$ cfu/mL, at most $1\times10^4$ cfu/mL, at most $1\times10^5$ cfu/mL, at most $1\times10^6$ cfu/mL, at most $1\times10^7$ cfu/mL, at most $1\times10^8$ cfu/mL, at most $1\times10^9$ cfu/mL, or at most $1\times10^{10}$ cfu/mL.

In still other aspects of this embodiment, a method disclosed herein may qualitatively or quantitatively detect pathogen having a concentration after an pre-enrichment step of, e.g., about $1\times10^{-5}$ cfu/mL to about about $1\times10^{-4}$ cfu/mL, about $1\times10^{-5}$ cfu/mL to about $1\times10^{-3}$ cfu/mL, about $1\times10^{-5}$ cfu/mL to about about $1\times10^{-2}$ cfu/mL, about $1\times10^{-5}$ cfu/mL to about $1\times10^{-1}$ cfu/mL, about $1\times10^{-5}$ cfu/mL to about about $1\times10^{0}$ cfu/mL, about $1\times10^{-5}$ cfu/mL to about $1\times10^1$ cfu/mL, about $1\times10^{-5}$ cfu/mL to about $1\times10^2$ cfu/mL, about $1\times10^{-5}$ cfu/mL to about $1\times10^3$ cfu/mL, about $1\times10^{-5}$ cfu/mL to about $1\times10^4$ cfu/mL, about $1\times10^{-5}$ cfu/mL to about $1\times10^5$ cfu/mL, about $1\times10^{-5}$ cfu/mL to about $1\times10^6$ cfu/mL, about $1\times10^{-5}$ cfu/mL to about $1\times10^7$ cfu/mL, about $1\times10^{-5}$ cfu/mL to about $1\times10^8$ cfu/mL, about $1\times10^{-5}$ cfu/mL to about $1\times10^9$ cfu/mL, about $1\times10^{-5}$ cfu/mL to about $1\times10^{10}$ cfu/mL, about $1\times10^{-4}$ cfu/mL to about $1\times10^{-3}$ cfu/mL, about $1\times10^{-4}$ cfu/mL to about $1\times10^{-2}$ cfu/mL, about $1\times10^{-4}$ cfu/mL to about $1\times10^{-1}$ cfu/mL, about $1\times10^{-4}$ cfu/mL to about $1\times10^{0}$ cfu/mL, about $1\times10^{-4}$ cfu/mL to about $1\times10^1$ cfu/mL, about $1\times10^{-4}$ cfu/mL to about $1\times10^2$ cfu/mL, about $1\times10^{-4}$ cfu/mL to about $1\times10^3$ cfu/mL, about $1\times10^{-4}$ cfu/mL to about $1\times10^4$ cfu/mL, about $1\times10^{-4}$ cfu/mL to about $1\times10^5$ cfu/mL, about $1\times10^{-4}$ cfu/mL to about $1\times10^6$ cfu/mL, about $1\times10^{-4}$ cfu/mL to about $1\times10^7$ cfu/mL, about $1\times10^{-4}$ cfu/mL to about $1\times10^8$ cfu/mL, about $1\times10^{-4}$ cfu/mL to about $1\times10^9$ cfu/mL, about $1\times10^{-4}$ cfu/mL to about $1\times10^{10}$ cfu/mL, about $1\times10^{-3}$ cfu/mL to about $1\times10^{-2}$ cfu/mL, about $1\times10^{-3}$ cfu/mL to about $1\times10^{-1}$ cfu/mL, about $1\times10^{-3}$ cfu/mL to about $1\times10^{0}$ cfu/mL, about $1\times10^{-3}$ cfu/mL to about $1\times10^1$ cfu/mL, about $1\times10^{-3}$ cfu/mL to about $1\times10^2$ cfu/mL, about $1\times10^{-3}$ cfu/mL to about $1\times10^3$ cfu/mL, about $1\times10^{-3}$ cfu/mL to about $1\times10^4$ cfu/mL, about $1\times10^{-3}$ cfu/mL to about $1\times10^5$ cfu/mL, about $1\times10^{-3}$ cfu/mL to about $1\times10^6$ cfu/mL, about $1\times10^{-3}$ cfu/mL to about $1\times10^7$ cfu/mL, about $1\times10^{-3}$ cfu/mL to about $1\times10^8$ cfu/mL, about $1\times10^{-3}$ cfu/mL to about $1\times10^9$ cfu/mL, about $1\times10^{-3}$ cfu/mL to about $1\times10^{10}$ cfu/mL, about $1\times10^{-2}$ cfu/mL to about $1\times10^{-1}$ cfu/mL, about $1\times10^{-2}$ cfu/mL to about $1\times10^{0}$ cfu/mL, about $1\times10^{-2}$ cfu/mL to about $1\times10^1$ cfu/mL, about $1\times10^{-2}$ cfu/mL to about $1\times10^2$ cfu/mL, about $1\times10^{-2}$ cfu/mL to about $1\times10^3$ cfu/mL, about $1\times10^{-2}$ cfu/mL to about $1\times10^4$ cfu/mL, about $1\times10^{-2}$ cfu/mL to about $1\times10^5$ cfu/mL, about $1\times10^{-2}$ cfu/mL to about $1\times10^6$ cfu/mL, about $1\times10^{-2}$ cfu/mL to about $1\times10^7$ cfu/mL, about $1\times10^{-2}$ cfu/mL to about $1\times10^8$ cfu/mL, about $1\times10^{-2}$ cfu/mL to about $1\times10^9$ cfu/mL, about $1\times10^{-2}$ cfu/mL to about $1\times10^{10}$ cfu/mL, about $1\times10^{-1}$ cfu/mL to about $1\times10^0$ cfu/mL, about $1\times10^{-1}$ cfu/mL to about $1\times10^1$ cfu/mL, about $1\times10^{-1}$ cfu/mL to about $1\times10^2$ cfu/mL, about $1\times10^{-1}$ cfu/mL to about $1\times10^3$ cfu/mL, about $1\times10^{-1}$ cfu/mL to about $1\times10^4$ cfu/mL, about $1\times10^{-1}$ cfu/mL to about $1\times10^5$ cfu/mL, about $1\times10^{-1}$ cfu/mL to about $1\times10^6$ cfu/mL, about $1\times10^{-1}$ cfu/mL to about $1\times10^7$ cfu/mL, about $1\times10^{-1}$ cfu/mL to about $1\times10^8$ cfu/mL, about $1\times10^{-1}$ cfu/mL to about $1\times10^9$ cfu/mL, about $1\times10^{-1}$ cfu/mL to about $1\times10^{10}$ cfu/mL, about $1\times10^0$ cfu/mL to about $1\times10^1$ cfu/mL, about $1\times10^0$ cfu/mL to about $1\times10^2$ cfu/mL, about $1\times10^0$ cfu/mL to about $1\times10^3$ cfu/mL, about $1\times10^0$ cfu/mL to about $1\times10^4$ cfu/mL, about $1\times10^0$ cfu/mL to about $1\times10^5$ cfu/mL, about $1\times10^0$ cfu/mL to about $1\times10^6$ cfu/mL, about $1\times10^0$ cfu/mL to about $1\times10^7$ cfu/mL, about $1\times10^0$ cfu/mL to about $1\times10^8$ cfu/mL, about $1\times10^0$ cfu/mL to about $1\times10^9$ cfu/mL, about $1\times10^0$ cfu/mL to about $1\times10^{10}$ cfu/mL, about $1\times10^1$ cfu/mL to about $1\times10^2$ cfu/mL, about $1\times10^1$ cfu/mL to about $1\times10^3$ cfu/mL, about $1\times10^1$ cfu/mL to about $1\times10^4$ cfu/mL, about $1\times10^1$ cfu/mL to about $1\times10^5$ cfu/mL, about $1\times10^1$ cfu/mL to about $1\times10^6$ cfu/mL, about $1\times10^1$ cfu/mL to about $1\times10^7$ cfu/mL, about $1\times10^1$ cfu/mL to about $1\times10^8$ cfu/mL, about $1\times10^1$ cfu/mL to about $1\times10^9$ cfu/mL, about $1\times10^1$ cfu/mL to about $1\times10^{10}$ cfu/mL, about $1\times10^2$ cfu/mL to about $1\times10^3$ cfu/mL, about $1\times10^2$ cfu/mL to about $1\times10^4$ cfu/mL, about $1\times10^2$ cfu/mL to about $1\times10^5$ cfu/mL, about $1\times10^2$ cfu/mL to about $1\times10^6$ cfu/mL, about $1\times10^2$ cfu/mL to about $1\times10^7$ cfu/mL, about $1\times10^2$ cfu/mL to about $1\times10^8$ cfu/mL, about $1\times10^2$ cfu/mL to about $1\times10^9$ cfu/mL, about $1\times10^2$ cfu/mL to about $1\times10^{10}$ cfu/mL, about $1\times10^3$ cfu/mL to about $1\times10^4$ cfu/mL, about $1\times10^3$ cfu/mL to about $1\times10^5$ cfu/mL, about $1\times10^3$ cfu/mL to about $1\times10^6$ cfu/mL, about $1\times10^3$ cfu/mL to about $1\times10^7$ cfu/mL, about $1\times10^3$ cfu/mL to about $1\times10^8$ cfu/mL, about $1\times10^3$ cfu/mL to about $1\times10^9$ cfu/mL, about $1\times10^3$ cfu/mL to about $1\times10^{10}$ cfu/mL, about $1\times10^4$ cfu/mL to about $1\times10^5$ cfu/mL, about $1\times10^4$ cfu/mL to about about $1\times10^6$ cfu/mL, about $1\times10^4$ cfu/mL to about $1\times10^7$ cfu/mL, about $1\times10^4$ cfu/mL to about $1\times10^8$ cfu/mL, about $1\times10^4$ cfu/mL to about $1\times10^9$ cfu/mL, or about $1\times10^4$ cfu/mL to about $1\times10^{10}$ cfu/mL.

In aspects of this embodiment, a method disclosed herein may qualitatively or quantitatively detect pathogen having a concentration after an enrichment step of, e.g., about $1\times10^{-5}$ cfu/mL, about $1\times10^{-4}$ cfu/mL, about $1\times10^{-3}$ cfu/mL, about $1\times10^{-2}$ cfu/mL, about $1\times10^{-1}$ cfu/mL, about $1\times10^0$ cfu/mL, about $1\times10^1$ cfu/mL, about $1\times10^2$ cfu/mL, about $1\times10^3$ cfu/mL, about $1\times10^4$ cfu/mL, about $1\times10^5$ cfu/mL, about $1\times10^6$ cfu/mL, about $1\times10^7$ cfu/mL, about $1\times10^8$ cfu/mL, about $1\times10^9$ cfu/mL, or about $1\times10^{10}$ cfu/mL. In other aspects of this embodiment, a method disclosed herein may qualitatively or quantitatively detect pathogen having a concentration after an enrichment step of, e.g., at least $1\times10^{-5}$ cfu/mL, at least $1\times10^{-4}$ cfu/mL, at least $1\times10^{-3}$ cfu/mL, at least $1\times10^{-2}$ cfu/mL, at least $1\times10^{-1}$ cfu/mL, at least $1\times10^0$ cfu/mL, at least $1\times10^1$ cfu/mL, at least $1\times10^2$ cfu/mL, at least $1\times10^3$ cfu/mL, at least $1\times10^4$ cfu/mL, at least $1\times10^5$ cfu/mL, at least $1\times10^6$ cfu/mL, at least $1\times10^7$ cfu/mL, at least $1\times10^8$ cfu/mL, at least $1\times10^9$ cfu/mL, or at least $1\times10^{10}$ cfu/mL. In yet other aspects of this embodiment, a method disclosed herein may qualitatively or quantitatively detect pathogen having a concentration after an enrichment step of, e.g., at most $1\times10^{-5}$ cfu/mL, at most $1\times10^{-4}$ cfu/mL, at most $1\times10^{-3}$ cfu/mL, at most $1\times10^{-2}$ cfu/mL, at most $1\times10^{-1}$ cfu/mL, at most $1\times10^0$ cfu/mL, at most $1\times10^1$ cfu/mL, at most $1\times10^2$ cfu/mL, at most $1\times10^3$ cfu/mL, at most $1\times10^4$ cfu/mL, at most $1\times10^5$ cfu/mL, at most $1\times10^6$ cfu/mL, at most $1\times10^7$ cfu/mL, at most $1\times10^8$ cfu/mL, at most $1\times10^9$ cfu/mL, or at most $1\times10^{10}$ cfu/mL.

In still other aspects of this embodiment, a method disclosed herein may qualitatively or quantitatively detect pathogen having a concentration after an enrichment step of, e.g., about $1\times10^{-5}$ cfu/mL to about $1\times10^{-4}$ cfu/mL, about $1\times10^{-5}$ cfu/mL to about $1\times10^{-3}$ cfu/mL, about $1\times10^{-5}$ cfu/mL to about $1\times10^{-2}$ cfu/mL, about $1\times10^{-5}$ cfu/mL to about $1\times10^{-1}$ cfu/mL, about $1\times10^{-5}$ cfu/mL to about $1\times10^0$ cfu/mL, about $1\times10^{-5}$ cfu/mL to about $1\times10^1$ cfu/mL, about $1\times10^{-5}$ cfu/mL to about $1\times10^2$ cfu/mL, about $1\times10^{-5}$ cfu/mL to about $1\times10^3$ cfu/mL, about $1\times10^{-5}$ cfu/mL to about $1\times10^4$ cfu/mL, about $1\times10^{-5}$ cfu/mL to about $1\times10^5$ cfu/mL, about $1\times10^{-5}$ cfu/mL to about $1\times10^6$ cfu/mL, about $1\times10^{-5}$ cfu/mL to about $1\times10^7$ cfu/mL, about $1\times10^{-5}$ cfu/mL to about $1\times10^8$ cfu/mL, about $1\times10^{-5}$ cfu/mL to about $1\times10^9$ cfu/mL, about $1\times10^{-5}$ cfu/mL to about $1\times10^{10}$ cfu/mL, about $1\times10^{-4}$ cfu/mL to about $1\times10^{-3}$ cfu/mL, about $1\times10^{-4}$ cfu/mL to about $1\times10^{-2}$ cfu/mL, about $1\times10^{-4}$ cfu/mL to about $1\times10^{-1}$ cfu/mL, about $1\times10^{-4}$ cfu/mL to about $1\times10^0$ cfu/mL, about $1\times10^{-4}$ cfu/mL to about $1\times10^1$ cfu/mL, about $1\times10^{-4}$ cfu/mL to about $1\times10^2$ cfu/mL, about $1\times10^{-4}$ cfu/mL to about $1\times10^3$ cfu/mL, about $1\times10^{-4}$ cfu/mL to about $1\times10^4$ cfu/mL, about $1\times10^{-4}$ cfu/mL to about $1\times10^5$ cfu/mL, about $1\times10^{-4}$ cfu/mL to about $1\times10^6$ cfu/mL, about $1\times10^{-4}$ cfu/mL to about $1\times10^7$ cfu/mL, about $1\times10^{-4}$ cfu/mL to about $1\times10^8$ cfu/mL, about $1\times10^{-4}$ cfu/mL to about $1\times10^9$ cfu/mL, about $1\times10^{-4}$ cfu/mL to about $1\times10^{10}$ cfu/mL, about $1\times10^{-3}$ cfu/mL to about $1\times10^{-2}$ cfu/mL, about $1\times10^{-3}$ cfu/mL to about $1\times10^{-1}$ cfu/mL, about $1\times10^{-3}$ cfu/mL to about $1\times10^0$ cfu/mL, about $1\times10^{-3}$ cfu/mL to about $1\times10^1$ cfu/mL, about $1\times10^{-3}$ cfu/mL to about $1\times10^2$ cfu/mL, about $1\times10^{-3}$ cfu/mL to about $1\times10^3$ cfu/mL, about $1\times10^{-3}$ cfu/mL to about $1\times10^4$ cfu/mL, about $1\times10^{-3}$ cfu/mL to about $1\times10^5$ cfu/mL, about $1\times10^{-3}$ cfu/mL to about $1\times10^6$ cfu/mL, about $1\times10^{-3}$ cfu/mL to about $1\times10^7$ cfu/mL, about $1\times10^{-3}$ cfu/mL to about $1\times10^8$ cfu/mL, about $1\times10^{-3}$ cfu/mL to about $1\times10^9$ cfu/mL, about $1\times10^{-3}$ cfu/mL to about $1\times10^{10}$ cfu/mL, about $1\times10^{-2}$ cfu/mL to about $1\times10^{-1}$ cfu/mL, about $1\times10^{-2}$ cfu/mL to about $1\times10^0$ cfu/mL, about $1\times10^{-2}$ cfu/mL to about $1\times10^1$ cfu/mL, about $1\times10^{-2}$ cfu/mL to about $1\times10^2$ cfu/mL, about $1\times10^{-2}$ cfu/mL to about $1\times10^3$ cfu/mL, about $1\times10^{-2}$ cfu/mL to about $1\times10^4$ cfu/mL, about $1\times10^{-2}$ cfu/mL to about $1\times10^5$ cfu/mL, about $1\times10^{-2}$ cfu/mL to about $1\times10^6$ cfu/mL, about $1\times10^{-2}$ cfu/mL to about $1\times10^7$ cfu/mL, about $1\times10^{-2}$ cfu/mL to about $1\times10^8$ cfu/mL, about $1\times10^{-2}$ cfu/mL to about $1\times10^9$ cfu/mL, about $1\times10^{-2}$ cfu/mL to about $1\times10^{10}$ cfu/mL, about $1\times10^{-1}$ cfu/mL to about $1\times10^0$ cfu/mL, about $1\times10^{-1}$ cfu/mL to about $1\times10^1$ cfu/mL, about $1\times10^{-1}$ cfu/mL to about $1\times10^2$ cfu/mL, about $1\times10^{-1}$ cfu/mL to about $1\times10^3$ cfu/mL, about $1\times10^{-1}$ cfu/mL to about $1\times10^4$ cfu/mL, about $1\times10^{-1}$ cfu/mL to about $1\times10^5$ cfu/mL, about $1\times10^{-1}$ cfu/mL to about $1\times10^6$ cfu/mL, about $1\times10^{-1}$ cfu/mL to about $1\times10^7$ cfu/mL, about $1\times10^{-1}$ cfu/mL to about $1\times10^8$ cfu/mL, about $1\times10^{-1}$ cfu/mL to about $1\times10^9$ cfu/mL, about $1\times10^{-1}$ cfu/mL to about $1\times10^{10}$ cfu/mL, about $1\times10^0$ cfu/mL to about $1\times10^1$ cfu/mL, about $1\times10^0$ cfu/mL to about $1\times10^2$ cfu/mL, about $1\times10^0$ cfu/mL to about $1\times10^3$ cfu/mL, about $1\times10^0$ cfu/mL to about $1\times10^4$ cfu/mL, about $1\times10^0$ cfu/mL to about $1\times10^5$ cfu/mL, about $1\times10^0$ cfu/mL to about $1\times10^6$ cfu/mL, about $1\times10^0$ cfu/mL to about $1\times10^7$ cfu/mL, about $1\times10^0$ cfu/mL to about $1\times10^8$ cfu/mL, about $1\times10^0$ cfu/mL to about $1\times10^9$ cfu/mL, about $1\times10^0$ cfu/mL to about $1\times10^{10}$ cfu/mL, about $1\times10^1$ cfu/mL to about $1\times10^2$ cfu/mL, about $1\times10^1$ cfu/mL to about $1\times10^3$ cfu/mL, about $1\times10^1$ cfu/mL to about $1\times10^4$ cfu/mL, about $1 \times 10^1$ cfu/mL to about $1 \times 10^5$ cfu/mL, about $1 \times 10^1$ cfu/mL to about about $1 \times 10^6$ cfu/mL, about $1 \times 10^1$ cfu/mL to about $1 \times 10^7$ cfu/mL, about $1 \times 10^1$ cfu/mL to about $1 \times 10^8$ cfu/mL, about $1 \times 10^1$ cfu/mL to about $1 \times 10^9$ cfu/mL, about $1 \times 10^1$ cfu/mL to about $1 \times 10^{10}$ cfu/mL, about $1 \times 10^2$ cfu/mL to about $1 \times 10^3$ cfu/mL, about $1 \times 10^2$ cfu/mL to about $1 \times 10^4$ cfu/mL, about $1 \times 10^2$ cfu/mL to about $1 \times 10^5$ cfu/mL, about $1 \times 10^2$ cfu/mL to about $1 \times 10^6$ cfu/mL, about $1 \times 10^2$ cfu/mL to about $1 \times 10^7$ cfu/mL, about $1 \times 10^2$ cfu/mL to about $1 \times 10^8$ cfu/mL, about $1 \times 10^2$ cfu/mL to about $1 \times 10^9$ cfu/mL, about $1 \times 10^2$ cfu/mL to about $1 \times 10^{10}$ cfu/mL, about $1 \times 10^3$ cfu/mL to about $1 \times 10^4$ cfu/mL, about $1 \times 10^3$ cfu/mL to about $1 \times 10^5$ cfu/mL, about $1 \times 10^3$ cfu/mL to about $1 \times 10^6$ cfu/mL, about $1 \times 10^3$ cfu/mL to about $1 \times 10^7$ cfu/mL, about $1 \times 10^3$ cfu/mL to about $1 \times 10^8$ cfu/mL, about $1 \times 10^3$ cfu/mL to about $1 \times 10^9$ cfu/mL, about $1 \times 10^3$ cfu/mL to about $1 \times 10^{10}$ cfu/mL, about $1 \times 10^4$ cfu/mL to about $1 \times 10^5$ cfu/mL, about $1 \times 10^4$ cfu/mL to about about $1 \times 10^6$ cfu/mL, about $1 \times 10^4$ cfu/mL to about $1 \times 10^7$ cfu/mL, about $1 \times 10^4$ cfu/mL to about $1 \times 10^8$ cfu/mL, about $1 \times 10^4$ cfu/mL to about $1 \times 10^9$ cfu/mL, or about $1 \times 10^4$ cfu/mL to about $1 \times 10^{10}$ cfu/mL.

Common detection procedures used to determine the presence or absence of a pathogen include nucleic acid-based detection methods, protein-based detection methods, activity-based detection methods, growth-based detection methods, and sensor-based detection methods.

In one embodiment, detection presence or absence of a pathogen of interest occurs using a nucleic acid-based detection method. Non-limiting examples of nucleic acid-based detection method include DNA-based detection methods and RNA-based detection methods. DNA-based detection methods include, without limitation, like Southern blot analysis, PCR-based assays, sequence analysis, immuno-based detection assays, and hybridization assays using FRET, polarization or other fluorescent, chemiluminescent or bioluminescent detection methods. RNA-based detection methods include, without limitation, like Northern blot analysis, RT-PCR-based assays, RNA sequencing, immuno-based detection assays, and hybridization assays using FRET, polarization or other fluorescent, chemiluminescent or bioluminescent detection methods.

In one embodiment, detection presence or absence of a pathogen of interest occurs using a protein-based detection method. Non-limiting examples of protein-based detection methods include gel-based detection methods, immuno-based detection methods and protein-interaction-based methods. Gel-based detection methods include, without limitation polyacrylamide gel electrophoresis and SDS-PAGE. Immuno-based detection methods include, without limitation, Western blot analysis, ELISA, and immunoprecipitation. Protein-interaction-based methods include, without limitation, protein-protein interaction-based assays, protein-DNA interaction-based assays, and protein-RNA interaction-based assays.

In one embodiment, detection presence or absence of a pathogen of interest occurs using an activity-based detection method. Non-limiting examples of activity-based detection methods include enzymatic activity assays and assays based on protein function. An enzymatic activity assays typically involves incubating an aliquot of media containing or potentially containing a pathogen of interest in a buffered solution containing a suitable substrate. If the desired enzyme is present in the aliquot, then is will catalyze the conversion of the substrate into a product. Measuring either the loss of substrate or the formation of product can then be either qualitatively or quantitatively correlated to the amount of enzyme present and hence the amount of pathogen. Similarly, assays based on protein function measure the amount of function present in the sample and extrapolate the amount of pathogen based on this measurement.

In one embodiment, detection presence or absence of a pathogen of interest occurs using a growth-based detection method. Non-limiting examples of growth-based detection method include plating assays measuring colony formation with or without growth selective agents and spectrophotometer assays measuring cell density. A plating assay typically involves plating an aliquot of media onto an agar plate comprising nutrients to sustain growth of the pathogen of interest. The inoculated agar plates are then incubated for a specified temperature and time and growth of pathogen colonies assessed. In some embodiments, the agar plates are incubated at about 25° C. to about 42° C. for about 12 hours to about 48 hours. In aspects of this embodiments, the agar plates are incubated at about 37° C. for about 14 hours to about 16 hours. This assessment may be qualitative by simply assessing the presence or absence of pathogen colonies, or quantitative, where the number of pathogen colonies are counted. Besides nutrients, an agar plate may contain a chromogenic compound that stains or otherwise provides a visual signal that identifies the colony as a pathogen colony. In addition, an agar plate may contain a compound that selects for pathogen colony growth by either supplying a compound that facilitates or is required for pathogen growth or inhibits the growth of contaminating microorganisms. A spectrophotometer assays measuring cell density typically involves measuring the cell density of an aliquot taken from media using a spectrophotometer at a specific wavelength.

In one embodiment, detection presence or absence of a pathogen of interest occurs using a sensor-based detection method. Sensors can be classified according to the type of energy being transfer, such as, e.g., thermal, electromagnetic, mechanical, and electrochemical.

In an aspect of this embodiment, a sensor-based detection method is a biosensor-based detection method. A biosensor is a type of analytical device incorporating a biological material, a biologically derived material or a biomimic intimately associated with or integrated within a physicochemical transducer or transducing microsystem. A biosensor converts the modification of the physical or chemical properties of a biomatrix (e.g., enzyme, antibodies, receptors, organelles, microorganisms) into an electric or other kinds of signal whose amplitude depends on the concentration of defined analytes in the solution.

Non-limiting examples of a biosensor include an enzymatic biosensor, a DNA sensor, and an immunosensor. Enzyme-based biosensor require the immobilization of an enzyme onto an electrode surface for the quantification of an analyte. DNA-based biosensor require the immobilization of non-complimentary DNA strand of a target sequence onto an electrode surface for the quantification of an analyte. Immuno-based biosensor require the immobilization of an antibody onto an electrode surface for the quantification of an analyte.

A biosensor comprises a biorecognition element, a signal transducer, and a detector. The biorecognition element includes antibodies, peptides, nucleic acids, or enzymes and is the portion of the sensor that initially binds to or interacts with the analyte (e.g., a pathogen). In many cases this is associated with a conformational change, substrate cleavage, or enzymatic reaction that transduces the biorecognition event into a signal that may be detected via several modalities. A biosensor comprises two electrodes (reference and a working electrodes) or three electrodes (reference, working, and counter electrode).

A reference electrode includes liquid and solid-state reference electrodes and is an electrode having a known stable potential to which all other electrode potentials are referenced. A reference electrode can be manufactured by film deposition, electroplating and screen printing. Non-limiting examples of a reference electrode include silver-silver chloride electrode, calomel electrode, hydrogen electrode, mercury-mercury oxide electrode, mercury-mercurous sulfate electrode, copper-copper sulfate electrode, and palladium hydride electrode.

A biosensor typically uses the power of electrochemical techniques for biological processes by quantitatively producing an electrical signal that relates to the concentration of a biological analyte. Such electrochemical biosensors can be classified as potentiometric, amperometric, voltametric and impedimetric/conductimetric based upon the analytical principles of operation. Potentiometric electrochemical sensors measure an equilibrium potential difference between a working electrode and a reference electrode at zero current flow. Voltammetric electrochemical sensors measure the current as a function of varying potential is applied between a working electrode and a reference electrode. Amperometric electrochemical sensors measure the current as a function of constant potential is applied between a working electrode and a reference electrode. Impedimetric/conductimetric electrochemical sensors measure the changes of electrical properties between a working electrode and a reference electrode. Electrochemical detection using a biosensor may be a direct measurement of the change in electrical properties or an indirect measurement using an auxiliary reaction which involves a marking (redox active) compound for signal generation.

Aspect of the present specification disclose, in part, a detection solution. When a biosensor is a glucose-based biosensor, a detection solution disclosed herein typically includes a buffered solution comprises magnesium chloride, p-aminofenil phosphate, and glucose. Optionally, such a detection solution may comprise a surfactant as disclosed herein.

Any buffer may be used, with the proviso that the resulting buffered solution is useful to practice the methods disclosed herein. A buffered solution can be varied as appropriate by one skilled in the art and generally depends, in part, on the pH value desired for the mobile phase, the protein being eluted, and the conductivity values being employed. Therefore, aspects of this embodiment may optionally include, e.g., 2-(N-morpholino) ethanesulfonic acid (MES), N-(2-acetamido)iminodiacetic acid (ADA), dimethylarsinic acid (Cacodylate), piperazine-N,N'-bis(2-ethanesulfonic acid) (PIPES), N-(2-Acetamido)-2-aminoethanesulfonic acid (ACES), cholamine chloride, N,N'-bis (2-hydroxyethyl)-2-aminoethanesulfonic acid (BES), 3-(N-morpholino) propanesulfonic acid (MOPS), 2-{[tris (hydroxymethyl)methyl]amino}ethanesulfonic acid (TES), N-(2-hydroxyethyl) piperazine-N'-(2-ethanesulfonic acid) (HEPES), piperazine-N,N'-bis(2-hydroxypropanesulfonic acid) (POPSO), N-tris(hydroxymethyl)methylglycine (Tricine), tris(hydroxymethyl)methylamine (Tris), acetamidoglycine, N,N-bis(2-hydroxyethyl)glycine (Bicine), N-tris (hydroxymethyl)methyl-3-aminopropanesulfonic acid (TAPS), 3-[(1,1-dimethyl-2-hydroxyethyl)amino]-2-hydroxypropanesulfonic acid (AMPSO), 3-(cyclohexylamino)-2-hydroxy-1-propanesulfonic acid (CAPSO), and 3-(cyclohexylamino)-1-propanesulfonic acid (CAPS); acetate buffers, such as, e.g., magnesium acetate, potassium acetate, and Tris acetate; borate buffers; citrate buffers; phosphate buffers, such as, e.g., potassium phosphate buffers and sodium phosphate buffers; saline buffers, such as, e.g., phosphate-buffered saline (PBS), HEPES-buffered saline (HBS), and Tris-buffered saline (TBS), saline sodium citrate (SSC); universal buffers, such as, e.g., buffers comprising citric acid and potassium phosphate, Britton-Robinson buffer, Carmody buffer and the like, or any combination thereof. Non-limiting examples of how to make and use specific buffers are described in, e.g., MOLECULAR CLONING, A LABORATORY MANUAL (Joseph Sambrook & David W. Russell eds., Cold Spring Harbor Laboratory Press, 3rd ed. 2001) and CURRENT PROTOCOLS IN MOLECULAR BIOLOGY (Frederick M. Ausubel et al., eds. John Wiley & Sons, 2004).

Any concentration of magnesium chloride may be used in a detection solution, with the proviso that the concentration is useful to practice the methods disclosed herein. In aspects of this embodiment, a concentration of magnesium chloride used in a detection solution may be, e.g., about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM. In other aspects of this embodiment, a concentration of magnesium chloride used in a detection solution may be, e.g., at least 5 mM, at least 10 mM, at least 15 mM, at least 20 mM, at least 25 mM, at least 30 mM, at least 35 mM, at least 40 mM, at least 45 mM, at least 50 mM, at least 55 mM, at least 60 mM, at least 65 mM, at least 70 mM, at least 75 mM, at least 80 mM, at least 85 mM, at least 90 mM, at least 95 mM, or at least 100 mM. In yet other aspects of this embodiment, a concentration of magnesium chloride used in a detection solution may be, e.g., at most 5 mM, at most 10 mM, at most 15 mM, at most 20 mM, at most 25 mM, at most 30 mM, at most 35 mM, at most 40 mM, at most 45 mM, at most 50 mM, at most 55 mM, at most 60 mM, at most 65 mM, at most 70 mM, at most 75 mM, at most 80 mM, at most 85 mM, at most 90 mM, at most 95 mM, or at most 100 mM. In still other aspects of this embodiment, a concentration of magnesium chloride used in a detection solution may be, e.g., about 5 mM to about 10 mM, about 5 mM to about 20 mM, about 5 mM to about 30 mM, about 5 mM to about 40 mM, about 5 mM to about 50 mM, about 5 mM to about 60 mM, about 5 mM to about 70 mM, about 5 mM to about 80 mM, about 5 mM to about 90 mM, about 5 mM to about 100 mM, about 10 mM to about 20 mM, about 10 mM to about 30 mM, about 10 mM to about 40 mM, about 10 mM to about 50 mM, about 10 mM to about 60 mM, about 10 mM to about 70 mM, about 10 mM to about 80 mM, about 10 mM to about 90 mM, about 10 mM to about 100 mM, about 20 mM to about 30 mM, about 20 mM to about 40 mM, about 20 mM to about 50 mM, about 20 mM to about 60 mM, about 20 mM to about 70 mM, about 20 mM to about 80 mM, about 20 mM to about 90 mM, or about 20 mM to about 100 mM.

Any concentration of p-aminofenil phosphate may be used in a detection solution, with the proviso that the concentration is useful to practice the methods disclosed herein. In aspects of this embodiment, a concentration of p-aminofenil phosphate used in a detection solution may be, e.g., about 0.1 mM, about 0.2 mM, about 0.3 mM, about 0.4 mM, about 0.5 mM, about 0.6 mM, about 0.7 mM, about 0.8 mM, about 0.9 mM, about 1.0 mM, about 1.1 mM, about 1.2 mM, about 1.3 mM, about 1.4 mM, about 1.5 mM, about 1.6 mM, about 1.7 mM, about 1.8 mM, about 1.9 mM, about 2.0 mM, about 2.1 mM, about 2.2 mM, about 2.3 mM, about 2.4 mM, or about 2.5 mM. In other aspects of this embodiment, a concentration of p-aminofenil phosphate used in a detection solution may be, e.g., at least 0.1 mM, at least 0.2 mM, at least 0.3 mM, at least 0.4 mM, at least 0.5 mM, at least 0.6 mM, at least 0.7 mM, at least 0.8 mM, at least 0.9 mM, at least 1.0 mM, at least 1.1 mM, at least 1.2 mM, at least 1.3 mM, at least 1.4 mM, at least 1.5 mM, at least 1.6 mM, at least 1.7 mM, at least 1.8 mM, at least 1.9 mM, at least 2.0 mM, at least 2.1 mM, at least 2.2 mM, at least 2.3 mM, at least 2.4 mM, or at least 2.5 mM. In yet other aspects of this embodiment, a concentration of p-aminofenil phosphate used in a detection solution may be, e.g., at most 0.1 mM, at most 0.2 mM, at most 0.3 mM, at most 0.4 mM, at most 0.5 mM, at most 0.6 mM, at most 0.7 mM, at most 0.8 mM, at most 0.9 mM, at most 1.0 mM, at most 1.1 mM, at most 1.2 mM, at most 1.3 mM, at most 1.4 mM, at most 1.5 mM, at most 1.6 mM, at most 1.7 mM, at most 1.8 mM, at most 1.9 mM, at most 2.0 mM, at most 2.1 mM, at most 2.2 mM, at most 2.3 mM, at most 2.4 mM, or at most 2.5 mM. In still other aspects of this embodiment, a concentration of p-aminofenil phosphate used in a detection solution may be, e.g., about 0.1 mM to about 0.5 mM, about 0.1 mM to about 1.0 mM, about 0.1 mM to about 1.5 mM, about 0.1 mM to about 2.0 mM, about 0.1 mM to about 2.5 mM, about 0.3 mM to about 0.5 mM, about 0.3 mM to about 1.0 mM, about 0.3 mM to about 1.5 mM, about 0.3 mM to about 2.0 mM, about 0.3 mM to about 2.5 mM, about 0.5 mM to about 1.0 mM, about 0.5 mM to about 1.5 mM, about 0.5 mM to about 2.0 mM, about 0.5 mM to about 2.5 mM, about 0.7 mM to about 1.0 mM, about 0.7 mM to about 1.5 mM, about 0.7 mM to about 2.0 mM, about 0.7 mM to about 2.5 mM, about 1.0 mM to about 1.5 mM, about 1.0 mM to about 2.0 mM, about 1.0 mM to about 2.5 mM, about 1.5 mM to about 2.0 mM, about 1.5 mM to about 2.5 mM, or about 2.0 mM to about 2.5 mM.

Any concentration of glucose may be used in a detection solution, with the proviso that the concentration is useful to practice the methods disclosed herein. In aspects of this embodiment, a concentration of glucose used in a detection solution may be, e.g., about 1 mM, about 2 mM, about 3 mM, about 4 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, or about 50 mM. In other aspects of this embodiment, a concentration of glucose used in a detection solution may be, e.g., at least 1 mM, at least 2 mM, at least 3 mM, at least 4 mM, at least 5 mM, at least 6 mM, at least 7 mM, at least 8 mM, at least 9 mM, at least 10 mM, at least 15 mM, at least 20 mM, at least 25 mM, at least 30 mM, at least 35 mM, at least 40 mM, at least 45 mM, or at least 50 mM. In yet other aspects of this embodiment, a concentration of glucose used in a detection solution may be, e.g., at most 1 mM, at most 2 mM, at most 3 mM, at most 4 mM, at most 5 mM, at most 6 mM, at most 7 mM, at most 8 mM, at most 9 mM, at most 10 mM, at most 15 mM, at most 20 mM, at most 25 mM, at most 30 mM, at most 35 mM, at most 40 mM, at most 45 mM, or at most 50 mM. In still other aspects of this embodiment, a concentration of glucose used in a detection solution may be, e.g., about 1 mM to about 10 mM, about 1 mM to about 15 mM, about 1 mM to about 20 mM, about 1 mM to about 30 mM, about 1 mM to about 40 mM, about 1 mM to about 50 mM, about 5 mM to about 10 mM, about 5 mM to about 15 mM, about 5 mM to about 20 mM, about 5 mM to about 30 mM, about 5 mM to about 40 mM, about 5 mM to about 50 mM, about 10 mM to about 15 mM, about 10 mM to about 20 mM, about 10 mM to about 30 mM, about 10 mM to about 40 mM, or about 10 mM to about 50 mM.

Any concentration of surfactant may be used in a detection solution, with the proviso that the concentration is useful to practice the methods disclosed herein. Surfactants disclosed herein at the concentrations disclosed herein may be used in preparing a detection solution. In aspects of this embodiment, a detection solution comprises between 0.1% (v/v) and 10% (v/v) detergent B-Per, or a surfactant of polyoxyethylene glycol sorbitan alkyl esters family (TWEEN® family) or polyoxyethylene glycol octylphenol ethers family (TRITON® family).

In an aspect of this embodiment, a detection solution may be 200 mM Phosphate buffer (pH 5.5) detection solution. In an aspect of this embodiment, 200 mM Phosphate buffer (pH 5.5) detection solution may comprise 0.0021 g/mL Sodium Hydrogen Phosphate, 0.0289 g/mL Sodium Dihydrogen Phosphate, 0.0020 g/mL Magnesium chloride, 0.0018 g/mL Glucose, and 0.0002 g/mL p-aminophenyl phosphate.

In an aspect of this embodiment, a detection solution may be 200 mM Phosphate buffer (pH 5.7) detection solution. In an aspect of this embodiment, 200 mM Phosphate buffer (pH 5.7) detection solution may comprise 0.0174 g/mL Potassium Hydrogen Phosphate, 0.0204 g/mL Potassium Phosphate (Phtalate), 0.0020 g/mL Magnesium chloride, 0.0018 g/mL Glucose, and 0.0002 g/mL p-aminophenyl phosphate.

In an aspect of this embodiment, a detection solution may be 200 mM Phosphate buffer (pH 7.0) detection solution. In an aspect of this embodiment, 200 mM Phosphate buffer (pH 7.0) detection solution may comprise 0.0156 g/mL Sodium Hydrogen Phosphate, 0.0142 g/mL Sodium Dihydrogen Phosphate, 0.0020 g/mL Magnesium chloride, 0.0018 g/mL Glucose, and 0.0002 g/mL p-aminophenyl phosphate.

In an aspect of this embodiment, a detection solution may be 160 mM Phosphate-citrate buffer (pH 5.5) detection solution. In an aspect of this embodiment, 160 mM Phosphate-citrate buffer (pH 5.5) detection solution may comprise 0.0161 g/mL Sodium Hydrogen Phosphate, 0.0090 g/mL Citric Acid, 0.0020 g/mL Magnesium chloride, 0.0018 g/mL Glucose, and 0.0002 g/mL p-aminophenyl phosphate.

In an aspect of this embodiment, a detection solution may be 200 mM Acetate buffer (pH 5.7) detection solution. In an aspect of this embodiment, 200 mM Acetate buffer (pH 5.7) detection solution may comprise 1.15 μL Acetic Acid, 0.0015 g/mL Sodium Acetate, 0.0020 g/mL Magnesium chloride, 0.0018 g/mL Glucose, and 0.0002 g/mL p-aminophenyl phosphate.

In an aspect of this embodiment, a detection solution may be 200 mM Tris buffer (pH 9.8) detection solution. In an aspect of this embodiment, 200 mM Tris buffer (pH 9.8) detection solution may comprise 0.0243 g/mL TRIS, 0.0020 g/mL Magnesium chloride, 0.0018 g/mL Glucose, and 0.0002 g/mL p-aminophenyl phosphate.

Aspect of the present specification disclose, in part, incubation of a detection solution. Incubation of a detection solution is performed under temperature and time parameters that facilitate detection of a signal. Incubation a detection solution may be performed under agitation/rotation.

Any temperature may be used during incubation of a detection solution, with the proviso that the temperature is useful to practice the methods disclosed herein. In aspects of this embodiment, a temperature used to incubate a detection solution may be, e.g., about 15° C., about 16° C., about 17° C., about 18° C., about 19° C., about 20° C., about 21° C., about 22° C., about 23° C., about 24° C., or about 25° C. In other aspects of this embodiment, a temperature used to incubate a detection solution may be, e.g., at least 15° C., at least 16° C., at least 17° C., at least 18° C., at least 19° C., at least 20° C., at least 21° C., at least 22° C., at least 23° C., at least 24° C., or at least 25° C. In yet other aspects of this embodiment, a temperature used to incubate a detection solution may be, e.g., at most 15° C., at most 16° C., at most 17° C., at most 18° C., at most 19° C., at most 20° C., at most 21° C., at most 22° C., at most 23° C., at most 24° C., or at most 25° C. In still other aspects of this embodiment, a temperature used to incubate a detection solution may be, e.g., about 15° C. to about 19° C., about 16° C. to about 20° C., about 17° C. to about 21° C., about 18° C. to about 22° C., about 19° C. to about 23° C., about 20° C. to about 24° C., about 21° C. to about 25° C., about 22° C. to about 26° C., about 23° C. to about 27° C., about 24° C. to about 28° C., or about 25° C. to about 29° C. In other aspects of this embodiment, a temperature used to incubate a detection solution may be, e.g., about 34° C. to about 39° C., about 34° C. to about 40° C., about 35° C. to about 45° C., about 36° C. to about 44° C., about 36° C. to about 43° C., about 37° C. to about 42° C., about 34° C. to about 45° C. or about 39° C. to about 45° C.

Any time may be used during incubation of a detection solution, with the proviso that the time is useful to practice the methods disclosed herein. In aspects of this embodiment, a time used to incubate a detection solution may be, e.g., about 5 minutes, about 10 minutes, about 15 minutes, about 20 minutes, about 30 minutes, about 40 minutes, about 50 minutes, about 60 minutes, about 70 minutes, about 80 minutes, about 90 minutes, about 100 minutes, about 110 minutes, about 120 minutes, about 130 minutes, about 140 minutes, or about 150 minutes. In other aspects of this embodiment, a time used to incubate a detection solution may be, e.g., at least 5 minutes, at least 10 minutes, at least 15 minutes, at least 20 minutes, at least 30 minutes, at least 40 minutes, at least 50 minutes, at least 60 minutes, at least 70 minutes, at least 80 minutes, at least 90 minutes, at least 100 minutes, at least 110 minutes, at least 120 minutes, at least 130 minutes, at least 140 minutes, or at least 150 minutes. In yet other aspects of this embodiment, a time used to a detection solution may be, e.g., at most 5 minutes, at most 10 minutes, at most 15 minutes, at most 20 minutes, at most 30 minutes, at most 40 minutes, at most 50 minutes, at most 60 minutes, at most 70 minutes, at most 80 minutes, at most 90 minutes, at most 100 minutes, at most 110 minutes, at most 120 minutes, at most 130 minutes, at most 140 minutes, or at most 150 minutes.

In yet other aspects of this embodiment, a time used to a detection solution may be, e.g., about 5 minutes to about 20 minutes, about 5 minutes to about 30 minutes, about 5 minutes to about 40 minutes, about 5 minutes to about 50 minutes, about 5 minutes to about 60 minutes, about 5 minutes to about 70 minutes, about 5 minutes to about 80 minutes, about 5 minutes to about 90 minutes, about 5 minutes to about 100 minutes, about 5 minutes to about 110 minutes, about 5 minutes to about 120 minutes, about 5 minutes to about 130 minutes, about 5 minutes to about 140 minutes, about 5 minutes to about 150 minutes, about 10 minutes to about 20 minutes, about 10 minutes to about 30 minutes, about 10 minutes to about 40 minutes, about 10 minutes to about 50 minutes, about 10 minutes to about 60 minutes, about 10 minutes to about 70 minutes, about 10 minutes to about 80 minutes, about 10 minutes to about 90 minutes, about 10 minutes to about 100 minutes, about 10 minutes to about 110 minutes, about 10 minutes to about 120 minutes, about 10 minutes to about 130 minutes, about 10 minutes to about 140 minutes, about 10 minutes to about 150 minutes, about 20 minutes to about 30 minutes, about 20 minutes to about 40 minutes, about 20 minutes to about 50 minutes, about 20 minutes to about 60 minutes, about 20 minutes to about 70 minutes, about 20 minutes to about 80 minutes, about 20 minutes to about 90 minutes, about 20 minutes to about 100 minutes, about 20 minutes to about 110 minutes, about 20 minutes to about 120 minutes, about 20 minutes to about 130 minutes, about 20 minutes to about 140 minutes, about 20 minutes to about 150 minutes, about 30 minutes to about 40 minutes, about 30 minutes to about 50 minutes, about 30 minutes to about 60 minutes, about 30 minutes to about 70 minutes, about 30 minutes to about 80 minutes, about 30 minutes to about 90 minutes, about 30 minutes to about 100 minutes, about 30 minutes to about 110 minutes, about 30 minutes to about 120 minutes, about 30 minutes to about 130 minutes, about 30 minutes to about 140 minutes, about 30 minutes to about 150 minutes, about 60 minutes to about 70 minutes, about 60 minutes to about 80 minutes, about 60 minutes to about 90 minutes, about 60 minutes to about 100 minutes, about 60 minutes to about 110 minutes, about 60 minutes to about 120 minutes, about 60 minutes to about 130 minutes, about 60 minutes to about 140 minutes, about 60 minutes to about 150 minutes, about 90 minutes to about 100 minutes, about 90 minutes to about 110 minutes, about 90 minutes to about 120 minutes, about 90 minutes to about 130 minutes, about 90 minutes to about 140 minutes, about 90 minutes to about 150 minutes, about 120 minutes to about 130 minutes, about 120 minutes to about 140 minutes, or about 120 minutes to about 150 minutes.

In aspects of this embodiment, a detection solution may be incubated at a temperature of, e.g., about 15° C., about 16° C., about 17° C., about 18° C., about 19° C., about 20° C., about 21° C., about 22° C., about 23° C., about 24° C., or about 25° C. for a time of, e.g., about 5 minutes, about 10 minutes, about 15 minutes, about 20 minutes, about 30 minutes, about 40 minutes, about 50 minutes, about 60 minutes, about 70 minutes, about 80 minutes, about 90 minutes, about 100 minutes, about 110 minutes, about 120 minutes, about 130 minutes, about 140 minutes, or about 150 minutes.

In other aspects of this embodiment, a detection solution may be incubated at a temperature of, e.g., at least 15° C., at least 16° C., at least 17° C., at least 18° C., at least 19° C., at least 20° C., at least 21° C., at least 22° C., at least 23° C., at least 24° C., or at least 25° C. for a time of, e.g., at least 5 minutes, at least 10 minutes, at least 15 minutes, at least 20 minutes, at least 30 minutes, at least 40 minutes, at least 50 minutes, at least 60 minutes, at least 70 minutes, at least 80 minutes, at least 90 minutes, at least 100 minutes, at least 110 minutes, at least 120 minutes, at least 130 minutes, at least 140 minutes, or at least 150 minutes.

In yet other aspects of this embodiment, a detection solution may be incubated at a temperature of, e.g., at most 15° C., at most 16° C., at most 17° C., at most 18° C., at most 19° C., at most 20° C., at most 21° C., at most 22° C., at most 23° C., at most 24° C., or at most 25° C., for a time of, e.g., at most 5 minutes, at most 10 minutes, at most 15 minutes, at most 20 minutes, at most 30 minutes, at most 40 minutes, at most 50 minutes, at most 60 minutes, at most 70 minutes, at most 80 minutes, at most 90 minutes, at most 100 minutes, at most 110 minutes, at most 120 minutes, at most 130 minutes, at most 140 minutes, or at most 150 minutes.

In still other aspects of this embodiment, a detection solution may be incubated at a temperature of, e.g., about 15° C. to about 19° C., about 16° C. to about 20° C., about 17° C. to about 21° C., about 18° C. to about 22° C., about 19° C. to about 23° C., about 20° C. to about 24° C., about 21° C. to about 25° C., about 22° C. to about 26° C., about 23° C. to about 27° C., about 24° C. to about 28° C., or about 25° C. to about 29° C. for a time of, e.g., about 5 minutes to about 20 minutes, about 5 minutes to about 30 minutes, about 5 minutes to about 40 minutes, about 5 minutes to about 50 minutes, about 5 minutes to about 60 minutes, about 5 minutes to about 70 minutes, about 5 minutes to about 80 minutes, about 5 minutes to about 90 minutes, about 5 minutes to about 100 minutes, about 5 minutes to about 110 minutes, about 5 minutes to about 120 minutes, about 5 minutes to about 130 minutes, about 5 minutes to about 140 minutes, about 5 minutes to about 150 minutes, about 10 minutes to about 20 minutes, about 10 minutes to about 30 minutes, about 10 minutes to about 40 minutes, about 10 minutes to about 50 minutes, about 10 minutes to about 60 minutes, about 10 minutes to about 70 minutes, about 10 minutes to about 80 minutes, about 10 minutes to about 90 minutes, about 10 minutes to about 100 minutes, about 10 minutes to about 110 minutes, about 10 minutes to about 120 minutes, about 10 minutes to about 130 minutes, about 10 minutes to about 140 minutes, about 10 minutes to about 150 minutes, about 20 minutes to about 30 minutes, about 20 minutes to about 40 minutes, about 20 minutes to about 50 minutes, about 20 minutes to about 60 minutes, about 20 minutes to about 70 minutes, about 20 minutes to about 80 minutes, about 20 minutes to about 90 minutes, about 20 minutes to about 100 minutes, about 20 minutes to about 110 minutes, about 20 minutes to about 120 minutes, about 20 minutes to about 130 minutes, about 20 minutes to about 140 minutes, about 20 minutes to about 150 minutes, about 30 minutes to about 40 minutes, about 30 minutes to about 50 minutes, about 30 minutes to about 60 minutes, about 30 minutes to about 70 minutes, about 30 minutes to about 80 minutes, about 30 minutes to about 90 minutes, about 30 minutes to about 100 minutes, about 30 minutes to about 110 minutes, about 30 minutes to about 120 minutes, about 30 minutes to about 130 minutes, about 30 minutes to about 140 minutes, about 30 minutes to about 150 minutes, about 60 minutes to about 70 minutes, about 60 minutes to about 80 minutes, about 60 minutes to about 90 minutes, about 60 minutes to about 100 minutes, about 60 minutes to about 110 minutes, about 60 minutes to about 120 minutes, about 60 minutes to about 130 minutes, about 60 minutes to about 140 minutes, about 60 minutes to about 150 minutes, about 90 minutes to about 100 minutes, about 90 minutes to about 110 minutes, about 90 minutes to about 120 minutes, about 90 minutes to about 130 minutes, about 90 minutes to about 140 minutes, about 90 minutes to about 150 minutes, about 120 minutes to about 130 minutes, about 120 minutes to about 140 minutes, or about 120 minutes to about 150 minutes.

After incubation of a detection solution, an aliquot is removed for analysis of a detectable electrochemical signal. In aspects of this embodiment, a volume of an aliquot to be analyzed for a detectable electrochemical signal may be, e.g., about 1 µL, about 2 µL, about 3 µL, about 4 µL, about 5 µL, about 6 µL, about 7 µL, about 8 µL, about 9 µL, about 10 µL, about 11 µL, about 12 µL, about 13 µL, about 14 µL, about 15 µL, about 16 µL, about 17 µL, about 18 µL, about 19 µL, or about 20 µL. In other aspects of this embodiment, a volume of an aliquot to be analyzed for a detectable electrochemical signal may be, e.g., at least 1 µL, at least 2 µL, at least 3 µL, at least 4 µL, at least 5 µL, at least 6 µL, at least 7 µL, at least 8 µL, at least 9 µL, at least 10 µL, at least 11 µL, at least 12 µL, at least 13 µL, at least 14 µL, at least 15 µL, at least 16 µL, at least 17 µL, at least 18 µL, at least 19 µL, or at least 20 µL. In yet other aspects of this embodiment, a volume of an aliquot to be analyzed for a detectable electrochemical signal may be, e.g., at most 1 µL, at most 2 µL, at most 3 µL, at most 4 µL, at most 5 µL, at most 6 µL, at most 7 µL, at most 8 µL, at most 9 µL, at most 10 µL, at most 11 µL, at most 12 µL, at most 13 µL, at most 14 µL, at most 15 µL, at most 16 µL, at most 17 µL, at most 18 µL, at most 19 µL, or at most 20 µL. In yet other aspects of this embodiment, a volume of an aliquot to be analyzed for a detectable electrochemical signal may be, e.g., about 1 µL to about 5 µL, about 1 µL to about 10 µL, about 1 µL to about 15 µL, about 1 µL to about 20 µL, 2 µL to about 5 µL, about 2 µL to about 10 µL, about 2 µL to about 15 µL, about 2 µL to about 20 µL, about 5 µL to about 10 µL, about 5 µL to about 15 µL, about 5 µL to about 20 µL, about 10 µL to about 15 µL, about 10 µL to about 20 µL, or about 15 µL to about 20 µL.

An electrochemical signal can be analyzed using an instrument which is capable of measuring and/or analyzing potentiometric, voltammetric, amperometric and/or impedance/conductance parameters. Typically, such instrumentation is operated using computer-controlled software. A non-limiting example is PalmSens3, a potentiostat, galvanostat, and impedance analyzer and PSTrace, its accompanying software (PalmSens BV, Utrecht, Netherlands).

In other embodiments, a method disclosed herein can be performed to completion in, e.g., about 18 hours, about 20 hours, about 22 hours, about 24 hours, about 26 hours, about 28 hours, about 30 hours, about 32 hours, about 34 hours, or about 36 hours. In yet other embodiments, a method comprising a pre-enrichment step disclosed herein and an enrichment step disclosed herein can be performed to completion in, e.g., about 18 hours, about 20 hours, about 22 hours, about 24 hours, about 26 hours, about 28 hours, about 30 hours, about 32 hours, about 34 hours, or about 36 hours. In still other embodiments, a method comprising a pre-enrichment step disclosed herein, an enrichment step disclosed herein and a detection step disclosed herein can be performed to completion in, e.g., about 18 hours, about 20 hours, about 22 hours, about 24 hours, about 26 hours, about 28 hours, about 30 hours, about 32 hours, about 34 hours, or about 36 hours. In other embodiments, a method comprising a pre-enrichment step disclosed herein, an enrichment step disclosed herein, a purification step disclosed herein, and a detection step disclosed herein can be performed to completion in, e.g., about 18 hours, about 20 hours, about 22 hours, about 24 hours, about 26 hours, about 28 hours, about 30 hours, about 32 hours, about 34 hours, or about 36 hours.

In other embodiments, a method disclosed herein can be performed to completion in, e.g., less than 18 hours, less than 20 hours, less than 22 hours, less than 24 hours, less than 26 hours, less than 28 hours, less than 30 hours, less than 32 hours, less than 34 hours, or less than 36 hours. In yet other embodiments, a method comprising a pre-enrichment step disclosed herein and an enrichment step disclosed herein can be performed to completion in, e.g., less than 18 hours, less than 20 hours, less than 22 hours, less than 24 hours, less than 26 hours, less than 28 hours, less than 30 hours, less than 32 hours, less than 34 hours, or less than 36 hours. In still other embodiments, a method comprising a pre-enrichment step disclosed herein, an enrichment step disclosed herein and a detection step disclosed herein can be performed to completion in, e.g., less than 18 hours, less than 20 hours, less than 22 hours, less than 24 hours, less than 26 hours, less than 28 hours, less than 30 hours, less than 32 hours, less than 34 hours, or less than 36 hours. In other embodiments, a method comprising a pre-enrichment step disclosed herein, an enrichment step disclosed herein, a purification step disclosed herein, and a detection step disclosed herein can be performed to completion in, e.g., less than 18 hours, less than 20 hours, less than 22 hours, less than 24 hours, less than 26 hours, less than 28 hours, less than 30 hours, less than 32 hours, less than 34 hours, or less than 36 hours.

In other embodiments, a method comprising a first pre-enrichment step disclosed herein, an enrichment step disclosed herein and a second pre-enrichment step disclosed herein can be performed to completion in, e.g., about 18 hours, about 20 hours, about 22 hours, about 24 hours, about 26 hours, about 28 hours, about 30 hours, about 32 hours, about 34 hours, or about 36 hours. In still other embodiments, a method comprising a first pre-enrichment step disclosed herein, an enrichment step disclosed herein, a second pre-enrichment step disclosed herein and a detection step disclosed herein can be performed to completion in, e.g., about 18 hours, about 20 hours, about 22 hours, about 24 hours, about 26 hours, about 28 hours, about 30 hours, about 32 hours, about 34 hours, or about 36 hours. In other embodiments, a method comprising a first pre-enrichment step disclosed herein, an enrichment step disclosed herein, a purification step disclosed herein, a second pre-enrichment step disclosed herein, and a detection step disclosed herein can be performed to completion in, e.g., about 18 hours, about 20 hours, about 22 hours, about 24 hours, about 26 hours, about 28 hours, about 30 hours, about 32 hours, about 34 hours, or about 36 hours. In other embodiments, a method comprising a first pre-enrichment step disclosed herein, an enrichment step disclosed herein, a purification step disclosed herein, a second pre-enrichment step disclosed herein, a purification step disclosed herein and a detection step disclosed herein can be performed to completion in, e.g., about 18 hours, about 20 hours, about 22 hours, about 24 hours, about 26 hours, about 28 hours, about 30 hours, about 32 hours, about 34 hours, or about 36 hours.

In other embodiments, a method comprising a first pre-enrichment step disclosed herein, an enrichment step disclosed herein and a second pre-enrichment step disclosed herein can be performed to completion in, e.g., less than 18 hours, less than 20 hours, less than 22 hours, less than 24 hours, less than 26 hours, less than 28 hours, less than 30 hours, less than 32 hours, less than 34 hours, or less than 36 hours. In still other embodiments, a method comprising a first pre-enrichment step disclosed herein, an enrichment step disclosed herein, a second pre-enrichment step disclosed herein and a detection step disclosed herein can be performed to completion in, e.g., less than 18 hours, less than 20 hours, less than 22 hours, less than 24 hours, less than 26 hours, less than 28 hours, less than 30 hours, less than 32 hours, less than 34 hours, or less than 36 hours. In other embodiments, a method comprising a first pre-enrichment step disclosed herein, an enrichment step disclosed herein, a purification step disclosed herein, a second pre-enrichment step disclosed herein and a detection step disclosed herein can be performed to completion in, e.g., less than 18 hours, less than 20 hours, less than 22 hours, less than 24 hours, less than 26 hours, less than 28 hours, less than 30 hours, less than 32 hours, less than 34 hours, or less than 36 hours. In other embodiments, a method comprising a first pre-enrichment step disclosed herein, an enrichment step disclosed herein, a purification step disclosed herein, a second pre-enrichment step disclosed herein, a purification step disclosed herein and a detection step disclosed herein can be performed to completion in, e.g., less than 18 hours, less than 20 hours, less than 22 hours, less than 24 hours, less than 26 hours, less than 28 hours, less than 30 hours, less than 32 hours, less than 34 hours, or less than 36 hours.

In other embodiments, a method disclosed herein can be performed to completion in, e.g., about 18 hours to about 20 hours, about 18 hours to about 22 hours, about 18 hours to about 24 hours, about 18 hours to about 26 hours, about 18 hours to about 28 hours, about 18 hours to about 30 hours, about 18 hours to about 32 hours, about 18 hours to about 34 hours, about 18 hours to about 36 hours, about 20 hours to about 22 hours, about 20 hours to about 24 hours, about 20 hours to about 26 hours, about 20 hours to about 28 hours, about 20 hours to about 30 hours, about 20 hours to about 32 hours, about 20 hours to about 34 hours, about 20 hours to about 36 hours, about 22 hours to about 24 hours, about 22 hours to about 26 hours, about 22 hours to about 28 hours, about 22 hours to about 30 hours, about 22 hours to about 32 hours, about 22 hours to about 34 hours, about 22 hours to about 36 hours, about 24 hours to about 26 hours, about 24 hours to about 28 hours, about 24 hours to about 30 hours, about 24 hours to about 32 hours, about 24 hours to about 34 hours, about 24 hours to about 36 hours, about 26 hours to about 28 hours, about 26 hours to about 30 hours, about 26 hours to about 32 hours, about 26 hours to about 34 hours, about 26 hours to about 36 hours, about 28 hours to about 30 hours, about 28 hours to about 32 hours, about 28 hours to about 34 hours, about 28 hours to about 36 hours, about 30 hours to about 32 hours, about 30 hours to about 34 hours, about 30 hours to about 36 hours, about 32 hours to about 34 hours, about 32 hours to about 36 hours, or about 34 hours to about 36 hours.

In yet other embodiments, a method comprising a pre-enrichment step disclosed herein and an enrichment step disclosed herein can be performed to completion in, e.g., about 18 hours to about 20 hours, about 18 hours to about 22 hours, about 18 hours to about 24 hours, about 18 hours to about 26 hours, about 18 hours to about 28 hours, about 18 hours to about 30 hours, about 18 hours to about 32 hours, about 18 hours to about 34 hours, about 18 hours to about 36 hours, about 20 hours to about 22 hours, about 20 hours to about 24 hours, about 20 hours to about 26 hours, about 20 hours to about 28 hours, about 20 hours to about 30 hours, about 20 hours to about 32 hours, about 20 hours to about 34 hours, about 20 hours to about 36 hours, about 22 hours to about 24 hours, about 22 hours to about 26 hours, about 22 hours to about 28 hours, about 22 hours to about 30 hours, about 22 hours to about 32 hours, about 22 hours to about 34 hours, about 22 hours to about 36 hours, about 24 hours to about 26 hours, about 24 hours to about 28 hours, about 24 hours to about 30 hours, about 24 hours to about 32 hours, about 24 hours to about 34 hours, about 24 hours to about 36 hours, about 26 hours to about 28 hours, about 26 hours to about 30 hours, about 26 hours to about 32 hours, about 26 hours to about 34 hours, about 26 hours to about 36 hours, about 28 hours to about 30 hours, about 28 hours to about 32 hours, about 28 hours to about 34 hours, about 28 hours to about 36 hours, about 30 hours to about 32 hours, about 30 hours to about 34 hours, about 30 hours to about 36 hours, about 32 hours to about 34 hours, about 32 hours to about 36 hours, or about 34 hours to about 36 hours.

In still other embodiments, a method comprising a pre-enrichment step disclosed herein, an enrichment step disclosed herein and a detection step disclosed herein can be performed to completion in, e.g., about 18 hours to about 20 hours, about 18 hours to about 22 hours, about 18 hours to about 24 hours, about 18 hours to about 26 hours, about 18 hours to about 28 hours, about 18 hours to about 30 hours, about 18 hours to about 32 hours, about 18 hours to about 34 hours, about 18 hours to about 36 hours, about 20 hours to about 22 hours, about 20 hours to about 24 hours, about 20 hours to about 26 hours, about 20 hours to about 28 hours, about 20 hours to about 30 hours, about 20 hours to about 32 hours, about 20 hours to about 34 hours, about 20 hours to about 36 hours, about 22 hours to about 24 hours, about 22 hours to about 26 hours, about 22 hours to about 28 hours, about 22 hours to about 30 hours, about 22 hours to about 32 hours, about 22 hours to about 34 hours, about 22 hours to about 36 hours, about 24 hours to about 26 hours, about 24 hours to about 28 hours, about 24 hours to about 30 hours, about 24 hours to about 32 hours, about 24 hours to about 34 hours, about 24 hours to about 36 hours, about 26 hours to about 28 hours, about 26 hours to about 30 hours, about 26 hours to about 32 hours, about 26 hours to about 34 hours, about 26 hours to about 36 hours, about 28 hours to about 30 hours, about 28 hours to about 32 hours, about 28 hours to about 34 hours, about 28 hours to about 36 hours, about 30 hours to about 32 hours, about 30 hours to about 34 hours, about 30 hours to about 36 hours, about 32 hours to about 34 hours, about 32 hours to about 36 hours, or about 34 hours to about 36 hours.

In other embodiments, a method comprising a pre-enrichment step disclosed herein, an enrichment step disclosed herein, a purification step disclosed herein, and a detection step disclosed herein can be performed to completion in, e.g., about 18 hours to about 20 hours, about 18 hours to about 22 hours, about 18 hours to about 24 hours, about 18 hours to about 26 hours, about 18 hours to about 28 hours, about 18 hours to about 30 hours, about 18 hours to about 32 hours, about 18 hours to about 34 hours, about 18 hours to about 36 hours, about 20 hours to about 22 hours, about 20 hours to about 24 hours, about 20 hours to about 26 hours, about 20 hours to about 28 hours, about 20 hours to about 30 hours, about 20 hours to about 32 hours, about 20 hours to about 34 hours, about 20 hours to about 36 hours, about 22 hours to about 24 hours, about 22 hours to about 26 hours, about 22 hours to about 28 hours, about 22 hours to about 30 hours, about 22 hours to about 32 hours, about 22 hours to about 34 hours, about 22 hours to about 36 hours, about 24 hours to about 26 hours, about 24 hours to about 28 hours, about 24 hours to about 30 hours, about 24 hours to about 32 hours, about 24 hours to about 34 hours, about 24 hours to about 36 hours, about 26 hours to about 28 hours, about 26 hours to about 30 hours, about 26 hours to about 32 hours, about 26 hours to about 34 hours, about 26 hours to about 36 hours, about 28 hours to about 30 hours, about 28 hours to about 32 hours, about 28 hours to about 34 hours, about 28 hours to about 36 hours, about 30 hours to about 32 hours, about 30 hours to about 34 hours, about 30 hours to about 36 hours, about 32 hours to about 34 hours, about 32 hours to about 36 hours, or about 34 hours to about 36 hours.

In other embodiments, a method comprising a first pre-enrichment step disclosed herein, an enrichment step disclosed herein and a second pre-enrichment step disclosed herein can be performed to completion in, e.g., about 18 hours to about 20 hours, about 18 hours to about 22 hours, about 18 hours to about 24 hours, about 18 hours to about 26 hours, about 18 hours to about 28 hours, about 18 hours to about 30 hours, about 18 hours to about 32 hours, about 18 hours to about 34 hours, about 18 hours to about 36 hours, about 20 hours to about 22 hours, about 20 hours to about 24 hours, about 20 hours to about 26 hours, about 20 hours to about 28 hours, about 20 hours to about 30 hours, about 20 hours to about 32 hours, about 20 hours to about 34 hours, about 20 hours to about 36 hours, about 22 hours to about 24 hours, about 22 hours to about 26 hours, about 22 hours to about 28 hours, about 22 hours to about 30 hours, about 22 hours to about 32 hours, about 22 hours to about 34 hours, about 22 hours to about 36 hours, about 24 hours to about 26 hours, about 24 hours to about 28 hours, about 24 hours to about 30 hours, about 24 hours to about 32 hours, about 24 hours to about 34 hours, about 24 hours to about 36 hours, about 26 hours to about 28 hours, about 26 hours to about 30 hours, about 26 hours to about 32 hours, about 26 hours to about 34 hours, about 26 hours to about 36 hours, about 28 hours to about 30 hours, about 28 hours to about 32 hours, about 28 hours to about 34 hours, about 28 hours to about 36 hours, about 30 hours to about 32 hours, about 30 hours to about 34 hours, about 30 hours to about 36 hours, about 32 hours to about 34 hours, about 32 hours to about 36 hours, or about 34 hours to about 36 hours.

In still other embodiments, a method comprising a first pre-enrichment step disclosed herein, an enrichment step disclosed herein, a second pre-enrichment step disclosed herein and a detection step disclosed herein can be performed to completion in, e.g., about 18 hours to about 20 hours, about 18 hours to about 22 hours, about 18 hours to about 24 hours, about 18 hours to about 26 hours, about 18 hours to about 28 hours, about 18 hours to about 30 hours, about 18 hours to about 32 hours, about 18 hours to about 34 hours, about 18 hours to about 36 hours, about 20 hours to about 22 hours, about 20 hours to about 24 hours, about 20 hours to about 26 hours, about 20 hours to about 28 hours, about 20 hours to about 30 hours, about 20 hours to about 32 hours, about 20 hours to about 34 hours, about 20 hours to about 36 hours, about 22 hours to about 24 hours, about 22 hours to about 26 hours, about 22 hours to about 28 hours, about 22 hours to about 30 hours, about 22 hours to about 32 hours, about 22 hours to about 34 hours, about 22 hours to about 36 hours, about 24 hours to about 26 hours, about 24 hours to about 28 hours, about 24 hours to about 30 hours, about 24 hours to about 32 hours, about 24 hours to about 34 hours, about 24 hours to about 36 hours, about 26 hours to about 28 hours, about 26 hours to about 30 hours, about 26 hours to about 32 hours, about 26 hours to about 34 hours, about 26 hours to about 36 hours, about 28 hours to about 30 hours, about 28 hours to about 32 hours, about 28 hours to about 34 hours, about 28 hours to about 36 hours, about 30 hours to about 32 hours, about 30 hours to about 34 hours, about 30 hours to about 36 hours, about 32 hours to about 34 hours, about 32 hours to about 36 hours, or about 34 hours to about 36 hours.

In other embodiments, a method comprising a first pre-enrichment step disclosed herein, an enrichment step disclosed herein, a purification step disclosed herein, a second pre-enrichment step disclosed herein and a detection step disclosed herein can be performed to completion in, e.g., about 18 hours to about 20 hours, about 18 hours to about 22 hours, about 18 hours to about 24 hours, about 18 hours to about 26 hours, about 18 hours to about 28 hours, about 18 hours to about 30 hours, about 18 hours to about 32 hours, about 18 hours to about 34 hours, about 18 hours to about 36 hours, about 20 hours to about 22 hours, about 20 hours to about 24 hours, about 20 hours to about 26 hours, about 20 hours to about 28 hours, about 20 hours to about 30 hours, about 20 hours to about 32 hours, about 20 hours to about 34 hours, about 20 hours to about 36 hours, about 22 hours to about 24 hours, about 22 hours to about 26 hours, about 22 hours to about 28 hours, about 22 hours to about 30 hours, about 22 hours to about 32 hours, about 22 hours to about 34 hours, about 22 hours to about 36 hours, about 24 hours to about 26 hours, about 24 hours to about 28 hours, about 24 hours to about 30 hours, about 24 hours to about 32 hours, about 24 hours to about 34 hours, about 24 hours to about 36 hours, about 26 hours to about 28 hours, about 26 hours to about 30 hours, about 26 hours to about 32 hours, about 26 hours to about 34 hours, about 26 hours to about 36 hours, about 28 hours to about 30 hours, about 28 hours to about 32 hours, about 28 hours to about 34 hours, about 28 hours to about 36 hours, about 30 hours to about 32 hours, about 30 hours to about 34 hours, about 30 hours to about 36 hours, about 32 hours to about 34 hours, about 32 hours to about 36 hours, or about 34 hours to about 36 hours.

In other embodiments, a method comprising a first pre-enrichment step disclosed herein, an enrichment step disclosed herein, a purification step disclosed herein, a second pre-enrichment step disclosed herein, a purification step disclosed herein and a detection step disclosed herein can be performed to completion in, e.g., about 18 hours to about 20 hours, about 18 hours to about 22 hours, about 18 hours to about 24 hours, about 18 hours to about 26 hours, about 18 hours to about 28 hours, about 18 hours to about 30 hours, about 18 hours to about 32 hours, about 18 hours to about 34 hours, about 18 hours to about 36 hours, about 20 hours to about 22 hours, about 20 hours to about 24 hours, about 20 hours to about 26 hours, about 20 hours to about 28 hours, about 20 hours to about 30 hours, about 20 hours to about 32 hours, about 20 hours to about 34 hours, about 20 hours to about 36 hours, about 22 hours to about 24 hours, about 22 hours to about 26 hours, about 22 hours to about 28 hours, about 22 hours to about 30 hours, about 22 hours to about 32 hours, about 22 hours to about 34 hours, about 22 hours to about 36 hours, about 24 hours to about 26 hours, about 24 hours to about 28 hours, about 24 hours to about 30 hours, about 24 hours to about 32 hours, about 24 hours to about 34 hours, about 24 hours to about 36 hours, about 26 hours to about 28 hours, about 26 hours to about 30 hours, about 26 hours to about 32 hours, about 26 hours to about 34 hours, about 26 hours to about 36 hours, about 28 hours to about 30 hours, about 28 hours to about 32 hours, about 28 hours to about 34 hours, about 28 hours to about 36 hours, about 30 hours to about 32 hours, about 30 hours to about 34 hours, about 30 hours to about 36 hours, about 32 hours to about 34 hours, about 32 hours to about 36 hours, or about 34 hours to about 36 hours.

Aspects of the present specification disclose, in part, a pathogen analysis kit to carry out the method of detecting a pathogen disclosed herein. A pathogen analysis kit disclosed herein contains components necessary for the detection of the pathogen of interest. In some aspects, a pathogen analysis kit disclosed herein components necessary for the detection of a single pathogen of interest. In some aspects, a pathogen analysis kit disclosed herein components necessary for the detection of a plurality of pathogens of interest.

In some embodiment, a pathogen analysis kit disclosed herein typically comprises a pre-enrichment media and an enrichment media. In some embodiment, a pathogen analysis kit disclosed herein typically comprises a pre-enrichment media, an enrichment media, and a detection solution. In some embodiment, a pathogen analysis kit disclosed herein typically comprises a pre-enrichment media, an enrichment media, a detection solution and an electrochemical biosensor.

In some embodiment, a pathogen analysis kit disclosed herein typically comprises a first and second pre-enrichment media and an enrichment media. In some embodiment, a pathogen analysis kit disclosed herein typically comprises a first and second pre-enrichment media, an enrichment media, and a detection solution. In some embodiment, a pathogen analysis kit disclosed herein typically comprises a first and second pre-enrichment media, an enrichment media, a detection solution and an electrochemical biosensor.

In some embodiment, a pathogen analysis kit disclosed herein typically comprises a pre-enrichment media, an enrichment media, and immunmagnetic particles capable of binding to a pathogen of interest. In some embodiment, a pathogen analysis kit disclosed herein typically comprises a pre-enrichment media, an enrichment media, immunmagnetic particles capable of binding to a pathogen of interest, and a magnetic source used to capture the immunoparticles. In some embodiment, a pathogen analysis kit disclosed herein typically comprises a pre-enrichment media, an enrichment media, immunmagnetic particles capable of binding to a pathogen of interest, and a detection solution. In some embodiment, a pathogen analysis kit disclosed herein typically comprises a pre-enrichment media, an enrichment media, immunmagnetic particles capable of binding to a pathogen of interest, a magnetic source used to capture the immunoparticles, and a detection solution. In some embodiment, a pathogen analysis kit disclosed herein typically comprises a pre-enrichment media, an enrichment media, immunmagnetic particles capable of binding to a pathogen of interest, a detection solution, and an electrochemical biosensor. In some embodiment, a pathogen analysis kit disclosed herein typically comprises a pre-enrichment media, an enrichment media, immunmagnetic particles capable of binding to a pathogen of interest, a detection solution, a magnetic source used to capture the immunoparticles, and an electrochemical biosensor.

In some embodiment, a pathogen analysis kit disclosed herein typically comprises a first and second pre-enrichment media, an enrichment media, and immunmagnetic particles capable of binding to a pathogen of interest. In some embodiment, a pathogen analysis kit disclosed herein typically comprises a first and second pre-enrichment media, an enrichment media, immunmagnetic particles capable of binding to a pathogen of interest, and a magnetic source used to capture the immunoparticles. In some embodiment, a pathogen analysis kit disclosed herein typically comprises a first and second pre-enrichment media, an enrichment media, immunmagnetic particles capable of binding to a pathogen of interest, and a detection solution. In some embodiment, a pathogen analysis kit disclosed herein typically comprises a first and second pre-enrichment media, an enrichment media, immunmagnetic particles capable of binding to a pathogen of interest, a magnetic source used to capture the immunoparticles, and a detection solution. In some embodiment, a pathogen analysis kit disclosed herein typically comprises a first and second pre-enrichment media, an enrichment media, immunmagnetic particles capable of binding to a pathogen of interest, a detection solution, and an electrochemical biosensor. In some embodiment, a pathogen analysis kit disclosed herein typically comprises a first and second pre-enrichment media, an enrichment media, immunmagnetic particles capable of binding to a pathogen of interest, a detection solution, a magnetic source used to capture the immunoparticles, and an electrochemical biosensor.

A pathogen analysis kit disclosed herein may further comprise an instrument which is capable of measuring and/or analyzing potentiometric, voltammetric, amperometric and/or impedance/conductance parameters.

A pathogen analysis kit disclosed herein may further comprise a suitable container, for example, a vessel, vials, tubes, mini- or microfuge tubes, test tube, flask, bottle, syringe or other container. Where an additional component or agent is provided, the kit can contain one or more additional containers into which this agent or component may be placed. Kits herein will also typically include a means for containing the agent (e.g. a vessel), composition and any other reagent containers in close confinement for commercial sale. Such containers may include injection or blow-molded plastic containers into which the desired vials are retained.

A pathogen analysis kit disclosed herein may further comprise a labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., hard disk, flash memory), optical disk such as CD- or DVD-ROM/RAM, DVD, MP3, magnetic tape, or an electrical storage media such as RAM and ROM or hybrids of these such as magnetic/optical storage media, FLASH media or memory type cards. Labels or inserts may include identifying information of one or more components therein, amounts used for one or more components therein, step by step instructions of how to perform a method of detecting a pathogen of interest. Labels or inserts can include information identifying manufacturer information, lot numbers, manufacturer location and date and patent information.

Aspects of the present specification may also be described as follows:

1. A method of detecting a pathogen in a sample the method comprising the steps: a) incubation of the sample in a pre-enrichment comprising a low growth nutrient component, a growth inhibiting agent, and a surfactant with bacteriostatic or bactericidal action, wherein the incubation at 37° C. for about 6 hours to about 24 hours; b) incubating an aliquot of pre-enrichment media from step (a) in an enrichment media, the enrichment media comprising a high growth nutrient component and ferric ammonium citrate, wherein the incubation at about 15° C. to about 50° C. for about 2 hours to about 24 hours; and c) detecting the presence of absence of a pathogen by analyzing an aliquot of enrichment media from step (b).
2. The method according to embodiment 1, wherein the low growth nutrient component is a peptone.
3. The method according to embodiment 2, wherein the peptone is a peptone from an animal source or a peptone from a plant source.
4. The method according to embodiment 3, wherein the peptone from an animal source is an acid casein peptone, a bacteriological peptone, a beef extract powder, a casein peptone, a casein cc peptone, a gelatin peptone, a meat peptone, a polypeptone proteose peptone, or a proteose peptone No 3.
5. The method according to embodiment 3, wherein the peptone from a plant source is a malt extract, a soya peptone, or a yeast extract.
6. The method according to any one of embodiments 1-5, wherein the surfactant is at a concentration of about 0.001 (v/v) to about 10.0% (v/v).
7. The method according to any one of embodiments 1-6, wherein the surfactant is an ionic surfactant, a zwitterionic (amphoteric) surfactant, or a non-ionic surfactant.
8. The method according to embodiment 7, wherein the ionic surfactant is an anion surfactant or cationic surfactant.
9. The method according to embodiment 8, wherein the anionic surfactant is an alkyl sulfate, an alkyl ether sulfate, a docusate, a sulfonate fluorosurfactant, an alkyl benzene sulfonate, an alkyl aryl ether phosphate, an alkyl ether phosphate, an; alkyl carboxylate, a sodium lauroyl sarcosinate, or a carboxylate fluorosurfactant.
10. The method according to embodiment 8, wherein the cationic surfactant is an alkyltrimethylammonium salt, cetylpyridinium chloride (CPC), polyethoxylated tallow amine (POEA), benzalkonium chloride (BAC), benzethonium chloride (BZT), 5-bromo-5-nitro-1,3-dioxane, dimethyldioctadecylammonium chloride, dioctadecyldimethylammonium bromide (DODAB), a pH-dependent primary amine, a pH-dependent secondary amine, or a pH-dependent tertiary amine.
11. The method according to embodiment 7, wherein the zwitterionic surfactant is 3-[(3-cholamidopropyl)dimethylammonio]-1-propanesulfonate (CHAPS), a sultaine, a, betaine, or a lecithin.
12. The method according to embodiment 7, wherein the non-ionic surfactant is a polyoxyethylene glycol sorbitan alkyl ester, a poloxamer, an alkyl phenol polyglycol ether, a polyethylene glycol alkyl aryl ether, a polyoxyethylene glycol alkyl ether, 2-dodecoxyethanol, a polyoxyethylene glycol octyl phenol ether, a nonylphenol ethoxylate, a polyoxyethylene glycol alkylphenol ether, a phenoxypolyethoxylethanol, a glucoside alkyl ether, a maltoside alkyl ether, a thioglucoside alkyl ether, a digitonin, a glycerol alkyl ester, an alkyl aryl polyether sulfate, an alcohol sulfonate, a sorbitan alkyl ester, a cocamide ethanolamine, sucrose monolaurate, dodecyl dimethylamine oxide, or sodium cholate.
13. The method according to any one of embodiments 1-6, where the surfactant is tetradecyl sodium dodecyl sulfate, octadecyl sulphate, or 7-ethyl-2-methyl-4-undecyl sodium sulphate.
14. The method according to any one of embodiments 1-13, where the growth inhibiting agent is at a concentration of about 0.001 (v/v) to about 10.0% (v/v).
15. The method according to any one of embodiments 1-14, wherein the growth inhibiting agent is a triarylmethane dye.
16. The method according to embodiment 15, where the triarylmethane dye is a methyl violet dye, a fuchsine dye, a phenol dye, or a malachite green dye.
17. The method according to embodiment 16, where the methyl violet dye is methyl violet 2B, methyl violet 6B, or methyl violet 10B.
18. The method according to embodiment 16, where the fuchsine dye is pararosaniline, fuchsine, new fuchsine, fuchsin basic violet, or fuchine acid.
19. The method according to embodiment 16, where the phenol dye is phenol red, chlorophenol red, or cresol red.
20. The method according to embodiment 16, where the malachite green dye is malachite green or brilliant green.
21. The method according to embodiment 15, where the triarylmethane dye is aluminon, aniline Blue WS, aurin, aurintricarboxylic acid, brilliant blue FCF, brilliant green, bromocresol green, bromocresol purple, bromophenol blue, bromopyrogallol red, bromothymol blue, bromsulphthalein, chlorophenol red, coomassie brilliant blue, cresol red, crystal violet, crystal violet lactone, ethyl green, fast green FCF, fluoran, fuchsine, fuchsine acid, fuchsin basic violet, gentian, green S, light green SF yellowish, malachite green, methyl blue, methyl violet, new fuchsine, pararosaniline, patent blue V, phenol red, phenolphthalein, rose bengal, thymolphthalein, victoria blue BO, water blue, xylene cyanol, or xylenol orange.
22. The method according to any one of embodiments 1-22, wherein the pre-enrichment media further comprises a growth enhancing agent.

23. The method according to embodiment 22, wherein the growth enhancing agent is a siderophore.
24. The method according to embodiment 23, wherein the siderophore is Aerobactin, Alcaligin, Azotobactin, Bacillibactin, Desferrioxamine B, Desferrioxamine E, Enterobactin, Ferrichrome, Ferrioxiamina-B, Ferrioxiamina-E, Fusarinine C, Mycobactin, Ornibactin, Petrobactin, Pyoverdine, Pyochelin, Salmochelin, Staphyloferring A, Vibriobactin, or Yersiniabactin.
25. The method according to any one of embodiments 1-24, wherein the aliquot of pre-enrichment media in step (b) is about 1/50 to about 1/500 a volume of an enrichment media used in step (b).
26. The method according to any one of embodiments 1-25, wherein the high growth nutrient component is a peptone.
27. The method according to embodiment 26, wherein the peptone is a peptone from an animal source or a peptone from a plant source.
28. The method according to embodiment 27, wherein the peptone from an animal source is an acid casein peptone, a bacteriological peptone, a beef extract powder, a casein peptone, a casein cc peptone, a gelatin peptone, a meat peptone, a polypeptone proteose peptone, or a proteose peptone No 3.
29. The method according to embodiment 27, wherein the peptone from a plant source is a malt extract, a soya peptone, or a yeast extract.
30. The method according to any one of embodiments 1-29, wherein the high growth nutrient component is at a concentration of about 1.0 (v/v) to about 4.0% (v/v).
31. The method according to any one of embodiments 1-29, wherein the ammonium ferric citrate is at a concentration of about 0.1 mg/mL to about 15 mg/mL.
32. The method according to any one of embodiments 1-31, wherein the enrichment media further comprises a growth enhancing agent.
33. The method according to embodiment 32, wherein the growth enhancing agent is a siderophore.
34. The method according to embodiment 33, wherein the siderophore is Aerobactin, Alcaligin, Azotobactin, Bacillibactin, Desferrioxamine B, Desferrioxamine E, Enterobactin, Ferrichrome, Ferrioxiamina-B, Ferrioxiamina-E, Fusarinine C, Mycobactin, Ornibactin, Petrobactin, Pyoverdine, Pyochelin, Salmochelin, Staphyloferring A, Vibriobactin, or Yersiniabactin.
35. The method according to any one of embodiments 1-34, wherein detection step (c) is performed using a sensor-based detection method, a nucleic acid-based detection method, a protein-based detection method, an activity-based detection method, or a growth-based detection method.
36. The method according to embodiment 35, wherein the sensor-based detection method is an electrochemical detection method.
37. The method according to embodiment 36, wherein the electrochemical detection method comprises an enzymatic biosensor, a DNA sensor, or an immunosensor.
38. The method according to embodiment 36, wherein the electrochemical detection method measures potentiometric parameters, amperometric parameters, voltametric parameters, impedimetric/conductimetric parameters, or any combination thereof.
39. The method according to embodiment 35, wherein the nucleic acid-based detection method comprises a DNA-based detection method or an RNA-based detection method.
40. The method according to embodiment 39, wherein the DNA-based detection method comprises a Southern blot analysis, a PCR-based assay, a sequence analysis, an immuno-based detection assay, or a hybridization assays using FRET, polarization or other fluorescent, chemiluminescent or bioiluminescent detection.
41. The method according to embodiment 40, wherein the PCR-based assay comprises a real-time PCR-based assay.
42. The method according to embodiment 39, wherein the RNA-based detection method comprises a Northern blot analysis, a RT-PCR-based assay, a RNA sequence analysis, an immuno-based detection assay, or a hybridization assays using FRET, polarization or other fluorescent, chemiluminescent or bioiluminescent detection.
43. The method according to embodiment 35, wherein the protein-based detection method is a gel-based detection method, an immuno-based detection method or a protein-interaction-based method.
44. The method according to embodiment 43, wherein the immuno-based detection method comprises a Western blot analysis, an ELISA, or an immunoprecipitation assay.
45. The method according to embodiment 35, wherein the activity-based detection method comprises an enzymatic activity assay or an assay based on protein function.
46. The method according to embodiment 45, wherein the enzymatic activity assay uses a spetrophotometric detection method measures a disappearance of a substrate or a formation of a product.
47. The method according to embodiment 35, wherein the growth-based detection method comprises a plating assays measuring colony formation or spectrophotometer assays measuring cell density.
48. The method according to any one of embodiments 1-47, wherein the pathogen is a prion, a virus, a bacterium, a fungus, a protozoan, a helimenth, or a parasite.
49. The method according to embodiment 48, wherein the virus belongs to the family Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, or Togaviridae.
50. The method according to embodiment 48, wherein the bacteria belongs to the genus *Bacillus, Bordetella, Borrelia, Brucella, Campylobacter, Chlamydia, Chlamydophila, Clostridium, Corynebacterium, Enterobacter, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio*, or *Yersinia*.
51. The method according to embodiment 48, wherein the fungus belongs to the genus *Asperfillus, Canidia, Cryptococcus, Histoplasma, Pneumocystis*, or *Stachybotrys*.
52. The method according to embodiment 48, wherein the protozoan belongs to the genus *Acanthamoeba, Balamuthia, Cryptosporidium, Dientamoeba, Endolimax, Entamoeba, Giardia, Iodamoeba, Leishmania, Naegleria, Plasmodium, Sappinia, Toxoplasma, Trichomonas*, or *Trypanosoma*.
53. A pathogen analysis kit comprising a pre-enrichment media and an enrichment media.
54. The pathogen analysis kit according to embodiment 53, further comprising a detection solution.
55. The pathogen analysis kit according to embodiment 53 or embodiment 54, further and an electrochemical biosensor.

56. The pathogen analysis kit according to any one of embodiments 53-55, further comprising immunmagnetic particles capable of binding to a pathogen of interest.
57. The pathogen analysis kit according to any one of embodiments 53-56, further comprising a magnetic source used to capture the immunoparticles.
58. The pathogen analysis kit according to any one of embodiments 53-57, further comprising an instrument which is capable of measuring and/or analyzing potentiometric, voltammetric, amperometric and/or impedance/conductance parameters.
59. The pathogen analysis kit according to any one of embodiments 53-58, further comprising a suitable container.
60. The pathogen analysis kit according to any one of embodiments 53-59, further comprising a label or an insert.

Aspects of the present specification may also be described as follows:

1. A method of detecting a *Salmonella* live vaccine strain in a sample the method comprising the steps: a) incubation of the sample in a first liquid pre-enrichment media, the first pre-enrichment media comprising 2 g/L to 6 g/L of a peptone, 0.5 g/L to 4.5 g/L Bile Salts, 0.5 g/L to 4.5 g/L Meat Extract, 0.5 g/L to 4.5 g/L of a first growth inhibiting agent, 0.5 g/L to 4.5 g/L of a second growth inhibiting agent, 0.001 g/L to 0.008 g/L of a third growth inhibiting agent, and 0.001 g/L to 0.008 g/L of a fourth growth inhibiting agent, wherein the incubation at about 34° C. to about 40° C. for about 5 hours to about 10 hours; b) incubating an aliquot of first pre-enrichment media from step (a) in a liquid enrichment media, the enrichment media comprising 6 g/L to 10 g/L of a peptone, 3 g/L to 7 g/L Bile Salts, 2 g/L to 6 g/L Meat Extract, 2 g/L to 6 g/L of a first growth inhibiting agent, 2 g/L to 6 g/L of a second growth inhibiting agent, 0.001 g/L to 0.008 g/L of a third growth inhibiting agent, and 0.001 g/L to 0.008 g/L of a fourth growth inhibiting agent, wherein the incubation at about 34° C. to about 45° C. for about 14 hours to about 20 hours; c) purifying the liquid enrichment medium or an aliquot thereof to increase concentration of the *Salmonella* live vaccine strain and/or decrease contaminants; d) incubating an aliquot of enrichment media from step (c) in a second liquid pre-enrichment media, the second pre-enrichment media comprising 2 g/L to 6 g/L of a peptone, 0.5 g/L to 4.5 g/L Bile Salts, 0.5 g/L to 4.5 g/L Meat Extract, 0.5 g/L to 4.5 g/L of a first growth inhibiting agent, 0.5 g/L to 4.5 g/L of a second growth inhibiting agent, 0.001 g/L to 0.008 g/L of a third growth inhibiting agent, and 0.001 g/L to 0.008 g/L of a fourth growth inhibiting agent, wherein the incubation at about 34° C. to about 45° C. for about 1 hours to about 5 hours; and e) detecting the presence of absence of a *Salmonella* live vaccine strain by analyzing an aliquot of the second liquid pre-enrichment media from step (d).
2. The method according to embodiment 1, wherein the peptone in step (a), step (b) and/or step (d) is a peptone from an animal source or a peptone from a plant source.
3. The method according to embodiment 2, wherein the peptone from an animal source is an acid casein peptone, a bacteriological peptone, a beef extract powder, a casein peptone, a casein cc peptone, a gelatin peptone, a meat peptone, a polypeptone proteose peptone, or a proteose peptone No 3.
4. The method according to embodiment 3, wherein the peptone from a plant source is a malt extract, a soya peptone, or a yeast extract.
5. The method according to any one of embodiments 1-4, wherein the first growth inhibiting agent in step (a), step (b) and/or step (d) is a first iodine compound.
6. The method according to embodiment 5, wherein the first iodine compound is iodine or potassium iodine.
7. The method according to any one of embodiments 1-6, wherein the second growth inhibiting agent in step (a), step (b) and/or step (d) is a second iodine compound.
8. The method according to embodiment 7, wherein the second iodine compound is iodine or potassium iodine.
9. The method according to any one of embodiments 1-8, wherein the third growth inhibiting agent in step (a), step (b) and/or step (d) is an aminocoumarin antibiotic.
10. The method according to embodiment 9, wherein the aminocoumarin antibiotic is Novobiocin, Albamycin, Coumermycin or Clorobiocin.
11. The method according to any one of embodiments 1-10, wherein the fourth growth inhibiting agent in step (a), step (b) and/or step (d) is a triarylmethane dye.
12. The method according to embodiment 11, wherein the triarylmethane dye is a methyl violet dye, a fuchsine dye, a phenol dye, or a malachite green dye.
13. The method according to embodiment 12, wherein the methyl violet dye is methyl violet 2B, methyl violet 6B, or methyl violet 10B.
14. The method according to embodiment 12, wherein the fuchsine dye is pararosaniline, fuchsine, new fuchsine, fuchsin basic violet, or fuchine acid.
15. The method according to embodiment 12, wherein the phenol dye is phenol red, chlorophenol red, or cresol red.
16. The method according to embodiment 12, wherein the malachite green dye is malachite green or brilliant green.
17. The method according to embodiment 11, wherein the triarylmethane dye is aluminon, aniline Blue WS, aurin, aurintricarboxylic acid, brilliant blue FCF, brilliant green, bromocresol green, bromocresol purple, bromophenol blue, bromopyrogallol red, bromothymol blue, bromsulphthalein, chlorophenol red, coomassie brilliant blue, cresol red, crystal violet, crystal violet lactone, ethyl green, fast green FCF, fluoran, fuchsine, fuchsine acid, fuchsin basic violet, gentian, green S, light green SF yellowish, malachite green, methyl blue, methyl violet, new fuchsine, pararosaniline, patent blue V, phenol red, phenolphthalein, rose bengal, thymolphthalein, victoria blue BO, water blue, xylene cyanol, or xylenol orange.
18. The method according to any one of embodiments 1-17, wherein the amount of peptone in step (a) and/or step (d) is 3 g/L to 5 g/L, 4 g/L to 4.6 g/L, 4.2 g/L to 4.4 g/L or 4.3 g/L.
19. The method according to any one of embodiments 1-18, wherein the amount of Bile Salts in step (a) and/or step (d) is 0.5 g/L to 3.5 g/L, 2.1 g/L to 2.7 g/L, 2.3 g/L to 2.5 g/L or 2.4 g/L.
20. The method according to any one of embodiments 1-19, wherein the amount of Meat Extract in step (a) and/or step (d) is 1 g/L to 3 g/L, 1.8 g/L to 2.4 g/L, 2.0 g/L to 2.2 g/L or 2.1 g/L.
21. The method according to any one of embodiments 1-20, wherein the amount of first growth inhibiting agent in step (a) and/or step (d) is 1 g/L to 3 g/L, 1.7 g/L to 2.3 g/L, 1.9 g/L to 2.1 g/L or 2 g/L.
22. The method according to any one of embodiments 1-21, wherein the amount of second growth inhibiting agent in step (a) and/or step (d) is 1 g/L to 3 g/L, 1.7 g/L to 2.3 g/L, 1.9 g/L to 2.1 g/L or 2 g/L.
23. The method according to any one of embodiments 1-22, wherein the amount of third growth inhibiting agent in step (a) and/or step (d) is 0.002 g/L to 0.006 g/L, 0.003 g/L to 0.005 g/L or 0.004 g/L.

24. The method according to any one of embodiments 1-23, wherein the amount of fourth growth inhibiting agent in step (a) and/or step (d) is 0.002 g/L to 0.006 g/L, 0.003 g/L to 0.005 g/L or 0.004 g/L.

25. The method according to any one of embodiments 1-24, wherein the pre-enrichment media of step (a) and/or step (d) further comprise salts.

26. The method according to embodiment 25, wherein the salts comprise NaCl, $CaCO_3$ and/or $Na_2S_2O_3$.

27. The method according to embodiment 26, wherein the NaCl is in an amount of 0.5 g/L to 2.6 g/L, 1.0 g/L to 1.6 g/L, 1.2 g/L to 1.4 g/L or 1.3 g/L.

28. The method according to embodiment 26 or 27, wherein the $CaCO_3$ is in an amount of 18.0 g/L to 20.6 g/L, 19.0 g/L to 19.6 g/L, 19.2 g/L to 19.4 g/L or 19.3 g/L.

29. The method according to any one of embodiments 26-28, wherein the $Na_2S_2O_3$ is in an amount of 13.9 g/L to 16.5 g/L, 14.9 g/L to 15.5 g/L, 14.9 g/L to 15.5 g/L or 15.2 g/L.

30. The method according to any one of embodiments 1-29, wherein the amount of peptone in step (b) is 7.5 g/L to 8.5 g/L, 8.3 g/L to 8.9 g/L, 8.5 g/L to 8.7 g/L or 8.6 g/L.

31. The method according to any one of embodiments 1-30, wherein the amount of Bile Salts in step (b) is 4 g/L to 6 g/L, 4.4 g/L to 5.0 g/L, 4.6 g/L to 4.8 g/L or 4.7 g/L.

32. The method according to any one of embodiments 1-31, wherein the amount of Meat Extract in step (b) is 3 g/L to 5 g/L, 4.0 g/L to 4.6 g/L, 4.2 g/L to 4.4 g/L or 4.3 g/L.

33. The method according to any one of embodiments 1-32, wherein the amount of first growth inhibiting agent in step (b) is 3 g/L to 5 g/L, 3.7 g/L to 4.3 g/L, 3.9 g/L to 4.1 g/L or 4 g/L.

34. The method according to any one of embodiments 1-33, wherein the amount of second growth inhibiting agent in step (b) is 3 g/L to 5 g/L, 3.7 g/L to 4.3 g/L, 3.9 g/L to 4.1 g/L or 4 g/L.

35. The method according to any one of embodiments 1-34, wherein the amount of third growth inhibiting agent in step (b) is 0.002 g/L to 0.006 g/L, 0.003 g/L to 0.005 g/L or 0.004 g/L.

36. The method according to any one of embodiments 1-35, wherein the amount of fourth growth inhibiting agent in step (b) is 0.002 g/L to 0.006 g/L, 0.003 g/L to 0.005 g/L or 0.004 g/L.

37. The method according to any one of embodiments 1-36, wherein the enrichment media of step (b) further comprise salts.

38. The method according to embodiment 37, wherein the salts comprise NaCl, $CaCO_3$ and/or $Na_2S_2O_3$.

39. The method according to embodiment 38, wherein the NaCl is in an amount of 0.3 g/L to 3.9 g/L, 2.3 g/L to 2.9 g/L, 2.5 g/L to 2.7 g/L or 2.6 g/L.

40. The method according to embodiment 38 or 39, wherein the $CaCO_3$ is in an amount of 37.4 g/L to 40.0 g/L, 38.4 g/L to 39.0 g/L, 38.6 g/L to 38.8 g/L or 38.7 g/L.

41. The method according to any one of embodiments 38-40, wherein the $Na_2S_2O_3$ is in an amount of 29.2 g/L to 31.8 g/L, 30.2 g/L to 30.8 g/L, 30.4 g/L to 30.6 g/L or 30.5 g/L.

42. The method according to any one of embodiments 1-41, wherein the first pre-enrichment media in step (a), the enrichment media in step (b) and/or the second pre-enrichment media step (d) further comprises a growth enhancing agent.

43. The method according to embodiment 42, wherein the growth enhancing agent is a siderophore.

44. The method according to embodiment 43, wherein the siderophore is Aerobactin, Alcaligin, Azotobactin, Bacillibactin, Desferrioxamine B, Desferrioxamine E, Enterobactin, Ferrichrome, Ferrioxiamina-B, Ferrioxiamina-E, Fusarinine C, Mycobactin, Ornibactin, Petrobactin, Pyoverdine, Pyochelin, Salmochelin, Staphyloferring A, Vibriobactin, or Yersiniabactin.

45. The method according to any one of embodiments 1-44, wherein the incubation in step (a) at about 35° C. to about 39° C.

46. The method according to embodiment 45, wherein the incubation in step (a) at about 36° C. to about 38° C.

47. The method according to any one of embodiments 1-46, wherein the incubation in step (a) is for about 6 hours to about 9 hours.

48. The method according to embodiment 47, wherein the incubation in step (a) is for about 7 hours to about 8 hours.

49. The method according to any one of embodiments 1-48, wherein the aliquot of first pre-enrichment media in step (b) is about ⅕ to about 1/500 a volume of an enrichment media used in step (b).

50. The method according to any one of embodiments 1-49, wherein the incubation in step (b) at about 35° C. to about 44° C.

51. The method according to embodiment 50, wherein the incubation in step (b) at about 36° C. to about 43° C.

52. The method according to embodiment 51, wherein the incubation in step (b) at about 37° C. to about 42° C.

53. The method according to any one of embodiments 1-52, wherein the incubation in step (b) is for about 15 hours to about 19 hours.

54. The method according to embodiment 53, wherein the incubation in step (b) is for about 16 hours to about 18 hours.

55. The method according to any one of embodiments 1-54, wherein the liquid enrichment medium of step (c) or the aliquot thereof is purified using an immuno-precipitation procedure.

56. The method according to embodiment 55, wherein the immuno-precipitation procedure employs immunmagnetic particles comprising an antibody or an aptamer for a *Salmonella* live vaccine strain linked to magnetic particles.

57. The method according to any one of embodiments 1-56, wherein the incubation in step (d) at about 35° C. to about 44° C.

58. The method according to embodiment 57, wherein the incubation in step (d) at about 36° C. to about 43° C.

59. The method according to embodiment 58, wherein the incubation in step (d) at about 37° C. to about 42° C.

60. The method according to any one of embodiments 1-59, wherein the incubation in step (d) is for about 1 hours to about 4 hours.

61. The method according to embodiment 60, wherein the incubation in step (d) is for about 1 hours to about 3 hours.

62. The method according to any one of embodiments 1-61, wherein detection step (e) is performed using a sensor-based detection method, a nucleic acid-based detection method, a protein-based detection method, an activity-based detection method, or a growth-based detection method.

63. The method according to embodiment 62, wherein the sensor-based detection method is an electrochemical detection method.

64. The method according to claim 63, wherein the electrochemical detection method comprises an enzymatic biosensor, a DNA sensor, or an immunosensor.

65. The method according to embodiment 63 or 64, wherein the electrochemical detection method measures potentiometric parameters, amperometric parameters, voltametric parameters, impedimetric/conductimetric parameters, or any combination thereof.

66. The method according to embodiment 62, wherein the nucleic acid-based detection method comprises a DNA-based detection method or an RNA-based detection method.

67. The method according to embodiment 66, wherein the DNA-based detection method comprises a Southern blot analysis, a PCR-based assay, a sequence analysis, an immuno-based detection assay, or a hybridization assays using FRET, polarization or other fluorescent, chemiluminescent or bioluminescent detection.

68. The method according to embodiment 67, wherein the PCR-based assay comprises a real-time PCR-based assay.

69. The method according to embodiment 66, wherein the RNA-based detection method comprises a Northern blot analysis, a RT-PCR-based assay, a RNA sequence analysis, an immuno-based detection assay, or a hybridization assays using FRET, polarization or other fluorescent, chemiluminescent or bioluminescent detection.

70. The method according to embodiment 62, wherein the protein-based detection method is a gel-based detection method, an immuno-based detection method or a protein-interaction-based method.

71. The method according to embodiment 70, wherein the immuno-based detection method comprises a Western blot analysis, an ELISA, or an immunoprecipitation assay.

72. The method according to embodiment 62, wherein the activity-based detection method comprises an enzymatic activity assay or an assay based on protein function.

73. The method according to embodiment 72, wherein the enzymatic activity assay uses a spetrophotometric detection method measures a disappearance of a substrate or a formation of a product.

74. The method according to embodiment 62, wherein the growth-based detection method comprises a plating assays measuring colony formation or spectrophotometer assays measuring cell density.

75. The method according to any one of embodiments 1-74, further comprising purifying the second liquid pre-enrichment medium of step (d) or an aliquot thereof prior to step (e) to increase concentration of the *Salmonella* live vaccine strain and/or decrease contaminants;

76. The method according to embodiment 75, wherein the second liquid pre-enrichment medium or the aliquot thereof is purified using an immuno-precipitation procedure.

77. The method according to embodiment 76, wherein the immuno-precipitation procedure employs immunmagnetic particles comprising an antibody or an aptamer for a *Salmonella* live vaccine strain linked to magnetic particles.
78. A *Salmonella* live vaccine strain analysis kit comprising a pre-enrichment media and an enrichment media.
79. A *Salmonella* live vaccine strain analysis kit comprising a pre-enrichment media as defined in any one of embodiments 1-29 or 42-44 and an enrichment media as defined in any one of embodiments 1-17 or 30-44.
80. The analysis kit according to embodiment 78 or 79, further comprising a detection solution.
81. The analysis kit according to any one of embodiments 78-80, further and an electrochemical biosensor.
82. The analysis kit according to any one of embodiments 78-81, further comprising immunmagnetic particles capable of binding to a *Salmonella* live vaccine strain of interest.
83. The analysis kit according to any one of embodiments 78-82, further comprising a magnetic source used to capture the immunoparticles.
84. The analysis kit according to any one of embodiments 78-83, further comprising an instrument which is capable of measuring and/or analyzing potentiometric, voltammetric, amperometric and/or impedance/conductance parameters.
85. The analysis kit according to any one of embodiments 78-84, further comprising a suitable container.
86. The analysis kit according to any one of embodiments 78-85, further comprising a label or an insert.
87. The analysis kit according to any one of embodiments 78-86, further comprising a label or an insert describing the method as defined in any one of embodiments 1-77.

EXAMPLES

The following non-limiting examples are provided for illustrative purposes only in order to facilitate a more complete understanding of the disclosed subject matter. These examples should not be construed to limit any of the embodiments described in the present specification, including those pertaining to the methods disclosed, the type of detection employed or the type of pathogen that can be detected using the methods disclosed herein.

Example 1

Preparation of Sensors and Electrochemical Readings

Enzyme-based electrochemical sensors were manufactured using a screen printing process by depositing a series of layers of different material on a substrate material. Initially, a layer of compound paste comprising silver is deposited directly onto a polyester substrate (MYLAR® A (500 gauge); DuPont E. I. De Nemours & Co., Wilmington, Del.). A layer of silver/silver chloride, which functions as both the counter electrode and reference electrode, is then deposited over the compound paste on one side to form a wall. The third layer comprised carbon graphite (Gwent Electronic Materials Ltd., Pontypool, UK) which functions as the working electrode is deposited on the other side to form an oppossing wall. A channel is thus formed inbetween the silver/silver chloride wall and the carbon graphite wall. A layer of insulating paste (Gwent Electronic Materials Ltd., Pontypool, UK) is then deposited over the silver/silver chloride and carbon graphite layers and a pressure-sensitive adhesive (KIWO, Inc., Seabrook, Tex.) is then deposited over this insulating paste layer. A sensor is then modified by adding a biological layer within the channel by incubating the sensor in an atmosphere saturated with 5% glutaraldehyde to 5% for 5 minutes at room temperature in the presence of an enzyme solution comprising glucose dehydrogenase (GDH), which is then dried for 30 minutes at 37° C. Finally, a layer of polyester (MELINEX®; DuPont E. I. De Nemours & Co., Wilmington, Del.) is placed on top of the insulating paste layer to cover the sensor and enclose the channel. The sensor is then heated at 60° C. and pressure applied using a pressure roller to set the polyester layer. The sensor is stored in a dry place at 4° C. until needed.

Presence of the desired pathogen was detected by measuring the electrochemical signal produced as a result of a redox reaction associated with the conversion of glucose to gluconic acid. In this detection procedure, an aliquot of the enriched pathogen culture was added to a detection solution comprising p-aminophenyl phosphate (PAPH) and glucose. Alternatively, alfanaphtylphosphate may be used instead of PAPH. A sensor as described above was inserted into this solution and electrochemical signals were detected amperometrically under an applied potential of about 200 mV using a PalmSens3 (a potentiostat, galvanostat, and impedance analyzer) and its accompanying software PSTrace (PalmSens BV, Utrecht, Netherlands).

Briefly, the mechanism underlying the generation of an electrochemical signal is as follows. Pathogens detected using this procedure synthesize the enzyme alkaline phosphatase (ALP), which is subsequently released into the culture media. Addition of an enriched pathogen culture comprising ALP results in the hydrolysis PAPH into PAP. GDH, immobilized in the biological layer of the sensor, catalyzes the conversion of glucose into gluconic acid, which is associated with a redox reaction that oxidizes PAP into PIQ. The electrochemical signals detected by the sensor occurs when it measures the electrons generated when PIQ is reduced back to PAP.

Example 2

Relationship Between Measured Electrochemical Signal, Bacterial Population and Incubation Time Generation of an electrochemical signal and its relationship with the population size of bacteria was determined by measuring the current generated by populations comprising different concentrations of bacteria. A series of 50 µL detection solutions, each comprising 500 mM acetate buffer (pH 5.7), 10 mM magnesium chloride, 1.0 mM PAPH and 10 mM glucose, was set up. Each detection solution was then mixed with a 1 mL solution of phospho-buffered saline comprising bacteria (Salmonella typhimurium) at one of the following concentrations: $1\times10^2$ cfu/mL, $1\times10^3$ cfu/mL, $1\times10^4$ cfu/mL, $1\times10^5$ cfu/mL, $1\times10^6$ cfu/mL, $1\times10^7$ cfu/mL, or $1\times10^8$ cfu/mL. The detection solution was then incubated at 37° C. for 30 minutes. The electrochemical signal for each solution was detected amperometrically under an applied potential of about 200 mV using a PalmSens3 as described above. As shown in FIG. 1, a bacterial concentration of about $1\times10^4$ cfu/mL produced a detectable signal of about 0.5 µA. In addition, a linear concentration-response curve was observed in a range of about $1\times10^5$ cfu/mL to about $1\times10^7$ cfu/mL. These results indicate that and average bacterial concentration of about $1\times10^4$ cfu/mL can be detected using the electrochemical detection method disclosed herein.

Figure 2:
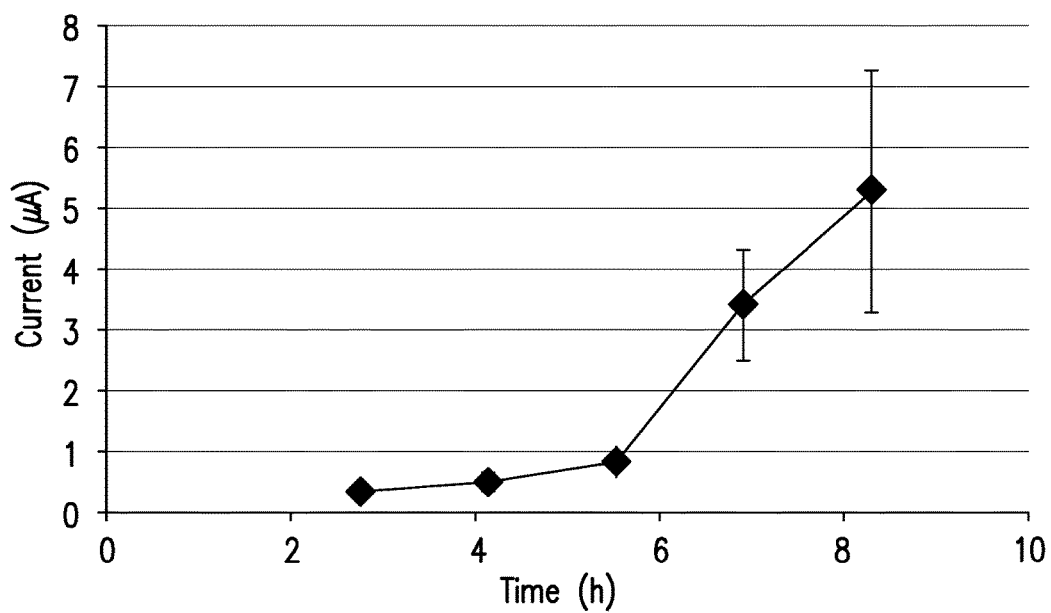
FIG. 2 shows a graph of the proportionality between the registered electrochemical signal and progress in a particular bacterial load proliferation.

Generation of an electrochemical signal and its relationship with the incubation time was determined by measuring the current generated by a bacterial population incubated over time. A 225 mL culture media comprising buffered peptone and water was inoculated with 10 cfu/mL of bacteria (S. typhimurium) and incubation at 37° C. over time. A 100 µL aliquot of this inoculated media was taken every two hours and added to a 50 µL detection solution comprising 500 mM acetate buffer (pH 5.7), 10 mM magnesium chloride, 1.0 mM PAPH and 10 mM glucose. The detection solution was then incubated at 37° C. for 30 minutes. The electrochemical signal for each solution was detected amperometrically under an applied potential of about 200 mV using a PalmSens3 as described above. As shown in FIG. 2, a detectable signal of about 0.5 µA was detected after 4 hours of incubation. A linear time-response curve was observed in a range of about 6 hours to about 8 hours. These results indicate that and average anodic current of >0.5 µA is indicative of the presence of bacteria.

Example 3

Determination of the Presence of Salmonella in Pure Culture

Generation of an electrochemical signal by a bacteria from a pure sample was determined by measuring the current generated by a defined bacterial population of two different concentrations. A 225 mL pre-enrichment culture media comprising buffered peptone and 0.4% (w/v) Tergitol-4 was inoculated with either 20 cfu or 200 cfu of bacteria (S. typhimurium), mixed vigorously for 10 seconds, and incubation at 37° C. for about 14 to about 17 hours.

After this pre-enrichment step, 1 mL of the pre-enrichment culture was taken for each bacterial concentration and a 10 µL aliquot was added to 990 µL of an enrichment culture media comprising 2.72% (w/v) of Rappaport-Vassiliadis Soya (pH 5.2) comprising 4.5 g/L soya peptone, 7.2 g/L sodium chloride, 1.26 g/L potassium dihydrogen phosphate, 0.18 mg/L dipotassium phosphate, 13.6 mg/L magnesium chloride and 0.036 g/L malachite green (Cultimed), supplemented with 0.62 mg/mL of ammonium ferric citrate (Sigma-Aldrich Corp., St. Louis, Mo.). The enrichment culture for both concentrations were incubated for about 5 to about 7 hours at 41.5° C. with circular stirring. After this enrichment step, 20 µL of a solution $3.0\times10^8$ anti-Salmonella immunomagnetic particles/mL (DYNABEADS® Anti-Salmonella, Life Technologies, Inc., Carlsbad, Calif.) was added to the enrichment cultures and incubated for 30 minutes at room temperature with agitation circular. After this incubation time, the enrichment cultures were contacted with a magnet for 3 minutes in order to localize the anti-Salmonella immunomagnetic particles within the container tube and the supernatant was extracted using 1 mL micropipette. The supernatant was then added to 1 mL of 100 mM phosphate buffer, mixed for 10 seconds, contacted with a magnet for 3 minutes and the washed supernatant was extracted using 1 mL micropipette. The processed supernatant was then tested to detect the presence of the bacteria using two different assays: 1) a plating assay; and 2) an electrochemical detection assay disclosed herein.

To detect the presence of bacteria using a plating assay, a 100 µL aliquot of the processed supernatant was mixed into 500 µL of 100 mM buffer phosphate (pH 7.4) and this mixture was plated on agar comprising a selective chromogenic agent (Chromosalm MICROKIT®, Laboratorios MICROKIT, S.L.). The agar plates were then incubated at 37° C. for about 15 hours and identifying of colored bacterial colonies determined. As shown in Table 1, growth of chromogenic bacterial colonies was observed from a supernatant sample derived from both the 20 cfu and 200 cfu of pure inoculum cultures. These results indicate that the growth methods disclosed herein in conjunction with a plating assay can effectively detect the presence of a pathogen.

TABLE 1

Detection of Salmonella in pure inoculum sample

| Experiment | n | Plating Method | | Electrochemical method | |
|---|---|---|---|---|---|
| | | Pure inoculum 20 cfu | Pure inoculum 200 cfu | Pure inoculum 20 cfu | Pure inoculum 200 cfu |
| 1 | 4 | Growth | Growth | 2.37 ± 0.52 µA | 2.45 ± 0.58 µA |

To detect the presence of bacteria using a electrochemical detection assay, a 100 µL aliquot of the processed supernatant was added to a 50 µL detection solution comprising 500 mM acetate buffer (pH 5.7), 10 mM magnesium chloride, 1.0 mM PAPH and 10 mM glucose. The detection solution was then incubated at 37° C. for 30 minutes. The electrochemical signal for each solution was detected amperometrically under an applied potential of about 200 mV verse Ag/AgCl for 30 seconds using a PalmSens3 as described above. As shown in Table 1, a current above 2 µA was detected from a supernatant sample derived from both the 20 cfu and 200 cfu of pure inoculum cultures. These results indicate that the growth methods disclosed herein in conjunction with an electrochemical detection assay disclosed herein can effectively detect the presence of a pathogen.

Example 4

Determination of the Presence of Salmonella in Fecal Sample

Generation of an electrochemical signal by a bacteria from a sample material was determined by measuring the current generated from fecal material. Twenty-five gram samples of fecal material, each suspected to contain bacteria (S. typhimurium), were added into a 225 mL pre-enrichment culture media comprising buffered peptone and 0.4% Tergitol-4 and incubation at 37° C. for about 14 to about 15 hours. Fecal material samples proven not to contain bacteria (S. typhimurium) were also tested as a negative control. The procedures regarding pre-enrichment, enrichment, and immunoseparation for Experiment 1 in Table 2 were all performed as described above in Example 3. In addition, detection of the presence of the bacteria using a plating assay and an electrochemical detection assay disclosed herein were performed as described above in Example 3. For experiments 2 and 3 in Table 1, the immunoseparation step was not performed. In these experiments, after this enrichment step, a 1 mL aliquot of enriched culture medium was centrifuged and supernatant was extracted using 1 mL micropipette. The supernatant was then added to 1 mL of 100 mM phosphate buffer, mixed for 10 seconds, centrifuged, and the washed supernatant was extracted using 1 mL micropipette. The processed supernatant was then tested to detect the presence of the bacteria using a plating assay and an electrochemical detection assay disclosed herein as described above in Example 3.

As shown in Table 2, growth of chromogenic bacterial colonies was observed from a supernatant sample derived from fecal samples contaminated with bacteria (S. typhimurium) while fecal samples not contaminated with bacteria (S. typhimurium) did not exhibit any chromogenic bacterial colonies. In addition, currents above 2 µA were detected from supernatant samples derived from fecal samples contaminated with bacteria (S. typhimurium)(Table 2). However, as shown in Table 2, currents below 0.5 µA were measured from fecal samples not contaminated with bacteria (S. typhimurium). These results indicate that a fecal sample contaminated with a pathogen can be identified and distinguished from a fecal sample not contaminated with a pathogen using the methods disclosed herein.

TABLE 2

Detection of Salmonella in fecal sample

| Experiment | n | Plating Assay | | Electrochemical Detection Assay | |
|---|---|---|---|---|---|
| | | Fecal (+) | Fecal (−) | Fecal (+) | Fecal (−) |
| 1 | 4 | Growth | No Growth | 1.97 ± 0.62 µA | 0.30 ± 0.11 µA |
| 2 | 4 | Growth | No Growth | 2.36 ± 0.20 µA | 0.25 ± 0.08 µA |
| 3 | 4 | Growth | No Growth | 3.33 ± 0.53 µA | 0.36 ± 0.08 µA |

Example 5

Determination of the Presence of Salmonella in Chicken Skin Sample

Generation of an electrochemical signal by a bacteria from a sample material was determined by measuring the current generated from skin samples from chickens. Twenty-five gram samples of chicken skin, each suspected to contain bacteria (S. typhimurium), were added into a 225 mL pre-enrichment culture media comprising buffered peptone, 0.4% (v/v) brilliant green, 0.4% (w/v) Tergitol-4, mixed vigorously for 10 seconds, and then incubation at 37° C. for about 14 to about 15 hours. Chicken skin samples proven not to contain bacteria (S. typhimurium) were also tested as a negative control. The procedures regarding pre-enrichment, enrichment, and immunoseparation for Experiment 1 in Table 2 were all performed as described above in Example 3. In addition, detection of the presence of the bacteria using a plating assay and an electrochemical detection assay disclosed herein were performed as described above in Example 3. For Experiment 2 in Table 1, the immunoseparation step was not performed. In this experiment, after this enrichment step, a 1 mL aliquot of enriched culture medium was centrifuged and supernatant was extracted using 1 mL micropipette. The supernatant was then added to 1 mL of 100 mM phosphate buffer, mixed for 10 seconds, centrifuged, and the washed supernatant was extracted using 1 mL micropipette. The processed supernatant was then tested to detect the presence of the bacteria using a plating assay and an electrochemical detection assay disclosed herein as described above in Example 3.

As shown in Table 3, growth of chromogenic bacterial colonies was observed from a supernatant sample derived from chicken skin samples contaminated with bacteria (S. typhimurium) while chicken skin samples not contaminated with bacteria (S. typhimurium) did not exhibit any chromogenic bacterial colonies. In addition, currents above 2 µA were detected from supernatant samples derived from chicken skin samples contaminated with bacteria (S. typhimurium)(Table 2). However, as shown in Table 3, currents below 0.5 µA were measured from chicken skin samples not contaminated with bacteria (S. typhimurium). These results indicate that a chicken skin sample contaminated with a pathogen can be identified and distinguished from a chicken skin sample not contaminated with a pathogen using the methods disclosed herein.

TABLE 3

Detection of *Salmonella* in chicken skin sample

| Experiment | n | Plating Assay Skin (+) | Plating Assay Skin (−) | Electrochemical Detection Assay Skin (+) | Electrochemical Detection Assay Skin (−) |
|---|---|---|---|---|---|
| 1 | 4 | Growth | No Growth | 1.84 ± 0.61 µA | 0.24 ± 0.10 µA |
| 2 | 4 | Growth | No Growth | 2.35 ± 0.49 µA | 0.35 ± 0.22 µA |

Example 6

Determination of the Presence of *Salmonella* in Foodstuff Sample

Generation of an electrochemical signal by a bacteria from a sample material was determined by measuring the current generated from foodstuff samples of corn. Twenty-five gram samples of chicken skin, each suspected to contain bacteria (*S. typhimurium*), were added into a 225 mL pre-enrichment culture media comprising buffered peptone, 0.4% (v/v) brilliant green, 0.4% (w/v) Tergitol-4, mixed vigorously for 10 seconds, and then incubation at 37° C. for about 14 to about 15 hours. Foodstuff samples proven not to contain bacteria (*S. typhimurium*) were also tested as a negative control. The procedures regarding pre-enrichment and enrichment were all performed as described above in Example 3, however, the immunoseparation step was not performed. In this experiment, after this enrichment step, a 1 mL aliquot of enriched culture medium was centrifuged and supernatant was extracted using 1 mL micropipette. The supernatant was then added to 1 mL of 100 mM phosphate buffer, mixed for 10 seconds, centrifuged, and the washed supernatant was extracted using 1 mL micropipette. The processed supernatant was then tested to detect the presence of the bacteria using a plating assay and an electrochemical detection assay disclosed herein as described above in Example 3.

As shown in Table 4, growth of chromogenic bacterial colonies was observed from a supernatant sample derived from foodstuff samples contaminated with bacteria (*S. typhimurium*) while foodstuff samples not contaminated with bacteria (*S. typhimurium*) did not exhibit any chromogenic bacterial colonies. In addition, currents above 2 µA were detected from supernatant samples derived from foodstuff samples contaminated with bacteria (*S. typhimurium*)(Table 2). However, as shown in Table 4, currents below 0.5 µA were measured from foodstuff samples not contaminated with bacteria (*S. typhimurium*). These results indicate that a foodstuff sample contaminated with a pathogen can be identified and distinguished from a foodstuff sample not contaminated with a pathogen using the methods disclosed herein.

TABLE 4

Detection of *Salmonella* in foodstuff sample

| Experiment | n | Plating Assay Foodstuff (+) | Plating Assay Foodstuff (−) | Electrochemical Detection Assay Foodstuff (+) | Electrochemical Detection Assay Foodstuff (−) |
|---|---|---|---|---|---|
| 1 | 4 | Growth | No Growth | 2.38 ± 0.62 µA | 0.62 ± 0.06 µA |

Example 7

Determination of the Presence of *Salmonella* Using Spectrophotometer Assay

Generation of an electrochemical signal by a bacteria from a sample material was determined by measuring enzymatic activity using a spectrophotometer. Twenty-five gram samples of fecal material, each suspected to contain bacteria (*S. typhimurium*), were added into a 225 mL pre-enrichment culture media comprising buffered peptone and 0.4% Tergitol-4 and incubation at 37° C. for about 16 hours. Fecal material samples proven not to contain bacteria (*S. typhimurium*) were also tested as a negative control. The procedures regarding enrichment and immunopurification were performed as described above in Example 3, except that an aliquoit of culture media was removed from the enrichment culture at each hour for the first eight hours post-inoculation and then again at 24 hours post-inoculation. The immunomagnetic particles were resuspended in 50 µL of 200 mM phosphate buffer (pH 5.7) and incubated at room temperature overnight. The incubated sample was then contacted with a magnet for 3 minutes in order to localize the immunomagnetic particles within the container tube and the supernatant was extracted using 1 mL micropipette. The 50 µL aliquot of supernatant was then added to a well from a 96-well plate containing 50 µL of substrate solution comprising 5.4 mM p-Nitrophenol phosphate. A standard solution was also prepared and comprised 0.05 mM p-Nitrophenol in 0.5 N sodium hydroxide. Control wells were also established. Negative control wells included 50 µL of 200 mM phosphate buffer (pH 5.7) and 50 µL of substrate solution. Positive control wells included 2 µL of 0.5-3 units/mg of acid phosphatase, 48 µL of 200 mM phosphate buffer (pH 5.7) and 50 µL of substrate solution. The plates were incubated at 37° C. for 30 minutes and then a 200 µL stop solution of 0.5 N sodium hydroxide. In the presence of alkaline phosphatase, the p-Nitrophenol phosphate will be converted into p-Nitrophenol, resulting in a color change. The absorbtion at 405 mn was measured for each well using a spectrophotometer. The amount of alkaline phosphatase activity for each aliquot was determined based on the standard curve generated from the standard solution.

Figure 3:
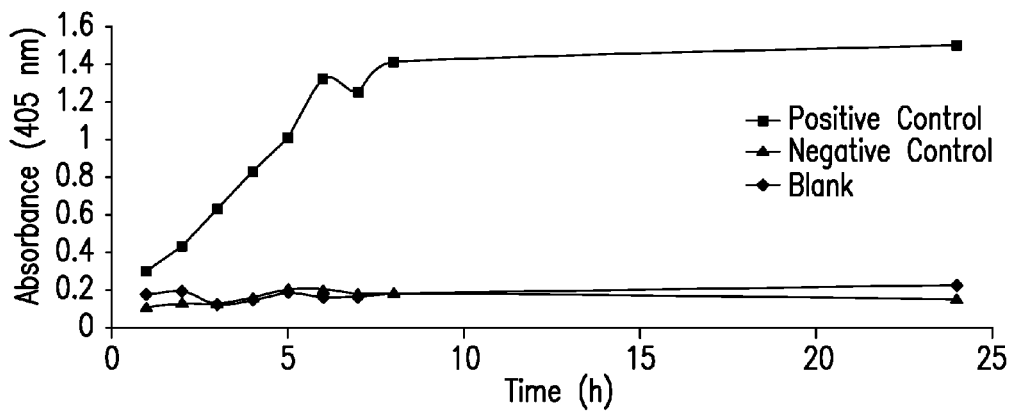
FIG. 3 shows a graph of the linear time-response curve of the presence of pathogen in fecal samples.

As shown in FIG. 3, a linear time-response curve was observed for the contaminated fecal samples for the first 6 hours with the signal then plateauing for the remainder of the time course. The blank and negative control showed no enzyme activity during the entire time course. These results indicate that the presence of bacteria can be detecting using a spectrophotometric measurements.

Example 8

Determination of the Presence of *Salmonella* Using PCR Assay

Generation of an electrochemical signal by a bacteria from a sample material was determined by measuring enzymatic activity using a spectrophotometer. Twenty-five gram samples of fecal material, each suspected to contain bacteria (*S. typhimurium*), were added into a 225 mL pre-enrichment culture media comprising buffered peptone and 0.4% Tergitol-4 and incubation at 37° C. for about 16 hours. Fecal material samples proven not to contain bacteria (*S. typhimurium*) were also tested as a negative control. The procedures regarding enrichment and immunopurification were performed as described above in Example 3. The immunomagnetic particles were resuspended in 200 μL of DNAase-free water and then heated for 30 minutes at 98° C. to lyse the cells. After centrifugation at 6000 rpm for 10 minutes at 4° C., the supernatant was transferred to a new tube. A 5 μL aliquot was added to a 15 μL PCR reaction mixture containing 10 μM of a forward and reverse primer specific for and diagnostic of *S. typhimurium*. PCR was performed as follows: 1 cycle at 95° C. for 10 minutes and up to 40 cycles of 95° C. for 30 seconds and 60° C. for 1 minute. The level of target DNA amplified during each cycle was measured by detecting fluorescence and recording the RFU. Alternatively, the assay was performed without an immunopurification step. In this case, after the incubation period for the enrichment step was completed, the culture was centrifugation at 6000 rpm for 10 minutes at 4° C., the supernatant was transferred to a new tube, and a 5 μL aliquot used for the PCR reaction.

Figure 4A:
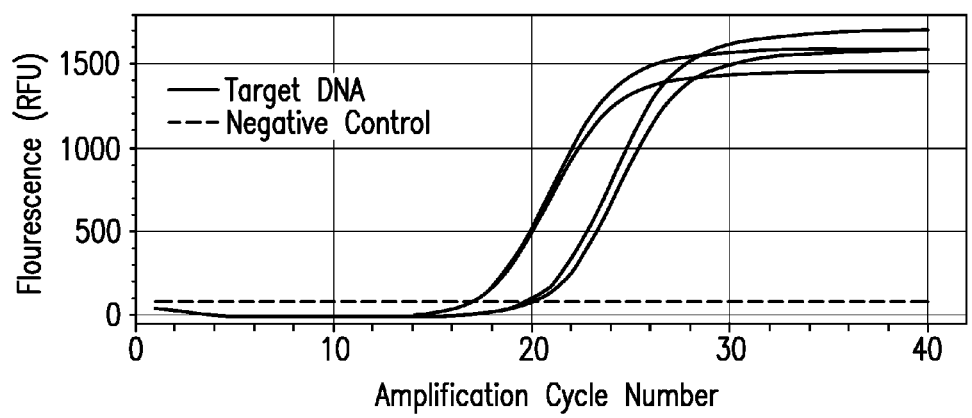
FIGS. 4A, 4B, and 4C show graphs of three independent experiments plotting the presence of target DNA amplified during each cycle of a PCR reaction.
Figure 4B:
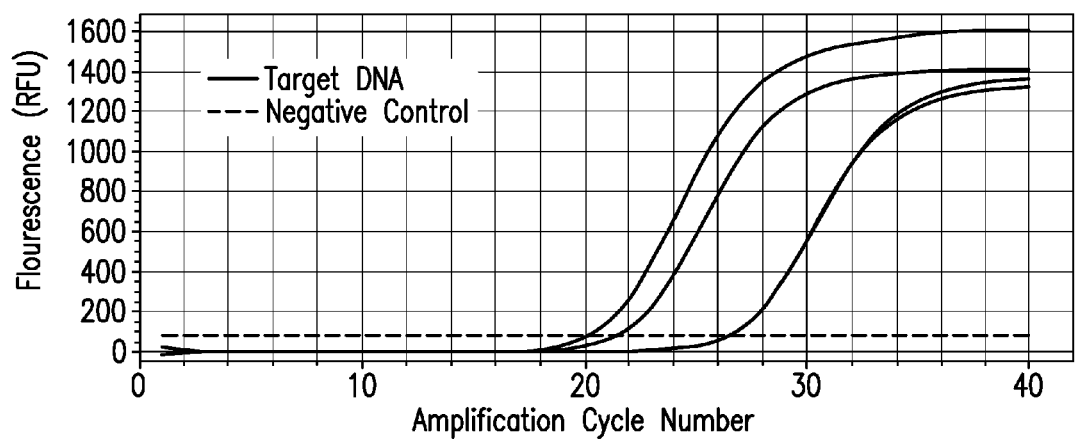
Figure 4C:
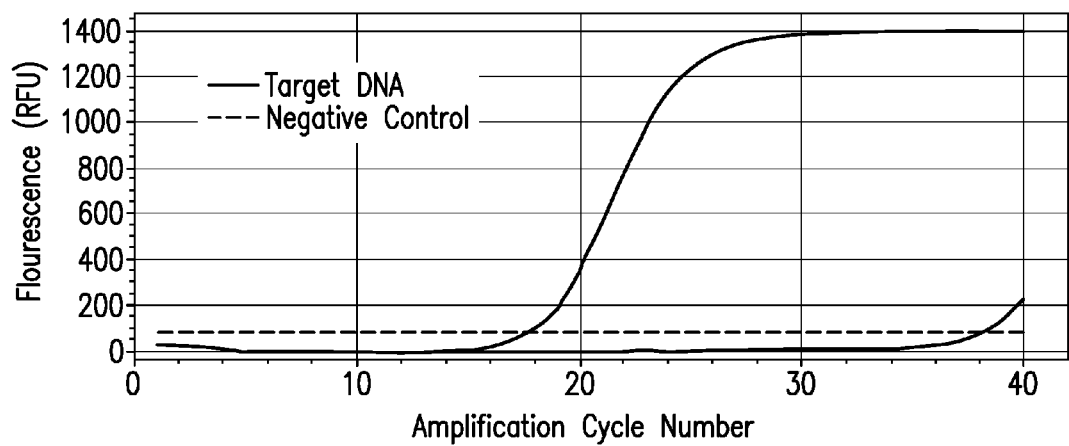

As shown in FIG. 4A-C, detection of target DNA was initially observed after 20 cycles of amplification. Amplification of target DNA exhibited a sigmoidal curve that typically began plateauing by cycle 30. The negative control showed no detectable level of target DNA amplification during the entire time course. These results indicate that the presence of bacteria can be detecting using a PCR-based assay.

Example 9

Determination of the Presence of Other Organisms

Generation of an electrochemical signal by different bacteria was determined using three different detection solutions at various bacterial concentrations. A series of 50 μL detection solutions was established for three different pH values as follows: 1) 200 mM acetate buffer (pH 5.7), 10 mM magnesium chloride, 1.0 mM PAPH and 10 mM glucose; 2) 200 mM phosphate buffer (pH 7.0), 10 mM magnesium chloride, 1.0 mM PAPH and 10 mM glucose; or 3) 200 mM TRIS buffer (pH 9.8), 10 mM magnesium chloride, 1.0 mM PAPH and 10 mM glucose. Each detection solution was then mixed with a 1 mL solution of phospho-buffered saline comprising a bacteria at one of the following concentrations: $1 \times 10^2$ cfu/mL, $1 \times 10^3$ cfu/mL, $1 \times 10^4$ cfu/mL, $1 \times 10^5$ cfu/mL, $1 \times 10^6$ cfu/mL, $1 \times 10^7$ cfu/mL, or $1 \times 10^8$ cfu/mL. The bacteria tested were as follows: *Campylobacter jejuni* Cluster 1, *Campylobacter jejuni* ST45, *Campylobacter coli*, *Escherichia coli*, *Salmonella typhimurium*, *Pseudomonas* sp., *Pseudomonas aureginosa*, *Enterobacter cloacae*, MRSA, *Proteus* sp., *Bacillus thuringiensis*, *Citrobacter* sp., *Shigella* sp., *Staphylococccus aureus*, *Klebsiella pneumoniae*, and *Enterococcus faecalis*. After the bacteria was added, these detection solution was mixed for 10 seconds and then incubated at 37° C. for 30 minutes. Detection of the presence of the bacteria using an electrochemical detection assay disclosed herein were performed as described above in Example 3.

Figure 5:
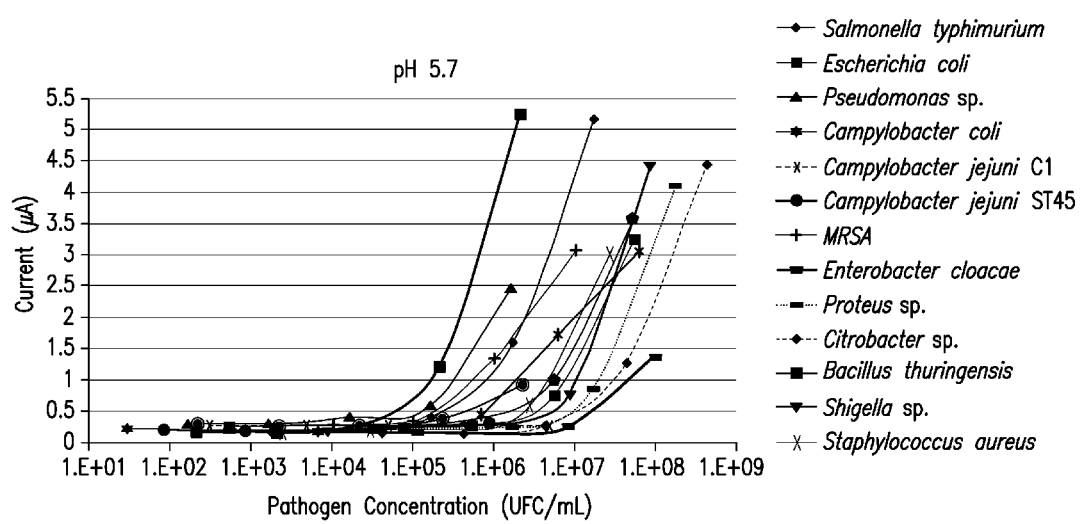
FIG. 5 shows a graph of the proportionality between the registered electrochemical signal and progress in a particular bacterial load proliferation at pH 5.7. Bacterium were contacted with 1 mM pAPP, pH 5.7 for 30 minutes at 37° C. CA E=0.2 V t=60 s PalmSens PS06333.
Figure 6:
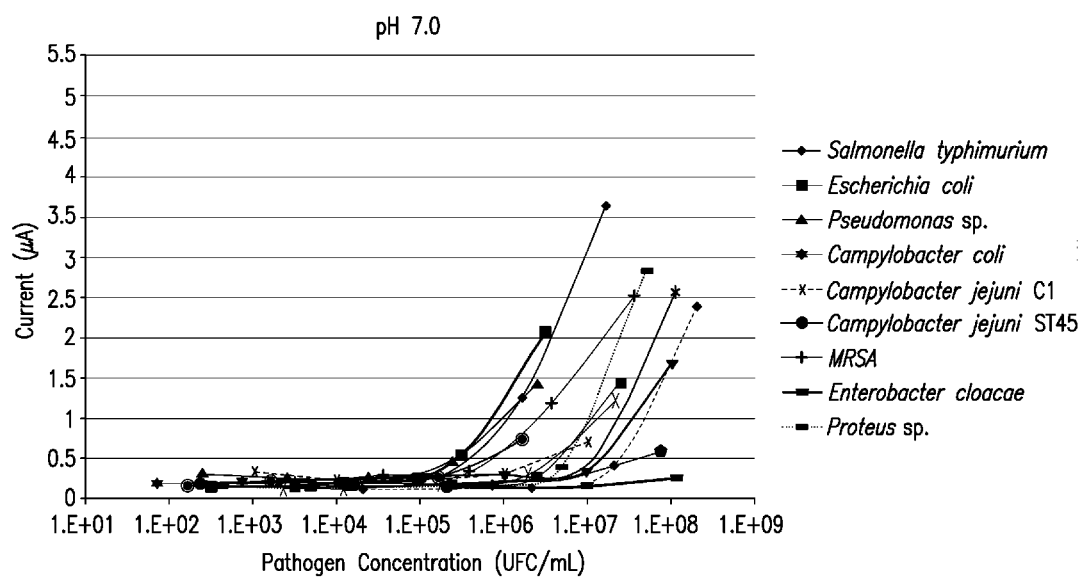
FIG. 6 shows a graph of the proportionality between the registered electrochemical signal and progress in a particular bacterial load proliferation at pH 7.0. Bacterium were contacted with 1 mM pAPP, pH 5.7 for 30 minutes at 37° C. CA E=0.2 V t=60 s PalmSens PS06333.
Figure 7:
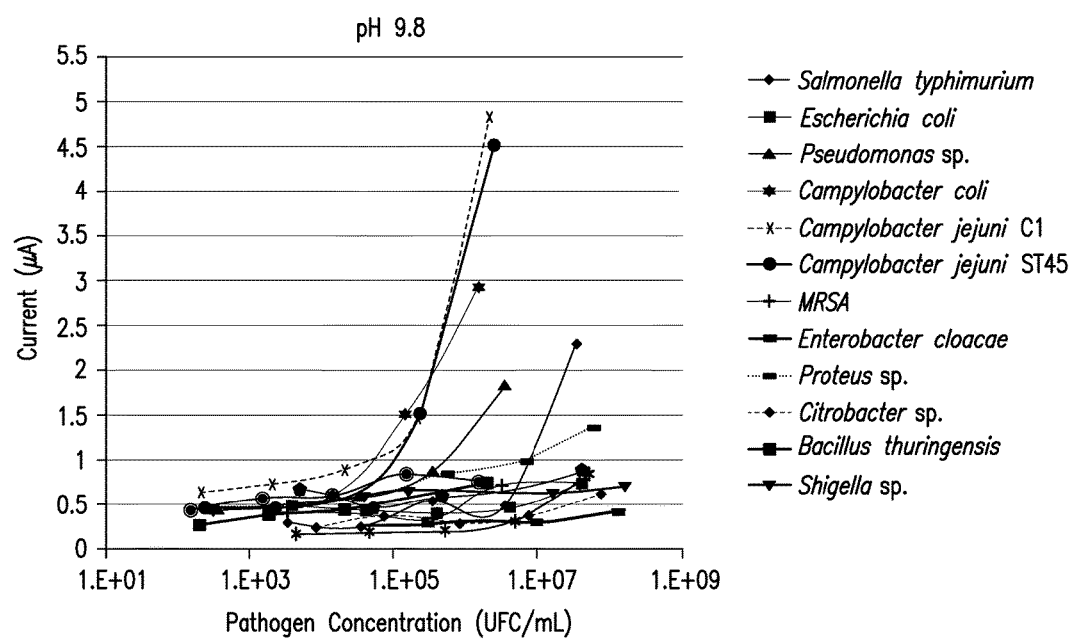
FIG. 7 shows a graph of the proportionality between the registered electrochemical signal and progress in a particular bacterial load proliferation at pH 9.8. Bacterium were contacted with 1 mM pAPP, pH 5.7 for 30 minutes at 37° C. CA E=0.2 V t=60 s PalmSens PS06333.

As shown in FIGS. 5-7, a bacterial concentration of about $1 \times 10^4$ cfu/mL produced a detectable signal of about 0.5 μA for all bacteria tested, although pH of the detection solution had an influence on the sensitivity of detection for certain bacterial species. In addition, a linear concentration-response curve was observed in a range of about $1 \times 10^5$ cfu/mL to about $1 \times 10^7$ cfu/mL. These results indicate that and average bacterial concentration of about $1 \times 10^4$ cfu/mL can be detected using the electrochemical detection method disclosed herein.

TABLE 5

Electrochemical detection of other pathogens

| Organism | Intensity | Assay | pH 5.7 | pH 7.0 | pH 9.8 |
| --- | --- | --- | --- | --- | --- |
| *C. jejuni* Cluster 1 | >1 μA | cfu/mL | — | — | $2.11 \times 10^5$ |
| | | μA | — | — | $1.46 \pm 0.35$ |
| | <1 μA | cfu/mL | $4.94 \times 10^6$ | $1.00 \times 10^7$ | $2.11 \times 10^4$ |
| | | μA | $0.27 \pm 0.05$ | $0.70 \pm 0.08$ | $0.89 \pm 0.07$ |
| *C. jejuni* ST45 | >1 μA | cfu/mL | — | — | $2.34 \times 10^5$ |
| | | μA | — | — | $1.54 \pm 0.17$ |
| | <1 μA | cfu/mL | $8.33 \times 10^5$ | $2.34 \times 10^6$ | $2.34 \times 10^4$ |
| | | μA | $0.29 \pm 0.06$ | $0.18 \pm 0.04$ | $0.53 \pm 0.07$ |
| *C. coli* | >1 μA | cfu/mL | — | — | $1.53 \times 10^5$ |
| | | μA | — | — | $1.52 \pm 0.28$ |
| | <1 μA | cfu/mL | $3.00 \times 10^4$ | $7.17 \times 10^5$ | $1.53 \times 10^4$ |
| | | μA | $0.24 \pm 0.07$ | $0.19 \pm 0.04$ | $0.62 \pm 0.07$ |
| *E. coli* | >1 μA | cfu/mL | $5.40 \times 10^7$ | $2.04 \times 10^8$ | — |
| | | μA | $3.25 \pm 0.36$ | $1.44 \pm 0.45$ | — |
| | <1 μA | cfu/mL | $5.40 \times 10^6$ | $2.41 \times 10^6$ | $4.00 \times 10^7$ |
| | | μA | $0.74 \pm 0.10$ | $0.28 \pm 0.00$ | $0.73 \pm 0.12$ |
| *S. typhimurium* | >1 μA | cfu/mL | $1.72 \times 10^6$ | $1.65 \times 10^6$ | $3.39 \times 10^7$ |
| | | μA | $1.60 \pm 0.26$ | $1.26 \pm 0.14$ | $2.29 \pm 0.42$ |
| | <1 μA | cfu/mL | $1.72 \times 10^5$ | $1.65 \times 10^5$ | $3.39 \times 10^6$ |
| | | μA | $0.41 \pm 0.05$ | $0.25 \pm 0.01$ | $0.47 \pm 0.04$ |
| *Pseudomonas* sp. | >1 μA | cfu/mL | $1.63 \times 10^6$ | $2.45 \times 10^6$ | $3.43 \times 10^6$ |
| | | μA | $2.46 \pm 0.35$ | $1.45 \pm 0.15$ | $1.85 \pm 0.46$ |
| | <1 μA | cfu/mL | $1.63 \times 10^5$ | $2.45 \times 10^5$ | $3.43 \times 10^5$ |
| | | μA | $0.59 \pm 0.03$ | $0.47 \pm 0.11$ | $0.87 \pm 0.05$ |
| *P. aureginosa* | >1 μA | cfu/mL | * | — | — |
| | | μA | * | — | — |
| | <1 μA | cfu/mL | $2.18 \times 10^6$ | $1.65 \times 10^6$ | $1.50 \times 10^6$ |
| | | μA | $0.93 \pm 0.01$ | $0.74 \pm 0.01$ | $0.77 \pm 0.05$ |
| *E. cloacae* | >1 μA | cfu/mL | $8.99 \times 10^7$ | — | — |
| | | μA | $1.37 \pm 0.11$ | — | — |
| | <1 μA | cfu/mL | $8.99 \times 10^6$ | $9.88 \times 10^7$ | $1.28 \times 10^8$ |
| | | μA | $0.27 \pm 0.02$ | $0.25 \pm 0.02$ | $0.41 \pm 0.05$ |

TABLE 5-continued

Electrochemical detection of other pathogens

| Organism | Intensity | Assay | pH 5.7 | pH 7.0 | pH 9.8 |
|---|---|---|---|---|---|
| MRSA | >1 μA | cfu/mL | $1.01 \times 10^6$ | $3.64 \times 10^6$ | — |
|  |  | μA | $1.33 \pm 0.29$ | $1.19 \pm 0.10$ | — |
|  | <1 μA | cfu/mL | $1.01 \times 10^5$ | $3.64 \times 10^5$ | $3.23 \times 10^7$ |
|  |  | μA | $0.32 \pm 0.04$ | $0.33 \pm 0.04$ | $0.75 \pm 0.06$ |
| Proteus sp. | >1 μA | cfu/mL | $1.70 \times 10^8$ | $4.92 \times 10^7$ | $5.79 \times 10^7$ |
|  |  | μA | $4.10 \pm 0.31$ | $2.82 \pm 0.16$ | $1.36 \pm 0.05$ |
|  | <1 μA | cfu/mL | $1.70 \times 10^7$ | $4.92 \times 10^6$ | $5.79 \times 10^5$ |
|  |  | μA | $0.86 \pm 0.09$ | $0.41 \pm 0.01$ | $0.85 \pm 0.05$ |
| B. thuringiensis | >1 μA | cfu/mL | $2.11 \times 10^5$ | $3.11 \times 10^6$ | — |
|  |  | μA | $1.22 \pm 0.24$ | $2.08 \pm 0.10$ | — |
|  | <1 μA | cfu/mL | $2.11 \times 10^4$ | $3.11 \times 10^5$ | $1.93 \times 10^6$ |
|  |  | μA | $0.26 \pm 0.04$ | $0.55 \pm 0.07$ | $0.74 \pm 0.06$ |
| Citrobacter sp. | >1 μA | cfu/mL | $4.23 \times 10^7$ | $2.06 \times 10^8$ | — |
|  |  | μA | $1.27 \pm 0.08$ | $2.40 \pm 0.08$ | — |
|  | <1 μA | cfu/mL | $4.23 \times 10^6$ | $2.06 \times 10^7$ | $7.62 \times 10^7$ |
|  |  | μA | $0.27 \pm 0.04$ | $0.41 \pm 0.05$ | $0.62 \pm 0.11$ |
| Shigella sp. | >1 μA | cfu/mL | $8.66 \times 10^7$ | $9.87 \times 10^7$ | — |
|  |  | μA | $4.46 \pm 0.44$ | $1.68 \pm 0.31$ | — |
|  | <1 μA | cfu/mL | $8.66 \times 10^6$ | $9.87 \times 10^6$ | $1.60 \times 10^8$ |
|  |  | μA | $0.78 \pm 0.09$ | $0.35 \pm 0.05$ | $0.69 \pm 0.15$ |
| S. aureus | >1 μA | cfu/mL | $2.63 \times 10^7$ | $2.15 \times 10^7$ | — |
|  |  | μA | $2.99 \pm 0.23$ | $1.22 \pm 0.20$ | — |
|  | <1 μA | cfu/mL | $2.63 \times 10^6$ | $2.15 \times 10^6$ | $9.44 \times 10^6$ |
|  |  | μA | $0.56 \pm 0.05$ | $0.31 \pm 0.07$ | $0.49 \pm 0.13$ |
| K. pneumoniae | >1 μA | cfu/mL | $6.20 \times 10^6$ | $1.12 \times 10^8$ | — |
|  |  | μA | $1.74 \pm 0.08$ | $2.56 \pm 0.32$ | — |
|  | <1 μA | cfu/mL | $6.20 \times 10^5$ | $1.12 \times 10^7$ | $4.43 \times 10^7$ |
|  |  | μA | $0.41 \pm 0.02$ | $0.49 \pm 0.13$ | $0.82 \pm 0.17$ |
| E. faecalis | >1 μA | cfu/mL | $4.84 \times 10^7$ | — | — |
|  |  | μA | $3.82 \pm 0.92$ | — | — |
|  | <1 μA | cfu/mL | $4.84 \times 10^6$ | $7.33 \times 10^7$ | $4.72 \times 10^7$ |
|  |  | μA | $0.92 \pm 0.01$ | $0.54 \pm 0.03$ | $0.86 \pm 0.08$ |

Example 10

Determination of the Presence of *Salmonella* Live Vaccine Strain

Generation of an electrochemical signal by a *Salmonella* live vaccine strain from a sample material was determined by measuring the current generated from fecal material. Twenty-five gram samples of fecal material were spiked with about $1 \times 10^4$ CFU/mL of *Salmonella* live vaccine strain Vac E or VacT and these samples were added to a 225 mL pre-enrichment culture media (Table 2) and incubated at about 36° C. to about 38° C. for about 7 hours to about 8 hours. Fecal material samples spiked and proven not to contain *Salmonella* were also tested as a negative control.

TABLE 6

Pre-Enrichment and Enrichment Media

| Components | Pre-Enrichment Media | Enrichment Media |
|---|---|---|
| Bile Salts | 2.4 g/L | 4.7 g/L |
| Meat Extract | 2.1 g/L | 4.3 g/L |
| Caseine Peptone | 4.3 g/L | 8.6 g/L |
| NaCl | 1.3 g/L | 2.6 g/L |
| $CaCO_3$ | 19.3 g/L | 38.7 g/L |
| $Na_2S_2O_3$ | 15.2 g/L | 30.5 g/L |
| Iodine | 2 g/L | 4 g/L |
| Potassium Iodide | 2 g/L | 4 g/L |
| Novobiocin | 4 mg/L | 4 mg/L |
| Brilliant green | 4 mg/L | 4 mg/L |

After this pre-enrichment step, a 10 μL aliquot of the pre-enrichment culture was added to 1.0 mL of an enrichment culture media (Table 6). The enrichment cultures were then incubated at about 41° C. to about 43° C. for about 16 to about 18 hours with or without circular stirring. After this enrichment step, 50 μL of a solution $3.0 \times 10^8$ anti-*Salmonella* immunomagnetic particles/mL (DYNABEADS® Anti-*Salmonella*, Life Technologies, Inc., Carlsbad, Calif.) was added to the enrichment cultures and incubated at about 36° C. to about 38° C. for about 20 minutes to about 40 minutes with circular stirring. After this incubation time, the enrichment cultures were contacted with a magnet for about 1 minute to about 3 minutes in order to localize the anti-*Salmonella* immunomagnetic particles within the container tube. After the supernatant was discarded, 1.0 mL of pre-enrichment culture media (Table 6) was added to the anti-*Salmonella* immunomagnetic particles and incubated at about 36° C. to about 38° C. for about 1 hours to about 3 hours with or without circular stirring. After this incubation time, the pre-enrichment cultures were contacted with a magnet for about 1 minute to about 3 minutes in order to localize the anti-*Salmonella* immunomagnetic particles within the container tube. After the supernatant was discarded, 1 mL of 100 mM phosphate buffer was added to the anti-*Salmonella* immunomagnetic particles within the container tube and the processed particles were then tested to detect the presence of the *Salmonella* live vaccine strains. The processed supernatant was then tested to detect the presence of the bacteria using two different assays: 1) a plating assay; and 2) an electrochemical detection assay disclosed herein.

To detect the presence of bacteria using a plating assay, a 100 μL aliquot of the processed supernatant was mixed into 500 μL of 100 mM buffer phosphate (pH 7.4) and this mixture was plated on agar comprising a selective chromogenic agent (Chromosalm MICROKIT®, Laboratorios MICROKIT, S.L.). The agar plates were then incubated at 37° C. for about 15 hours and identifying of colored bacterial colonies determined. As shown in Table 1, growth of chromogenic bacterial colonies was observed from a supernatant sample derived from both the 20 cfu and 200 cfu of pure inoculum cultures. These results indicate that the growth methods disclosed herein in conjunction with a plating assay can effectively detect the presence of a pathogen.

To detect the presence of a *Salmonella* live vaccine strain using a electrochemical detection assay, a a 50 µL detection solution comprising 185 mM sodium phosphate buffer (pH 5.7), 10 mM magnesium chloride, 1.0 mM 4-aminophenyl-Phosphate and 10 mM glucose was added to the 1.0 mL of 100 mM phosphate buffer containing the anti-*Salmonella* immunomagnetic particles. The detection solution was then incubated at 37° C. for about 30 to about 75 minutes. The electrochemical signal for each solution was detected amperometrically under an applied potential of about 200 mV verse Ag/AgCl for 30 seconds using a PalmSens3 (a potentiostat, galvanostat, and impedance analyzer) and its accompanying software PSTrace (PalmSens BV, Utrecht, Netherlands).

As shown in Table 7, growth of chromogenic bacterial colonies was observed from a supernatant sample derived from fecal samples contaminated with VacT or VacE *Salmonella* live vaccine bacteria while fecal samples not contaminated with VacT or VacE *Salmonella* live vaccine bacteria did not exhibit any chromogenic bacterial colonies. In addition, currents above 2 µA were detected from supernatant samples derived from fecal samples contaminated with VacT or VacE *Salmonella* live vaccine bacteria (Table 7). However, as shown in Table 7, currents below 0.5 µA were measured from fecal samples not contaminated with VacT or VacE *Salmonella* live vaccine bacteria. These results indicate that a fecal sample contaminated with a *Salmonella* live vaccine bacterial strain can be identified and distinguished from a fecal sample not contaminated with a pathogen using the methods disclosed herein.

TABLE 7

Detection of *Salmonella* Live Vaccine Strains in fecal sample

| Experiment | n | Plating Assay | | Electrochemical Detection Assay | |
|---|---|---|---|---|---|
| | | Fecal (+) | Fecal (−) | Fecal (+) | Fecal (−) |
| Vac E | 4 | Growth | No Growth | 2.99 ± 0.47 µA | 0.30 ± 0.11 µA |
| Vac T | 4 | Growth | No Growth | 2.89 ± 0.12 µA | 0.25 ± 0.08 µA |

Example 11

Determination of the Presence of *Salmonella* Live Vaccine Strain

Generation of an electrochemical signal by a *Salmonella* live vaccine strain from a sample material was determined by measuring the current generated from fecal material. Birds were vaccinated against *Salmonella* by allowing the birds to drink water containing about $1\times10^6$ to about $1\times10^7$ CFU/mL of *Salmonella* live vaccine strain Vac E or VacT. After 4 days, samples were obtained by cloacal swabbing from five different birds were obtained and processed together by innoculating 225 mL pre-enrichment culture media as described in Example 4 and incubating at about 36° C. to about 38° C. for about 7 hours to about 8 hours. Samples proven not to contain *Salmonella* were also tested as a negative control.

The incubated pre-enrichment culture media was incubated in an enrichment media, purified, incubated in a pre-enrichment media, purified as described in Example 10. In addition, detection of the presence of the bacteria using a plating assay and an electrochemical detection assay disclosed herein were performed as described above in Example 10.

As shown in Table 8, with respect to the plating assay, growth of chromogenic bacterial colonies was observed from a supernatant sample derived from fecal samples obtained from cloacal swabs containing VacT or VacE *Salmonella* live vaccine bacteria while fecal samples not contaminated with VacT or VacE *Salmonella* live vaccine bacteria did not exhibit any chromogenic bacterial colonies. In addition, with respect to the electrochemical detection assay, currents above 2 µA were detected from supernatant samples derived from fecal samples contaminated with VacT or VacE *Salmonella* live vaccine bacteria (Table 8). However, as shown in Table 8, currents below 0.5 µA were measured from fecal samples not contaminated with VacT or VacE *Salmonella* live vaccine bacteria. These results indicate that a fecal sample obtained using a cloacal swab contaminated with a *Salmonella* live vaccine bacterial strain can be identified and distinguished from a fecal sample not contaminated with a *Salmonella* live vaccine bacteria using the methods disclosed herein.

TABLE 8

Detection of *Salmonella* Live Vaccine Strains in Cloacal Swab Samples

| Experiment | n | Plating Assay | | Electrochemical Detection Assay | |
|---|---|---|---|---|---|
| | | Cloacal (+) | Cloacal (−) | Cloacal (+) | Cloacal (−) |
| Vac E | 4 | Growth | No Growth | 2.59 ± 0.42 µA | 0.33 ± 0.10 µA |
| Vac T | 4 | Growth | No Growth | 3.02 ± 0.22 µA | 0.25 ± 0.06 µA |

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

The invention claimed is:

1. A method of detecting a *Salmonella* live vaccine strain in a sample the method comprising the steps:
   a) incubation of the sample in a liquid pre-enrichment media, the pre-enrichment media consisting essentially of 2 g/L to 6 g/L of a peptone, 0.5 g/L to 4.5 g/L of Bile Salts, 0.5 g/L to 4.5 g/L of Meat Extract, 0.001 g/L to 0.008 g/L of Novobiocin, an ansamycin antibiotic, 0.001 g/L to 0.008 g/L of Brilliant green dye, and optionally a growth enhancing agent, wherein the incubation is at about 34° C. to about 40° C. for about 5 hours to about 10 hours, and wherein the sample is a food sample, a feces sample, a cloacal swab, or a raw livestock sample;
   b) incubating an aliquot of the pre-enrichment media from step (a) in a liquid enrichment media, the enrichment media consisting essentially of 6 g/L to 10 g/L of a peptone, 3 g/L to 7 g/L of Bile Salts, 2 g/L to 6 g/L of Meat Extract, 0.001 g/L to 0.008 g/L of Novobiocin, an ansamycin antibiotic, 0.001 g/L to 0.008 g/L of Brilliant green dye, and optionally a growth enhancing agent, wherein the incubation is at about 34° C. to about 45° C. for about 14 hours to about 20 hours; and
   c) purifying an aliquot of the liquid enrichment medium to increase the concentration of the *Salmonella* live vaccine strain and/or decrease contaminants using a magnetic immuno-precipitation method employing antibodies for the *Salmonella* linked to magnetic particles;
   d) incubating an aliquot of the magnetic particles from step (c) in a liquid post-enrichment media, the post-enrichment media consisting essentially of 2 g/L to 6 g/L of a peptone, 0.5 g/L to 4.5 g/L of Bile Salts, 0.5 g/L to 4.5 g/L of Meat Extract, 0.001 g/L to 0.008 g/L of Novobiocin, an ansamycin antibiotic, 0.001 g/L to 0.008 g/L of Brilliant green dye, and optionally a growth enhancing agent, wherein the incubation is at about 34° C. to about 45° C. for about 1 hours to about 5 hours; and
   e) detecting the presence or absence of a *Salmonella* live vaccine strain by analyzing an aliquot of the liquid post-enrichment media from step (d) using an electrochemical sensor-based detection method and detecting the amount of current generated, which indicates the presence or absence of a *Salmonella* live vaccine strain.

2. The method according to claim 1, wherein the peptone in step (a), step (b) and/or step (d) is a caseine peptone.

3. The method according to claim 1, wherein the pre-enrichment media in step (a), enrichment media in step (b) and/or the post-enrichment media in step (d) comprises the growth enhancing agent.

4. The method according to claim 1, wherein the aliquot of pre-enrichment media in step (b) is about 1/5 to about 1/5000 a volume of an enrichment media used in step (b).

5. The method according to claim 1, wherein the electrochemical detection method comprises an enzymatic biosensor, a DNA sensor, or an immunosensor.

6. The method according to claim 1, further comprising purifying the liquid post-enrichment medium of step (d) or an aliquot thereof prior to step (e) to increase the concentration of the *Salmonella* live vaccine strain and/or decrease contaminants.

7. The method according to claim 6, wherein the liquid post-enrichment medium or the aliquot thereof is purified using an magnetic immuno-precipitation procedure.

* * * * *